(12) United States Patent
Lenz

(10) Patent No.: US 8,268,264 B2
(45) Date of Patent: Sep. 18, 2012

(54) DEVICES, SYSTEMS AND METHODS FOR SEPARATING MAGNETIC PARTICLES

(75) Inventor: Thomas Lenz, Berlin (DE)

(73) Assignee: Caprotec Bioanalytics GmbH, Berlin (DE)

( * ) Notice: Subject to any disclaimer, the term of this patent is extended or adjusted under 35 U.S.C. 154(b) by 162 days.

(21) Appl. No.: 12/658,428

(22) Filed: Feb. 5, 2010

(65) Prior Publication Data

US 2010/0200405 A1 Aug. 12, 2010

Related U.S. Application Data

(60) Provisional application No. 61/207,389, filed on Feb. 9, 2009.

(51) Int. Cl.
*B01D 43/00* (2006.01)
(52) U.S. Cl. .......... 422/527; 422/500; 422/68.1
(58) Field of Classification Search .......... 422/50, 422/68.1, 81, 500, 527, 511, 550; 210/695, 210/222; 436/174, 177, 178; 435/283.1, 435/308.1
See application file for complete search history.

(56) References Cited

U.S. PATENT DOCUMENTS

| | | | |
|---|---|---|---|
| 4,554,088 A | 11/1985 | Whitehead et al. | 252/62.54 |
| 4,628,037 A | 12/1986 | Chagnon et al. | 436/526 |
| 4,695,392 A | 9/1987 | Whitehead et al. | 252/62.54 |
| 4,695,393 A | 9/1987 | Chagnon et al. | 252/62.54 |
| 4,698,302 A | 10/1987 | Whitehead et al. | 435/94 |
| 4,935,147 A | 6/1990 | Ullman et al. | 210/695 |
| 5,033,252 A | 7/1991 | Carter | 53/425 |
| 5,052,558 A | 10/1991 | Carter | 206/439 |
| 5,145,784 A | 9/1992 | Cox et al. | 436/526 |
| 5,323,907 A | 6/1994 | Kalvelage | 206/531 |

(Continued)

FOREIGN PATENT DOCUMENTS

EP 0 136 126 6/1989

(Continued)

OTHER PUBLICATIONS von Helmholtz, Hermann. "The modern development of Faraday's conception of electricity." The Faraday Lecture to the Fellows of the Chemical Society, London, Apr. 5, 1881. Obtained by the examiner on Nov. 8, 2011 from <http://www.chemteam.info/Chem-History/Helmholtz-1881.html>.*

(Continued)

*Primary Examiner* — Yelena G Gakh
*Assistant Examiner* — Christopher A Hixson
(74) *Attorney, Agent, or Firm* — Laurence A. Greenberg; Werner H. Stemer; Ralph E. Locher

(57) ABSTRACT

A method and device for separating from samples magnetic particles that contain capture compounds on their surfaces. The device includes a sheath including a magnet and including orienting pin adapted to concentrate or direct a magnetic field of the magnet; and a magnetizable plate with lid holes for receiving a vessel lid of a vessel, the magnetizable plate configured to receive the sheath and position the orienting pin over the vessel lid. In one method, magnetic beads with attached molecules are collected in the lids of the reaction vessel by the magnetic separator device provided herein and the separated magnetic particles, which carry the molecules of interest through affinity-based attachment chemistry and are held in the lid by the magnet of the device, are released into a new vessel containing a solution by removal of the separator device without the need for pipettes or liquid handling devices.

37 Claims, 12 Drawing Sheets

U.S. PATENT DOCUMENTS

| | | | |
|---|---|---|---|
| 5,541,061 A | 7/1996 | Fodor et al. | 435/6 |
| 5,547,835 A | 8/1996 | Koster | 435/6 |
| 5,559,410 A | 9/1996 | Papazian et al. | 318/445 |
| 5,567,326 A | 10/1996 | Ekenberg et al. | 210/695 |
| 5,576,220 A | 11/1996 | Hudson et al. | 436/518 |
| 5,585,639 A | 12/1996 | Dorsel et al. | 250/458.1 |
| 5,691,141 A | 11/1997 | Koster | 435/6 |
| 5,705,628 A | 1/1998 | Hawkins | 536/25.4 |
| 6,043,031 A | 3/2000 | Koster et al. | 435/6 |
| 6,074,823 A | 6/2000 | Koster | 435/6 |
| 6,140,053 A | 10/2000 | Koster | 435/6 |
| 6,194,144 B1 | 2/2001 | Koster | 435/6 |
| 6,197,498 B1 | 3/2001 | Koster | 435/5 |
| 6,221,601 B1 | 4/2001 | Koster | 435/6 |
| 6,221,605 B1 | 4/2001 | Koster | 435/6 |
| 6,225,450 B1 | 5/2001 | Koster | 536/22.1 |
| 6,235,478 B1 | 5/2001 | Koster | 435/6 |
| 6,238,871 B1 | 5/2001 | Koster | 435/6 |
| 6,258,538 B1 | 7/2001 | Koster et al. | 435/6 |
| 6,268,144 B1 | 7/2001 | Koster | 435/6 |
| 6,274,337 B1 | 8/2001 | Parce et al. | 435/29 |
| 6,277,573 B1 | 8/2001 | Koster | 435/6 |
| 6,300,076 B1 | 10/2001 | Koster | 435/6 |
| 6,399,150 B1 | 6/2002 | Yoshimura et al. | 427/242 |
| 6,428,955 B1 | 8/2002 | Koster et al. | 435/6 |
| 6,436,635 B1 | 8/2002 | Fu et al. | 435/6 |
| 6,500,621 B2 | 12/2002 | Koster | 435/6 |
| 6,527,874 B2 | 3/2003 | Li | 148/301 |
| 6,527,971 B1 | 3/2003 | Nakamura et al. | 252/62.54 |
| 6,558,902 B1 | 5/2003 | Hillenkamp | 435/6 |
| 6,602,662 B1 | 8/2003 | Koster et al. | 435/6 |
| 6,605,213 B1 | 8/2003 | Ammann et al. | 210/222 |
| 6,716,580 B2 | 4/2004 | Gold et al. | 435/6 |
| 6,730,517 B1 | 5/2004 | Koster et al. | 436/47 |
| 6,764,822 B1 | 7/2004 | Butler et al. | 435/6 |
| 6,818,394 B1 | 11/2004 | O'Donnell-Maloney et al. | 435/6 |
| 6,890,742 B2 | 5/2005 | Ammann et al. | 435/91.2 |
| 6,942,974 B2 | 9/2005 | Brevnov | 435/6 |
| 6,991,903 B2 | 1/2006 | Fu et al. | 435/6 |
| 7,014,718 B2 | 3/2006 | Hasegawa et al. | 148/302 |
| 7,019,288 B2 | 3/2006 | Becker | 250/288 |
| 7,033,820 B2 | 4/2006 | Ammann et al. | 435/287.1 |
| 7,048,808 B2 | 5/2006 | Kaneko et al. | 148/302 |
| 7,070,740 B1 | 7/2006 | Matson et al. | 422/104 |
| 7,074,563 B2 | 7/2006 | Koster | 435/6 |
| 7,076,092 B2 | 7/2006 | Hollars et al. | 382/133 |
| 7,094,943 B2 | 8/2006 | Koster et al. | 585/930 |
| 7,118,892 B2 | 10/2006 | Ammann et al. | 435/91.2 |
| 7,141,126 B2 | 11/2006 | Kuniyoshi et al. | 148/122 |
| 7,147,686 B2 | 12/2006 | Tayn et al. | 75/244 |
| 7,172,659 B2 | 2/2007 | Tomizawa et al. | 148/101 |
| 7,198,893 B1 | 4/2007 | Koster et al. | 435/6 |
| 7,211,157 B2 | 5/2007 | Sakaki et al. | 148/103 |
| 7,258,751 B2 | 8/2007 | Tomizawa et al. | 148/101 |
| 7,279,053 B2 | 10/2007 | Shimada et al. | 148/101 |
| 7,285,338 B2 | 10/2007 | Yamashita et al. | 428/668 |
| 7,316,752 B2 | 1/2008 | Tomizawa et al. | 148/301 |
| 7,332,275 B2 | 2/2008 | Braun et al. | 435/6 |
| 7,364,897 B2 | 4/2008 | Heaney et al. | 435/287.2 |
| 7,371,292 B2 | 5/2008 | Shimada et al. | 148/302 |
| 7,384,600 B2 | 6/2008 | Burns et al. | 422/64 |
| 7,431,070 B2 | 10/2008 | Hasegawa et al. | 164/463 |
| 7,442,262 B2 | 10/2008 | Sasaki | 148/302 |
| 7,482,143 B2 | 1/2009 | Ammann et al. | 435/91.2 |
| 2003/0038071 A1 | 2/2003 | Hansen et al. | 210/222 |
| 2003/0119021 A1 | 6/2003 | Koster et al. | 435/6 |
| 2004/0137430 A1* | 7/2004 | Anderson et al. | 435/5 |
| 2004/0209255 A1 | 10/2004 | Koster et al. | 435/6 |
| 2005/0042771 A1 | 2/2005 | Koster et al. | 436/518 |
| 2005/0239127 A1 | 10/2005 | Ammann et al. | 435/6 |
| 2006/0051879 A9 | 3/2006 | Koster et al. | 436/518 |
| 2008/0131254 A1 | 6/2008 | Cope et al. | 414/754 |
| 2008/0206751 A1 | 8/2008 | Squirrell et al. | 435/6 |

FOREIGN PATENT DOCUMENTS

| | | |
|---|---|---|
| EP | 0 180 384 | 4/1991 |
| EP | 0 625 708 | 11/1994 |
| EP | 1 485 707 | 1/2009 |
| GB | 2 005 019 | 4/1979 |
| WO | WO 94/18565 | 8/1994 |
| WO | 98/20166 | 5/1998 |
| WO | 98/59360 | 12/1998 |
| WO | 98/59361 | 12/1998 |
| WO | 98/59362 | 12/1998 |
| WO | 01/77668 | 10/2001 |
| WO | 01/77684 | 10/2001 |
| WO | WO 02/066165 | 8/2002 |
| WO | 03/077851 | 9/2003 |
| WO | 03/092581 | 11/2003 |
| WO | WO 2004/035217 | 4/2004 |
| WO | 2004/064972 | 8/2004 |
| WO | 2007/138085 | 12/2007 |
| WO | WO 2010/089138 | 8/2010 |

OTHER PUBLICATIONS

Song, Loling et al. "Photobleaching kinetics of fluorescein in quantative fluorescence microscopy." Biophysical Journal (1995) 68 2588-2600.*

International Search Report and Written Opinion, issued Jun. 7, 2010, in connection with International Patent Application No. PCT/EP2010/000736.

Caprotec GmbH brochures & flyers, "Improved proteomics through functional isolation of proteins," retrieved from <URL: caprotec.com/support/downloads.html#c306, published in 2008 [Retrieved on Jan. 25, 2010] [4 pages].

Caprotec GmbH presentations, "Towards the isolation of small molecule binding subproteomes," retrieved from <URL: caprotec.com/support/downloads.html#c306, published in 2008 [Retrieved on Jan. 25, 2010] [33 pages].

Caprotec GmbH brochures & flyers, "caproMag: Guideline for caproMag," retrieved from <URL: caprotec.com/support/downloads.html#c116, published in 2009 [Retrieved on May 27, 2010] [4 pages].

Chen, C., "Magnetism and Metallurgy of Soft Magnetic Materials," North Holland Publishing Company: Amsterdam, pp. 386-387 (1977).

Dalhoff et al., "Capture compounds for the methylome analysis," FEBS Workshop Poster, Aussois, France, Sep. 11-16, 2007. 1 page.

Dalhoff et al., "Synthesis of S-adenosyl-L-homocysteine capture compounds for selective photoinduced isolation of mehtyltransferases," Chembiochem. 11(2):256-265 (2010).

Duelsner et al., "Small molecule capture compounds—towards a targeted reduction of proteome complexity," Poster Presentation, 5th Annual US HUPO, Feb. 2009. 2 pages.

Duelsner et al., "Small molecule capture compounds—towards a targeted reduction of proteome complexity," Poster Presentation, Proteomic Forum, Mar. 2009. 1 page.

Dülsner et al., "CCMS technology enables improved proteomic analysis through functional isolation of sub-proteomes," Nature Methods 12(5):an12-13 (2008).

Eisenberg et al., "Hydrophobic moments and protein structure," Faraday Symp. Chem. Soc. 17:109-120 (1982).

Herman, B., "Chapter 8. Resonance Energy Transfer Microscopy," Meth. Cell Biol. 30:219-243 (1989).

IUPAC-IUB Commission on Biochemical Nomenclature, "A one-letter notation for amino acid sequences, tentative rules," J. Biol. Chem. 243(13):3557-3559 (1968).

IUPAC-IUB Commission on Biochemical Nomenclature, "Symbols for amino acid derivatives and peptides. Recommendations (1971)," Biochem. 11:1726-1732 (1972).

Jungkind et al., "Evaluation of automated COBAS AMPLICOR PCR system for detection of several infectious agents and its impact on laboratory management," J. Clin. Microbiol. 34(11):2778-2783 (1996).

Köster et al., "Capture compound mass spectrometry: a technology for the investigation of small molecule protein interactions," Assay Drug Dev. Technol. 5(3):381-390 (2007).

Lenz et al., "Capture compound mass spectrometry: photoinduced functional isolation and identification of S-adenosyl-L-methionine binding proteins from *Escherichia coli* DH5α whole cell lysate," Poster Presentation, Proteomic Forum, Mar. 2009. 1 page.

Luo et al., "cAMP capture compounds: a novel tool for the discovery and profiling of cAMP-binding proteins," Poster Presentation, Proteomic Forum, Mar. 2009. 1 page.

Merrifield, R., "Solid-phase peptide synthesis. III. An improved synthesis of bradykinin," Biochem. 3:1385-1390 (1964).

Musiani et al., "Chemiluminescence: a sensitive detection system in in situ hybridization," Histol. Histopathol. 13:243-248 (1998).

O'Day, W. and H. Fernandez, "Aristostomias scintillans (Malacosteidae): A deep-sea fish with visual pigments apparently adapted to its own bioluminescence," Vision Res. 14:545-550 (1974).

Rye, P. and N. Bovin, "Selection of carbohydrate-binding cell phenotypes using oligosaccharide-coated magnetic particles," Glycobiol. 7(2):179-182 (1997).

Sapan et al., "Colorimetric protein assay techniques," Biotechnol. Appl. Biochem. 29:99-108 (1999).

Sittampalam et al., "High-throughput screening: advances in assay technologies," Curr. Opin. Chem. Biol. 1(3):384-391 (1997).

Turro (Ed.), "Modern Molecular Photochemistry," Menlo Park, California, The Benjamin/Cummings Publishing Co., Inc., pp. 297-361 (1978).

Weiler et al., "Hybridisation based DNA screening on peptide nucleic acid (PNA) oligomer arrays," Nucliec Acids Res. 25(14):2792-2799 (1997).

* cited by examiner

DEVICES, SYSTEMS AND METHODS FOR SEPARATING MAGNETIC PARTICLES

RELATED APPLICATIONS

Benefit of priority is claimed to U.S. Provisional Application Ser. No. 61/207,389 to Thomas Lenz, entitled "DEVICES, SYSTEMS AND METHODS FOR SEPARATING MAGNETIC PARTICLES," filed Feb. 9, 2009, the subject matter of which is incorporated by reference herein in its entirety.

This application is related to International Patent Application No. PCT/EP2010/000736, filed Feb. 5, 2010, entitled "DEVICES, SYSTEMS AND METHODS FOR SEPARATING MAGNETIC PARTICLES," which also claims priority to U.S. Provisional Application Ser. No. 61/207,389. Where permitted, the subject matter of each of the above-referenced applications is incorporated by reference in its entirety.

FIELD

Provided herein are magnetic separation devices for separation and/or purification of magnetic particles from a sample, such as a biological sample, including blood samples, cell lysates, tissue samples, biopsies, bacterial samples and processed samples containing biological molecules and particles.

BACKGROUND

For the field of life science research, including molecular biology, the targeted analysis of molecules, particularly biomolecules, such as proteins and nucleic acids, is of high importance. Analysis of these molecules can require their separation and/or isolation from reaction mixtures or biological samples. Methodologies and techniques are well known in the art for separation and/or isolation of target molecules from a reaction mixture or complex biological sample including the methodology or technique to use coated magnetic particles to which target molecules bind to by high-affinity interaction. Many of these methodologies and techniques for separation and/or isolation of these target molecules bound to magnetic particles do not remove all or substantially all of the reaction mixture or biological sample, resulting in residual contamination, which requires further manipulation of the sample to reduce the contamination. Alternatively, part of the target molecules bound to magnetic particles are lost during removal of the reaction mixture because of inaccurate liquid handling steps such as pipetting. Further manipulation of the sample results in added time and costs for analysis, and increases the risk of loss of the target molecules during the process. Additionally, many of these methodologies and techniques do not allow for an easy transfer of the target molecule loaded magnetic beads to a new reaction vessel. This transfer may be required, because contaminants, such as other biomolecules, may be adsorbed to the walls of the original reaction vessel.

Accordingly, a need exists for methodologies and devices that allow removal of all or substantially all of any contaminating reaction mixture when separating and/or isolating molecules bound to magnetic particles from a reaction mixture with minimized loss of molecules bound to magnetic particles and easy and complete transfer of molecules bound to magnetic particles to a new reaction vessel for further manipulations such as washing steps. It is, among the objects herein, to provide such methodologies and devices.

SUMMARY

Provided herein are methods, processes and devices for removal of all or substantially all of any contaminating reaction mixture when separating and/or isolating molecules bound to magnetic particles from a reaction mixture. The methods and devices permit minimal loss of molecules bound to magnetic particles as well as easy and complete transfer of molecules bound to magnetic particles to a new reaction vessel for further manipulation.

Provided herein are methods, processes and devices for separating or isolating molecules bound to magnetic particles from a sample or reaction mixture. The methods, processes and devices permit removal of substantially all of contaminating sample fluid or reaction mixture from the molecules bound to magnetic particles with minimal loss of the molecules to magnetic particles and easy and complete transfer of the molecules bound to magnetic particles to a new reaction vessel.

Provided are devices that include a magnet; a sheath that includes an orienting pin adapted to concentrate or direct a magnetic field of the magnet; and a magnetizable plate with a lid hole for receiving a vessel lid of a vessel, where the magnetizable plate is configured to receive the sheath and position the orienting pin over the vessel lid to separate magnetic particles with linked molecules from a reaction mixture. The magnetizable plate can have one or a plurality of orienting pins and one or a plurality of lid holes to accommodate one or a plurality of vessel lids.

The magnet can be of any material, such as a high performance magnet. The magnet can be a rare earth magnet or a magnet selected from among an R-cobalt magnet and an R—Fe—B magnet, wherein R is selected from among lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu)), scandium (Sc) and yttrium (Y). The magnet can be a neodymium magnet that includes neodymium, iron, and boron, such as an alloy of the composition $Nd_2Fe_{14}B$. The magnet can be a samarium-cobalt magnet, such as a magnet having a a composition selected from among $SmCO_5$ and $Sm_2CO_{17}$.

In the devices provide herein, the magnet has a maximum energy product $(BH)_{max}$ of at least 3 Mega Gauss-Oersted (MGOe)s, and the $(BH)_{max}$ of the magnet can be selected from about 5 MGOe to about 50 MGOe, or from about 20 MGOe up to about 90 MGOe, or from about 25 MGOe up to about 50 MGOe, or at least 25 MGOe. In some embodiments, (BH)max of the magnet is from about 3 MGOe up to about 60 MGOe.

In the devices provide herein, the magnet has a remanence from about 3 kG to about 20 kG. In the devices provide herein, the magnet has an intrinsic coercivity of greater than 5 kOe, such as an intrinsic coercivity of from about 5 kOe to about 30 kOe.

In the devices provide herein, the sheath is of any non-magnetic material, such as aluminum or an aluminum alloy. Exemplary aluminum alloys include aluminum-copper, aluminum-magnesium, aluminum-manganese, aluminum-silicon, aluminum-magnesium-silicon and aluminum-zinc based aluminum alloys. In some embodiments of the device, the magnet is embedded in the sheath. The device also may be configured so that the sheath contains the magnet or the magnet is attached to the sheath. In some of the devices provided herein, the sheath includes a bottom that containing the orienting pins and the magnet is attached to the bottom of the sheath, such as to one face of the bottom of the sheath. The magnet can be attached to the sheath by any means. The magnet can be attached to the sheath by magnetic attraction to the orienting pins. The magnet can be attached to the sheath by an adhesive. The adhesive can be any appropriate adhesive, including, but not limited to, a hot melt adhesive, a thermoplastic adhesive, a waterborne adhesive, a solvent borne adhesive, a contact adhesive, a moisture curable adhesive, an ultraviolet curable adhesive, a urethane adhesive, a blocked urethane adhesive, an epoxy based adhesive, an adhesive comprising an encapsulated cureative, a polyurethane adhesive, a polyurethane reactive (PUR) adhesive, a plastic adhesive, an acrylic adhesive, a nitrocellulose adhesive, an isocyanate adhesive, a cyanoacrylate adhesive and a glue. The magnet also can be attached to the sheath by a mechanical connector, such as a screw, a bolt, a rivet, a pin, a clamp, a staple or a spring.

In some embodiments of the device provided herein, the magnet is attached to the bottom of the sheath and the sheath has no side walls. In other embodiments, the magnet is attached to the bottom of the sheath and the sheath has no front, rear or side walls and no top.

Also provided are devices that include a magnet; a sheath that includes an orienting pin adapted to concentrate or direct a magnetic field of the magnet and at least one side; and a magnetizable plate with a lid hole for receiving a vessel lid of a vessel, where the magnetizable plate is configured to receive the sheath and position the orienting pin over the vessel lid to separate magnetic particles with linked molecules from a reaction mixture. In some embodiments, the sheath includes at least two sides and optionally a bottom. The bottom and sides of the device each independently is of a thickness from 0.1 to 100 mm. In devices having at least two sides and a bottom, the bottom and the at least two sides define a cavity sized to receive the magnet through an open top or an optional closed top that is removable to expose the cavity.

In the devices provided herein, the sheath includes a bottom containing the orienting pins. The orienting pins can traverse the thickness of the bottom of the sheath but it is not necessary that the orienting pins do so. In some devices, the orienting pins do not fully traverse the thickness of the bottom of the sheath leaving one face of the bottom of the sheath unpenetrated. In some devices, the orienting pins do not fully traverse the thickness of the bottom of the sheath leaving the face of the bottom of the sheath pointing towards the magnet unperforated. In some devices, the orienting pins do not fully traverse the thickness of the bottom of the sheath leaving the face of the bottom of the sheath pointing towards the lids of the vessels unperforated. In some devices, the orienting pins do not fully traverse the thickness of the bottom of the sheath and are embedded into the material of the bottom of the sheath leaving all faces of the bottom of the sheath unperforated.

Provided herein are devices that include orienting pins of a material having a magnetic permeability higher than the magnetic permeability of the material from which the sheath is fabricated. The orienting pins are formed of iron or steel, of a mu metal, such as a nickel-iron alloy comprising at least 75% nickel, 15% iron, copper and molybdenum, of magnifer 75 (a soft magnetic alloy comprising about 80% nickel, 5% copper, 2% chromium, and 15% iron) or a material selected from among conpernik, an iron-cobalt-vanadium soft magnetic alloy (Hiperco®), an alloy of 80% Ni, 5% Mo, 0.5% Si, 0.02% Cu and Fe (Hymu 80®), Hypernik, Hypernom, Isoperm, nilomag 36, nilomag 42, nilomag 48, a nickel-iron-cobalt alloy comprising approximately 29% nickel and 17% cobalt (NILO alloy K), a nickel-iron-copper-molybdenum soft magnetic alloy (NILO alloy 77), Permalloy, 45 Permalloy, permenorm, Rhometal, sanbold, Sendust, Sinimax, Supermalloy, Permendur and 1040 steel alloy. In some embodiments, the orienting pins are of a material having a relative permeability greater than 1, 2, 3, 4, 5, 6, 7, 8, 9 or 10, or 100 or 1000.

Also provided are devices that include magnets as orienting pins or orienting pins that are of a magnetic material. The orienting pins can be alnico magnets, ferrite magnets, rare-earth magnets, and high-performance magnets. In embodiments where the orienting pins are magnets, the sheath can include a magnet or the magnet in the sheath can be omitted. When the sheath includes a magnet and the orienting pins are magnets, the magnetic North pole face of each of the orienting pins points towards the magnetic South pole face of the magnet in the sheath or the magnetic South pole face of each of the orienting pins points towards the magnetic North pole face of the magnet in the sheath. Also provided are devices in which the magnet in the sheath is configured to include orienting pins. In some embodiments, the magnet in the sheath includes protrusions of any shape that function as orienting pins.

The orienting pins or protrusions on the magnet that can serve or act as orienting pins can be of any shape. Exemplary shapes include parallelepiped including cuboid or cubus, block, ovoid, prism, antiprism, cylinder, ellipsoid, sphere, torus, cone, pyramid, obelisk, or truncated forms like truncated cone, frustum or any other polyhedron.

Also provide are devices in which the orienting pins in the sheath are arranged in any configuration, such as linearly or in a circular or quadrangular array, such as in a square or rectangular array. Any number of orienting pins can be included in the array. In some of the devices provided herein, the number of orienting pins in the sheath is an integer selected from among 1, 2, 3, 4, 5, 6, 7, 8, 9, 10, 11, 12, 13, 14, 15, 16, 17, 18, 19, 20, 24, 36, 48 or 96 or multiple thereof.

Also provides are devices where sheath includes a fit pin and the magnetizable plate includes a fit pin hole configured to receive the fit pin. In such devices, the sheath can include an edge having one or more fit pins and an opposite edge having a different number of fit pins to ensure only one orientation for the magnetizable plate and the sheath. In an exemplary device, the sheath includes one fit pin at one edge and two or more fit pins on the opposite edge, each pin configured to align with corresponding fit pin holes.

In the devices provided, the magnetizable plate is configured to accept one vessel lid of one vessel or a plurality of vessel lids of multiple vessels or a vessel lid of a vessel including multiple chambers. In embodiments where the magnetizable plate is configured to accept a plurality of vessel lids, the magnetizable plate is configured for accepting 2, 3, 4, 5, 6, 7, 8, 9, 10, 11, 12, 20, 36, 38, 64, 96 or 384 lids to 2, 3, 4, 5, 6, 7, 8, 9, 10, 11, 12, 20, 36, 38, 64, 96 or 384 separate vessels for simultaneous processing of 2, 3, 4, 5, 6, 7, 8, 9, 10, 11, 12, 20, 36, 38, 64, 96 or 384 samples. In some embodiments, the sheath and the magnetizable plate is of the same configuration, such as a square, rectangle or circle.

In the devices provided herein, the magnetizable plate is of a magnetizable material, such as steel or iron, magnifer 75, a mu metal, or an alloy selected from among conpernik, an iron-cobalt-vanadium soft magnetic alloy (Hiperco®), an alloy of 80% Ni, 5% Mo, 0.5% Si, 0.02% Cu and Fe (Hymu 80®), Hypernik, Hyperno, Isoper, nilomag 36, nilomag 42, nilomag 48, a nickel-iron-cobalt alloy comprising approximately 29% nickel and 17% cobalt (NILO alloy K), a nickel-iron-copper-molybdenum soft magnetic alloy (NILO alloy 77), Permalloy, 45 Permalloy, permenorm, Rhometal, sanbold, Sendust, Sinimax, Supermalloy, Permendur and 1040 steel alloy.

The devices provided herein optionally include a rack for holding one or more vessels, such as vial or multi-well plates. The device can include a rack configured to receive and hold one or more vials or configured to receive and hold one or more multi-well plates. The multi-well plates can be microtiter plates. Provided are devices that include a rack that is metal, glass or plastic. Also provided are devices that include a rack that is transparent, including a rack that is transparent to UV light.

In the devices provided herein, the lids of the vessel(s) can be of the same material as the vessel, such as plastic, wax or silicone, or can be of a chemically inert elastomeric material or a rigid material, or can be acrylic, urethane or medical grade silicone rubber. In some embodiments, the lids can be metal plugs coated with a material selected from among a plastic, an acrylic, a urethane and a medical grade silicone rubber. In such embodiments, the metal plugs are of iron or stainless steel. In the devices provided herein, the lids are separate (not connected) or are connected in a configuration selected from among a linear strip, a circular array and a quadrangular array.

Also provided are methods of separating magnetic particles from a sample in a vessel. The methods include as steps a) providing a magnetic separator device having a magnetizable plate as described herein; b) placing one or more lids of the vessel(s) in the corresponding holes in the magnetizable plate of the separator device; c) pressing the magnetizable plate with lids onto the vessel, engaging the lids with the vessel, thereby sealing the vessel; d) rotating the separating device 180°; e) maintaining the inverted device in that position for a predetermined period of time, wherein the magnetic particles become attracted to and maintained in the lid; f) returning the device to the starting position by turning 180°; g) removing the device with attached magnetizable plate with attached lids containing the magnetic particles from the vessel; h) replacing the vessel with a new vessel; i) pressing the device with the magnetizable plate with lids onto the new vessel, thereby engaging the lids containing the magnetic particles with the new vessel, thereby sealing the vessel; j) disengaging the sheath with embedded magnet of the device from the magnetizable plate, thereby allowing the magnetic particles to be released from the lids into the new vessel; k) removing the magnetizable plate with lids; and l) discarding the old lids.

Also provided are methods of separating magnetic particles from a sample in a vessel that include the steps of a) placing a magnetizable plate having a vessel lid hole on the vessel and orienting the vessel hole over the vessel; b) placing a vessel lid over the vessel hole; c) pressing the vessel lid onto the vessel, engaging the vessel lid with the vessel, thereby sealing the vessel with the magnetizable plate between the vessel lid and the vessel; d) engaging a sheath having a magnet to the magnetizable plate, wherein the magnetic particles become attracted to and maintained in the vessel lid; and e) removing the sheath with attached magnetizable plate and vessel lid containing the magnetic particles from the vessel.

Also provided are methods of separating magnetic particles from a reaction mixture in a vessel that include the steps of a) placing a magnetizable plate having a vessel hole on the vessel and orienting the vessel hole over the vessel, b) placing a vessel lid over the vessel hole; c) pressing the vessel lid onto the vessel, engaging the vessel lid with the vessel, thereby sealing the vessel with the magnetizable plate between the vessel and vessel lid; d) engaging a sheath having a magnet and an orienting pin to the magnetizable plate and orienting the sheath such that the orienting pin aligns with the center of the vessel lid; e) inverting the sheath while magnetically holding the plate, vessel and vessel lid; f) maintaining the inverted position for a predetermined period of time, wherein the magnetic particles become attracted to and maintained in the center of the lid; g) inverting the sheath to the initial position; h) removing the sheath with attached magnetizable plate and vessel lid containing the magnetic particles from the vessel; i) replacing the vessel with a new vessel; j) pressing the sheath with the magnetizable plate and the vessel lid onto the new vessel, engaging the vessel lid with the new vessel, thereby sealing the vessel with the magnetizable plate between the new vessel and vessel lid; k) disengaging the sheath from the magnetizable plate, thereby allowing the magnetic particles to be released from the vessel lid into the new vessel; l) removing the magnetizable plate with the vessel lid; and m) discarding the vessel lid; and optionally, (n) replacing the discarded lid with a new vessel lid and repeating steps (a) to (m) more than one time to wash the magnetic particles.

In the methods provided herein, the magnetic particles include a molecule of interest, such as a biomolecule a protein, a nucleic acid and a carbohydrate. In some methods, the biomolecule is affinity-tagged.

In the methods provided herein, the sample includes a biological mixture that contains a biological fluid or a lysate of a material selected from among a cell, a tissue sample, a biopsy, a bacteria, a yeast, a plant or a fungi. The biological fluid is selected from among urine, blood, plasma, serum, sweat, saliva, semen, stool, sputum, cerebral spinal fluid, mouth wash, tears, mucus, sperm and amniotic fluid. The biological mixture can include a biomarker. In some embodiments, the biomarker is a phenotype-specific molecule, or is associated with a disease phenotype or is associated with a healthy phenotype. In some embodiments, the biological mixture includes a mixture of drug-protein complexes.

Also provided are methods of isolating a target molecule from a sample, which include incubating the sample with a capture compound that includes a sorting function containing one member of a specific binding pair; a reactivity function, where the reactivity function forms a covalent attachment to the target molecule upon irradiation with UV light; and a variable selectivity function; irradiating the reaction mixture with UV light, whereby a covalent bond is formed between the target molecule and the reactivity function; adding magnetic particles that have on their surface the corresponding member of the specific binding pair of the sorting function; and separating the magnetic particles from the reaction mixture using a sheath containing a magnet. In some embodiments, the sheath further includes one or more orienting pins adapted to concentrate a magnetic field of the magnet. In some methods, the target molecule is a protein. In some methods, the sample includes a biological sample containing a biological fluid or a lysate of a material selected from among a cell, a tissue sample, a biopsy, a bacteria, a yeast, a plant or a fungi. The biological fluid can be selected from among urine, blood, plasma, serum, sweat, saliva, semen, stool, sputum, cerebral spinal fluid, mouth wash, tears, mucus, sperm and amniotic fluid. In some methods, the biological mixture includes a biomarker, which can be a phenotype-specific molecule or associated with a disease phenotype or associated with a healthy phenotype. In some methods, the biological mixture includes a mixture of drug-protein complexes.

In some embodiments, the irradiating step is performed at a temperature of about 0-4° C. In some embodiments, the irradiating step is performed at radiance of mW/cm$^2$ or at radiance of $\geq$5 mW/cm$^2$ or at radiance of $\geq$10 mW/cm$^2$.

In some embodiments, the irradiating step is performed at a wavelength of between 240 to 400 nm, or at a wavelength of between 320 to 400 nm or at a wavelength of between 280 to 320 nm or at a wavelength of between 240 to 280 nm. In some embodiments, the irradiating step is performed at a wavelength of 310 nm.

In embodiments where a sorting function of the capture compounds contains one member of a specific binding pair, the specific binding pair can be selected from among biotin-streptavidin, biotin-avidin, a chemokine-chemokine receptor, a growth factor-growth factor receptor, an antigen-antibody, a specific sugar and its corresponding lectin, β-glucan and a β-glucan-binding protein, and endotoxin and an endotoxin-neutralizing protein and fluorescein and anti-fluorescein antibody. In some methods, the sorting function is biotin and the corresponding member of the binding pair on the magnetic beads is avidin or streptavidin. In some methods, the sorting function is fluorescein and the corresponding member of the binding pair on the magnetic beads is an anti-fluorescein antibody.

The methods provided herein also optionally further include analysis of the isolated target molecule. The target molecule is analyzed by a method selected from among chromatography, electrophoresis, mass spectrometry and surface plasmon resonance. In some methods, the mass spectrometry analysis is selected from among time of flight mass spectrometry with matrix-assisted laser desorption ionization (MALDI-TOF), quadrupole ion trap mass spectrometry, secondary ion mass spectrometry, accelerator mass spectrometry, inductively coupled plasma-mass spectrometry, Ion Mobility Spectrometry-MS, Surface Enhanced Laser Desorption Ionization (SELDI-TOF), tandem mass spectrometry and Electrospray Ionization (ESI) mass spectrometry.

Also provided are kits that include a magnetic separator device as descried herein and magnetic particles and optionally instructions for use. In some embodiments, the kits further include one or more components selected from among a vessel, a capture compound, a buffer and a solvent. In some embodiments, the capture compound includes a sorting function, a reactivity function, and a variable selectivity function. In some embodiments, the sorting function contains one member of a specific binding pair and the kit includes magnetic particles that include on their surface the corresponding member of the binding pair. In some embodiments, the sorting function is biotin and the magnetic particle includes on its surface avidin or streptavidin. In some embodiments, the reactivity function forms a covalent attachment to a target molecule, such as protein, upon irradiation with UV light.

In some embodiments, the kit includes a vessel that is a tube, such as a Microfuge tube, or a multi-well plate, such as a microtiter plate. In some embodiments, the microtiter plate contains 6, 12, 24, 48, 96 384, 768, 864, 1536, 3456 or 6144 wells.

Also provided are systems that include a magnetic separator device provided herein; a device for providing UV light; and a capture compound containing a sorting function, a reactivity function, and a variable selectivity function. In some systems, the UV light device includes a cooling device. In some systems, the reactivity function of the capture compound forms a covalent bond with a target protein when irradiated with UV light.

Also provided are systems that include a magnetic separator device as described herein for isolating from a sample a target molecule on a magnetic particle; and a device for analysis of the isolated target molecule. In some systems, the target molecule is a biomolecule, such as a peptide, a protein, a nucleic acid or a carbohydrate. In some systems, the sample includes a biological mixture containing a biological fluid or a lysate of a material selected from among a cell, a tissue sample, a biopsy, a bacteria, a yeast, a plant or a fungi. In some systems, the biological fluid is selected from among urine, blood, plasma, serum, sweat, saliva, semen, stool, sputum, cerebral spinal fluid, mouth wash, tears, mucus, sperm and amniotic fluid. In some systems, the biological mixture includes a biomarker, such as a phenotype-specific molecule, In some embodiments, the biomarker is associated with a disease phenotype. In other embodiments, the biomarker is associated with a healthy phenotype. In some systems, the biological mixture includes a mixture of drug-protein complexes.

In the systems provided, the device for analysis is selected from among a mass spectrometer, an electrophoretic separator device, a surface plasmon resonance device and a chromatography device. In some systems, the chromatography device performs gas-liquid chromatography or high performance liquid chromatography (HPLC) or HPLC in combination with mass spectrometry. In some systems, the mass spectrometer performs time of flight mass spectrometry with matrix-assisted laser desorption ionization (MALDI-TOF), quadrupole ion trap mass spectrometry, secondary ion mass spectrometry, accelerator mass spectrometry, inductively coupled plasma-mass spectrometry, Ion Mobility Spectrometry-MS, Surface Enhanced Laser Desorption Ionization (SELDI-TOF), tandem mass spectrometry or Electrospray Ionization (ESI) mass spectrometry.

Also provided is a system that includes a magnetic separator device as described herein for isolating a magnetic particle with a target molecule from a reaction mixture; a capture compound that presents a sorting function containing one member of a specific binding pair, a reactivity function, and a variable selectivity function; magnetic particles containing the corresponding member of the specific binding pair on their surfaces; a mass spectrometer; and a computer with appropriate software. In some systems, the sorting function of the capture compound is biotin and the magnetic particle includes on its surface avidin or streptavidin. In some systems, the sorting function of the capture compound is fluorescein and the magnetic particles comprise anti-fluorescein antibodies on the surface thereof. In some systems, the reactivity function of the capture compound forms a covalent attachment to the target molecule, such as protein, upon irradiation with UV light. In some systems, a device for providing UV light is includes.

Also provided are articles of manufacture, which include a packaging material; a magnetic separator device as described herein within the packaging material; a device to provide UV light irradiation under sample cooling and a label that indicates that the device is for separating magnetic particles from a reaction mixture.

BRIEF DESCRIPTION OF THE FIGURES

FIG. 9A presents a schematic of a caprotec Capture Compound™ compound in which a core, designated Z herein, presents a reactivity function, which covalently interacts with biomolecules in a sample; a selectivity function, designated Y, which modulates the interaction of X and can be selected as moiety whose interactions are to be assessed; a sorting function, Q which can effect immobilization on a solid support, such as a magnetic bead, and an optional linker/spacer, designated W herein, that can alter solubility, steric or other properties of the such compound. FIG. 9B depicts an exemplary caprotec Capture Compound™ compound with optional spacers/solubility functions, where Z is the core or scaffold; Y is the selectivity function, X, the reactivity function; and Q is the sorting function. FIG. 9C depicts exemplary capture compounds for assessing kinases or methyl transferases in a sample; in the schematic R refers to the selectivity function Y, and presents a molecule with which a methyl transferase interacts, such as SAH. The caprotec Capture Compound™ compounds with reactivity function X and selectivity function Y are used in a variety of methods.

In addition to assessing interactions of the selectivity function Y, collections of the capture compounds, linked to magnetic beads/particles, can be used to reduce complexity in a sample. In such collections, the selectivity group (Y) is any group that modulates that reactivity of X and/or can be user selected, such as a drug or fragment thereof, for which the interactions in a sample are of interest. Thus, compounds and methods using them are provide methods for discovering, isolating and profiling members of functional protein families in samples as well as for studying interactions of selected molecules. Virtually any small molecule serves as a selectivity function within a capture compound, and samples from virtually any source can be investigated. These molecules and the devices and methods herein can be used with Capture Compound Mass Spectrometry (CCMS) technologies and compounds therefore provided by caprotec bioanalytics Gmbh and described in published applications International PCT application Nos. WO 03/092581 and WO 04/06497. A typical CCMS experiment can be divided into three phases: 1) Sample preparation, 2) reaction with the sample and covalent cross-linking of captured molecules such as proteins to capture compounds and 3) isolation and identification of captured molecules. This method can be practiced using capture compounds linked to magnetic beads. Any suitable substituent on the capture compound can be used to effect capture on a solid support. Typically, the sorting function Q is employed for this purpose. For example, where the solid support is streptavidin coated beads, Q is biotin or other molecule that interacts with streptavidin to immobilize the capture compounds. The devices provided herein can be used with any method and any capture compounds or compounds that are linked to a magnetic bead/particle.

Figure 10:
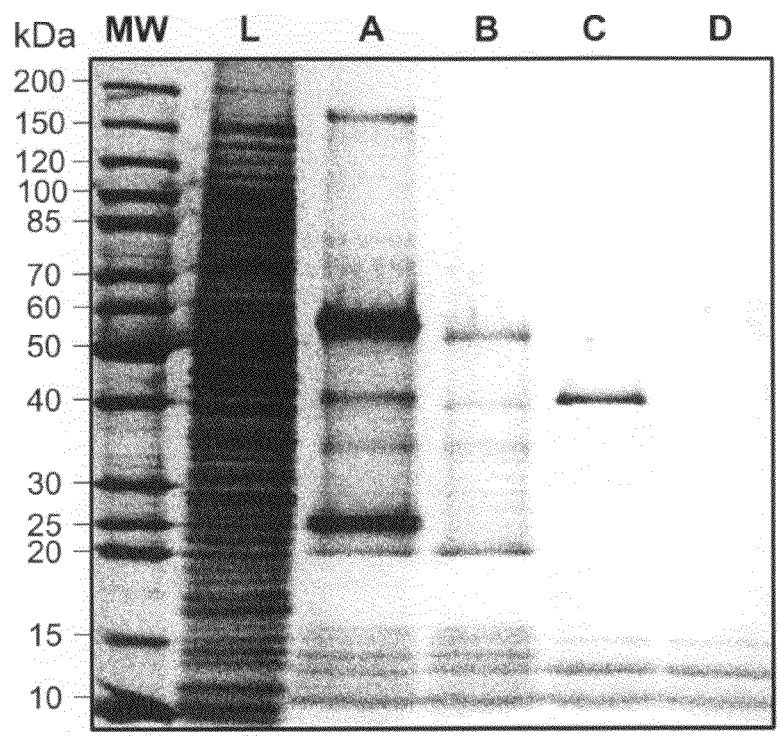

FIG. 10 is a picture of a silver stained SDS-PAGE gel that demonstrates the reduction of proteome complexity of a cell lysate. MW denotes the molecular weight marker, the bands of which are labeled in kDa to the very left of the gel picture. The comparison between the *E. coli* lysate (lane L, where only 0.25% of the original lysate was subjected to SDS-PAGE) and lysates A-D reveals the dramatic reduction of proteome complexity. The bands on the gel appearing exclusively in lysate A and not in lysate B represent SAH binding proteins covalently attached to the SAH-CC. Lysate B included bands that represent non-SAH specific proteins covalently attached to the SAH-CC. Lysate C included bands that represent proteins isolated from the lysate without covalent cross-link to the SAH-CC (pull-down) and lysate D included bands that correspond to pulled-down proteins in the presence of SAH competitor (non-specific pull-down).

Figure 11:
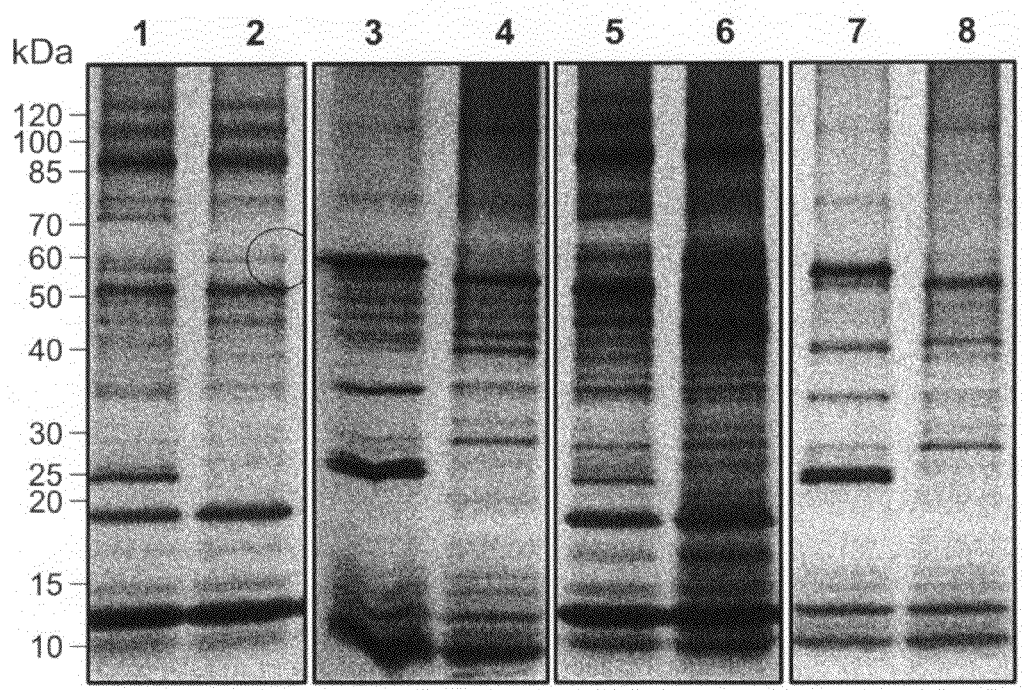

FIG. 11 is a picture of a silver stained SDS-PAGE gel of reactions performed with caproBeads™ beads presenting caprotec Capture Compound™ compounds compared to reactions performed with the corresponding capture compound in solution. Reactions performed with caproBeads™ beads presenting caprotec Capture Compound™ compound B1-N6-SAH or B2-N6-SAH (reactions 3 and 7, respectively) had fewer protein bands than reactions performed with the corresponding capture compound in solution (reactions 1 and 5, respectively). Furthermore, the majority of proteins that were captured by capture compounds in solution, but not by caproBeads™ beads, were not competed off in the presence of soluble SAH (S-adenosyl-L-homocysteine) (reactions 2 and 6, respectively). This indicates that many proteins captured by capture compounds in solution were not captured because of specific interactions with the SAH selectivity function.

Figure 12:
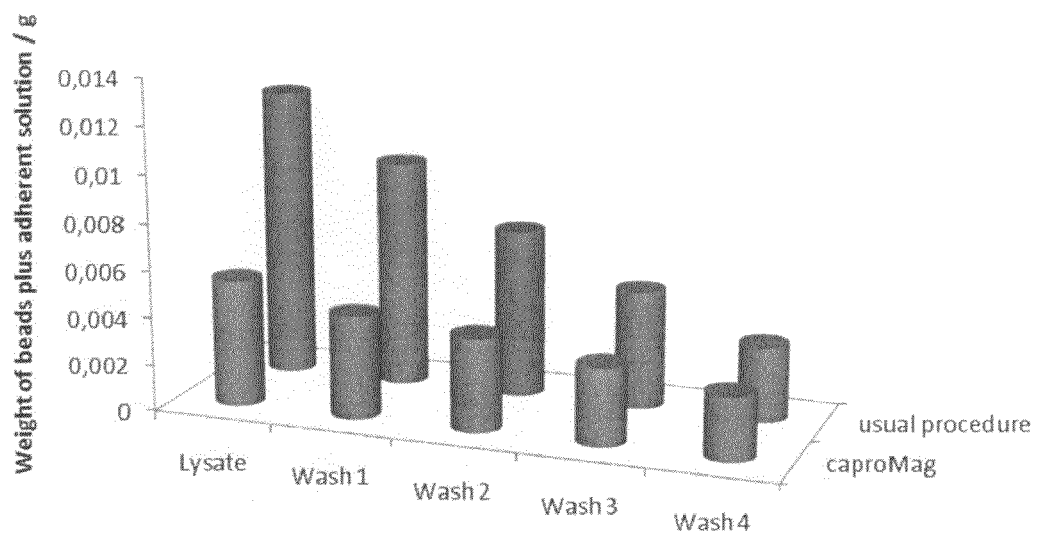

FIG. 12 is a graph showing the weights of magnetic beads plus adherent solution after magnetic separation from *Escherichia coli* cell lysate or wash solutions either using a magnetic device and washing procedure described herein, in which the magnetic beads are collected in the lid of a tube and the tube with the supernatant is discarded, the lid with beads transferred to a new tube with fresh solution, the beads dispersed into the new solution in the new tube, and the old lid replaced with a new lid (the "caproMag washing procedure"), or the usual procedure, which uses a magnet on a side of the tube to adhere the beads on the side of the tube while the supernatant is removed by pipetting for separation. Less lysate or wash solution is retained on the beads using the caproMag washing procedure, which minimizes carryover to the next wash solution, thus, minimizing the wash steps and maximizing wash performance.

Figure 13:
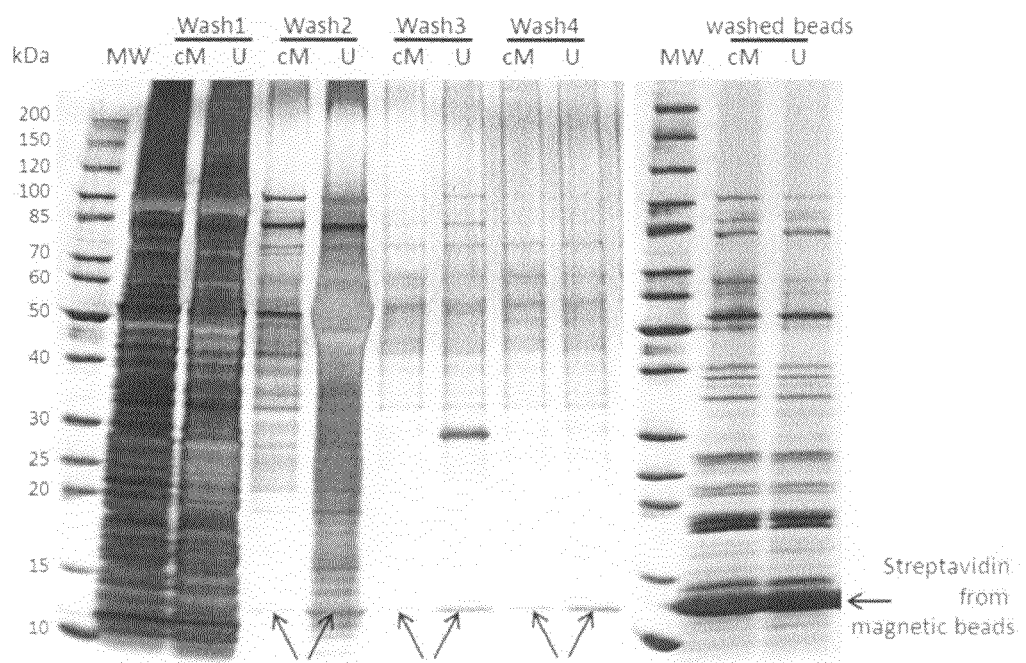
Figure 13:
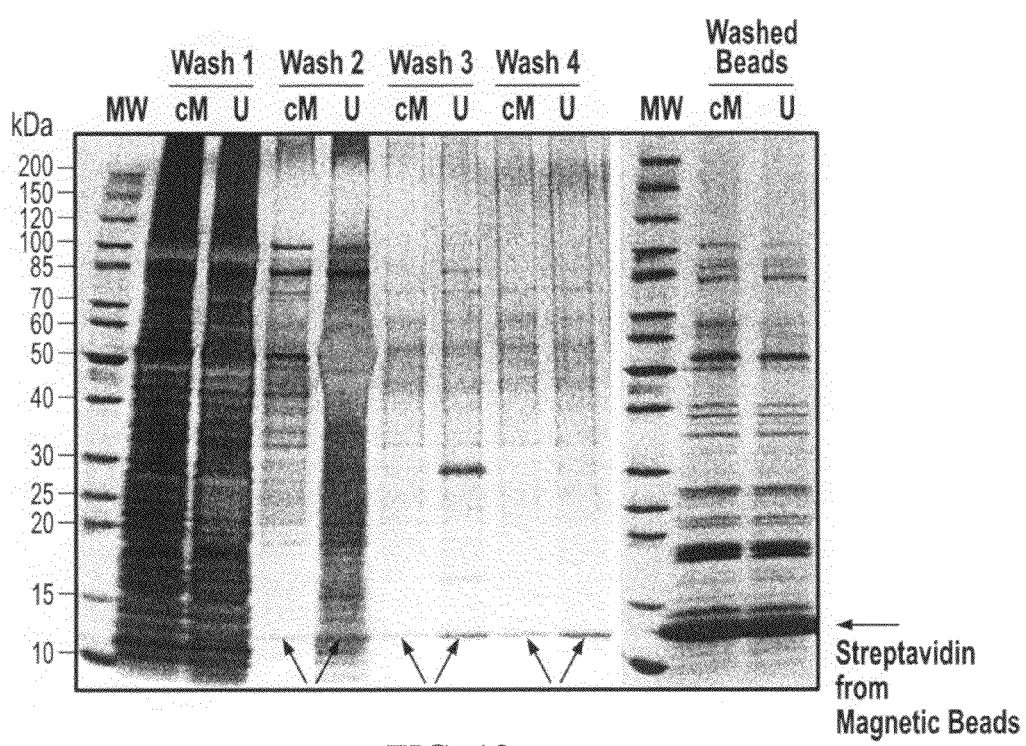

FIG. 13 is a picture of a silver stained SDS-PAGE gel of an analysis of the protein content within successive wash solutions for washing streptavidin coated magnetic beads pre-incubated with *Escherichia coli* cell lysate. The respective wash fractions are denoted on top of the gel (Wash 1-4) together with the method used for washing and separating the beads (cM=caproMag washing procedure, U=usual pipetting procedure). The protein content, which remained on the beads after washing 4 times, is analyzed in the lanes to the right denoted "washed beads." The streptavidin originating from the streptavidin coated magnetic beads is indicated by arrows. Streptavidin is only cleaved from the beads when applying harsh denaturing conditions, such as are used for preparing the SDS-PAGE samples (boiling in SDS sample buffer). Thus, the streptavidin band is a measure of the amount of beads in the sample. Using the caproMag magnetic device and washing procedure, the amount of beads unintentionally removed together with the supernatant wash solution is lower than using the usual pipetting procedure. MW denotes lanes run with molecular weight marker (PageRuler™ Unstained Protein Ladder from Fermentas Inc., Glen Burnie, Md.). The approximate molecular weights of the marker bands are given at the very left in the unit kDa.

Figure 14:
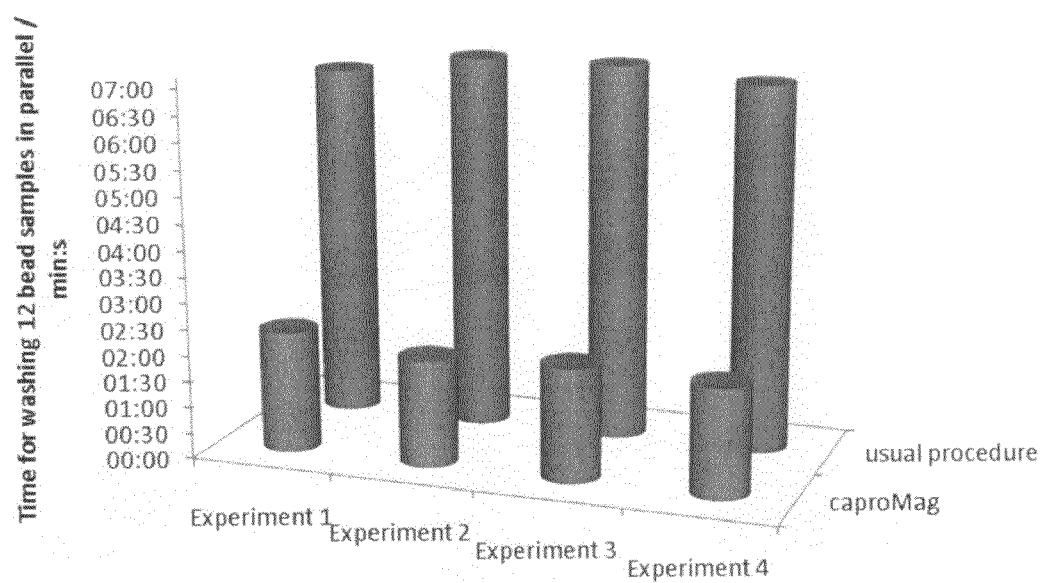

FIG. 14 is a graph showing the time for washing 12 bead samples in parallel, including the time to change the reaction tube, when using the caproMag magnetic device and washing procedure compared to the usual procedure with manual pipetting. Using the caproMag magnetic device and washing procedure results in a more than 3-fold reduction of time for washing 12 bead samples in parallel.

DETAILED DESCRIPTION

Outline

A. Definitions
B. Isolation of Target Molecules
C. Magnetic Separator Device
  1. Magnet
  2. Sheath
  3. Orienting Pins
  4. Fit Pins
  5. Magnetizable Plate
  6. Optional Rack
  7. Vessels Having Lids
D. Magnetic Particles
  1. Magnetic particles
  2. Attachment of Molecules to Magnetic Particles
E. Capture Compounds
  1. Reactivity Function—X
  2. Selectivity Function—Y
  3. Sorting Function—Q
  4. Solubility Function—W
  5. Core or Scaffold—Z
  6. Optional Spacer Moiety—E
  7. Optional Cleavable Linker—L
  8. Optional Mass Modifying Tags
  9. Exemplary Capture Compounds
F. Methods
  1. Capture Methods—Kinetic Conditions
  2. Assessing the Interaction with a Molecule—Equilibrium Conditions
  3. Functional Isolation of Target Proteins using synthetic probes
  4. Separation of Magnetic Particles with Biomolecules from a Reaction Solution
G. Systems
H. Combinations, kits and articles of manufacture
I. Examples

A. Definitions

Unless defined otherwise, all technical and scientific terms used herein have the same meaning as is commonly understood by one of skill in the art to which the inventions belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, a "biomolecule" refers to any compound found in nature, or derivatives thereof. As used herein, a "biomolecule" includes biopolymers and macromolecules and all molecules that can be isolated from living organisms and viruses, including, but are not limited to, cells, tissues, prions, animals, plants, viruses, bacteria and other organisms. Exemplary biomolecules include (deoxy)ribonucleic acid, (oligo)nucleotides, (oligo)nucleosides, proteins, peptides, amino acids, lipids, steroids, peptide nucleic acids (PNAs), monosaccharides, oligosaccharides and polysaccharides. These include synthetic as well as naturally-occurring molecules.

As used herein, a "macromolecule" refers to any molecule having a molecular weight from the hundreds up to the millions g/mol. Macromolecules include, but are not limited to, peptides, proteins, nucleotides, nucleic acids, carbohydrates, and other such molecules that are generally synthesized by biological organisms, but can be prepared synthetically or using recombinant molecular biology methods.

As used herein, the term "particle" refers to a small mass that can be composed of any material, such as alumina, glass, silica, latex, plastic, agarose, polyacrylamide, methacrylate or any polymeric material, and be of any size and shape. Typically the particles have at least one dimension in the 5-10 mm range or smaller, such as less than 50 μm or less than 10 μm. Such particles, referred to collectively as "beads" herein, are often, but not necessarily, spherical. Reference to "bead," however, does not constrain the geometry of the particle, which can be any shape, including random shapes, needles, fibers, and elongated spheroids. "Beads" also encompass microspheres, such as spheres that are less than 5 μm in diameter. The "beads" can include additional components, such as magnetic or paramagnetic particles (see, e.g., Dyna-Beads™ (Dynal, Oslo, Norway)) for separation using magnets. The beads can include on their surface moieties that allow interaction with a target molecule. For example, the beads can include one member of a specific binding pair, or any molecule that exhibits an affinity or selectively interacts with a molecule of interest.

As used herein, a "collection" refers to combination of two or more members, generally 3, 5, 10, 50, 100, 500, 1000 or more members. In particular a collection refers to such combination of capture compounds as described herein.

As used herein, an "array" refers to a collection of elements, such as capture compounds, containing three or more members. An addressable array is one in that the members of the array are identifiable, typically by position on a solid phase support but also by virtue of an identifier or detectable label. Hence, in general the members of an addressable array can be immobilized to discrete identifiable loci on the surface of a solid phase. A plurality of capture compounds can be attached to a support, such as an array (i.e., a pattern of two or more) on the surface of a support, such as a magnetic bead, generally through binding of the sorting functionality with a group or compound on the surface of the support. Addressing can be achieved by labeling each member through the use of identifiable labels, such as color coded labels and through molecular weight. These labels for addressing can serve as a sorting functions "Q."

As used herein, the term "separation" refers to process in which one or more components of a sample are spatially separated from one or more other components of a sample. A separation can be performed such that one or more sample components of interest is translocated to or retained in one or more areas of a separation apparatus and at least some of the remaining components are translocated away from the area or areas where the one or more sample components of interest are translocated to and/or retained in, or in which one or more sample components is retained in one or more areas and at least some or the remaining components are removed from the area or areas. Alternatively, one or more components of a sample can be translocated to and/or retained in one or more areas and one or more sample components can be removed from the area or areas. Separations can be achieved through, for example, filtration, or the use of physical, chemical, electrical, or magnetic forces. Non-limiting examples of forces that can be used in separations are gravity, mass flow, electrophoretic forces and electromagnetic forces.

As used herein, the term "microparticle" or "microparticle support" refers to a structure of any shape and of any composition that have a dimension typically from about 0.01 micron to about 500 microns. Such microparticles can be fabricated from any suitable material, such as glass, ceramics, and/or one or more polymers, such as, for example, nylon, polytetrafluoroethylene (TEFLON®), polystyrene, polyacrylamide, Sepharose®, agarose, cellulose, cellulose derivatives, or dextran, and/or can include metals. Examples of microparticles include, but are not limited to, plastic particles, ceramic particles, carbon particles, polystyrene microbeads, glass beads, magnetic beads, hollow glass spheres and metal particles. The microparticles can be associated with a magnetic, such as having a magnetic embedded therein or including magnetic material in their fabrication. Such microparticles are magnetic microparticles or magnetic beads.

As used herein, a "biopolymer" refers to a biological molecule, including macromolecules, composed of two or more monomeric subunits, or derivatives thereof, which are linked by a bond or a macromolecule. A biopolymer can be, for example, a polynucleotide, a polypeptide, a carbohydrate, or a lipid, or derivatives or combinations thereof, for example, a nucleic acid molecule containing a peptide nucleic acid portion or a glycoprotein. The devices, methods and collections herein, though described with reference to biopolymers, can be adapted for use with other synthetic schemes and assays, such as organic syntheses of pharmaceuticals, or inorganics and any other reaction or assay performed on a magnetic particle.

As used herein, a "biological particle" refers to a virus, such as a viral vector or viral capsid with or without packaged nucleic acid, phage, including a phage vector or phage capsid, with or without encapsulated nucleotide acid, a single cell, including eukaryotic and prokaryotic cells or fragments thereof, a liposome or micellar agent or other packaging particle, and other such biological materials. For purposes herein, biological particles include molecules that are not typically considered macromolecules because they are not generally synthesized, but are derived from cells and viruses.

As used herein, a "drug" refers to any compound that is a candidate for use as a therapeutic or as lead compound for designing a therapeutic or that is a known pharmaceutical. Such compounds can be small molecules, including small organic molecules, peptides, peptide mimetics, antisense molecules, antibodies, fragments of antibodies, recombinant antibodies.

As used herein, a "drug-protein complex" refers to an association between a drug and a protein. The association can be stabilized by electrostatic attraction, hydrophobic interaction, hydrophilic interaction, ionic interaction or hydrogen bonding. The association between the drug and the protein in a drug-protein complex may be a reversible or an irreversible association. Irreversible drug-protein complex formation is usually a result of chemical activation of the drug, which then attaches strongly to the protein by covalent chemical bonding. Irreversible drug-protein complex formation accounts for certain types of drug toxicity. A reversible drug-protein complex can dissociate, and the drug that was associated with the protein is released.

As used herein, "biological activity" refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities can be observed in in vitro systems designed to test or use such activities.

As used herein the term "assess", and grammatical variations thereof, is intended to include quantitative and qualitative determination in the sense of obtaining an absolute value for the activity of a biopolymer such as a polypeptide, and also of obtaining an index, ratio, percentage, visual or other value indicative of the level of the activity. Assessment can be direct or indirect. For example, detection of cleavage of a substrate by a polypeptide can be by direct measurement of the product, or can be indirectly measured by determining the resulting activity of the cleaved substrate.

As used herein, the term "metabolite" refers to any substance produced during metabolism of another substance. A metabolite can refer to the end-product (that which is remaining after metabolism) or a by-product of another compound.

As used herein, "specific binding pair" and "ligand-receptor binding pair" refers to two different molecules, where one of the molecules has an area on the surface or in a cavity that specifically attracts or binds to a particular spatial or polar organization of the other molecule, causing both molecules to have an affinity for each other. The members of the specific binding pair are referred to as ligand and receptor (antiligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor and tumor necrosis factor-receptor, and interferon and interferon receptor; avidin and biotin; biotin and streptavidin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and there receptors, such as granulocyte-macrophage colony stimulating factor (GMCSF) and GMCSF receptor and macrophage colony stimulating factor (MCSF) and MCSF receptor.

As used herein, the terms "specific binding" and "selective binding" refer to the binding of a targeting agent with its target, such as a particular ligand and its receptor, which is at least 2-fold, generally, 5, 10, 50, 100 or more-fold, greater than for non-target, such as another receptor. A statement that a particular compound is targeted to a target cell or target tissue means that its affinity for such cell or tissue in a host or in vitro or in vivo is at least about 2-fold, generally, 5, 10, 50, 100 or more-fold, greater than for other cells and tissues in the host or under the in vitro conditions.

As used herein, "irradiating" and "irradiation" refers to exposing a subject to a selected wavelength of light or to all wavelengths of light.

As used herein, the term "nucleic acid" refers to single-stranded and/or double-stranded polynucleotides such as deoxyribonucleic acid (DNA), and ribonucleic acid (RNA) as well as analogs or derivatives of either RNA or DNA. A nucleic acid molecule is a linear polymer of nucleotides, linked by 3',5'-phosphodiester linkages. In DNA, deoxyribonucleic acid, the sugar group is deoxyribose and the bases of the nucleotides are adenine, guanine, thymine and cytosine. RNA, ribonucleic acid, has ribose as the sugar and uracil replaces thymine. Also included in the term "nucleic acid" are analogs of nucleic acids such as peptide nucleic acid (PNA), phosphorothioate DNA, and other such analogs and derivatives or combinations thereof.

As used herein, the term "polynucleotide" refers to an oligomer or polymer containing at least two linked nucleotides or nucleotide derivatives, including a deoxyribonucleic acid (DNA), a ribonucleic acid (RNA), and a DNA or RNA derivative containing, for example, a nucleotide analog or a "backbone" bond other than a phosphodiester bond, for example, a phosphotriester bond, a phosphoramidate bond, a methylphosphonate diester bond, a phosphorothioate bond, a thioester bond, or a peptide bond (peptide nucleic acid). The term "oligonucleotide" also is used herein essentially synonymously with "polynucleotide," although those in the art recognize that oligonucleotides, for example, PCR primers, generally are less than about fifty to one hundred nucleotides in length.

Nucleotide analogs contained in a polynucleotide can be, for example, mass modified nucleotides, which allows for mass differentiation of polynucleotides; nucleotides containing a detectable label such as a fluorescent, radioactive, colorimetric, luminescent or chemiluminescent label, which allows for detection of a polynucleotide; or nucleotides containing a reactive group such as biotin or a thiol group, which facilitates immobilization of a polynucleotide to a solid support. A polynucleotide also can contain one or more backbone bonds that are selectively cleavable, for example, chemically, enzymatically or photolytically. For example, a polynucleotide can include one or more deoxyribonucleotides, followed by one or more ribonucleotides, which can be followed by one or more deoxyribonucleotides, such a sequence being cleavable at the ribonucleotide sequence by base hydrolysis. A polynucleotide also can contain one or more bonds that are relatively resistant to cleavage, for example, a chimeric oligonucleotide primer, which can include nucleotides linked by peptide nucleic acid bonds and at least one nucleotide at the 3' end, which is linked by a phosphodiester bond, and is capable of being extended by a polymerase. Peptide nucleic acid sequences can be prepared using well known methods (see, for example, Weiler et al., Nucleic acids Res. 25: 2792-2799 (1997).

As used herein, a "selectively cleavable" moiety is a moiety that can be selectively cleaved without affecting or altering the composition of the other portions of the compound of interest. For example, a cleavable moiety L of the compounds provided herein is one that can be cleaved by chemical, enzymatic, photolytic, or other means without affecting or altering composition (e.g., the chemical composition) of the conjugated biomolecule, including a protein. "Non-cleavable" moieties are those that cannot be selectively cleaved without affecting or altering the composition of the other portions of the compound of interest.

A polynucleotide can be a portion of a larger nucleic acid molecule, for example, a portion of a gene, which can contain a polymorphic region, or a portion of an extragenic region of a chromosome, for example, a portion of a region of nucleotide repeats such as a short tandem repeat (STR) locus, a variable number of tandem repeats (VNTR) locus, a microsatellite locus or a minisatellite locus. A polynucleotide also can be single stranded or double stranded, including, for example, a DNA-RNA hybrid, or can be triple stranded or four stranded. Where the polynucleotide is double stranded DNA, it can be in an A, B, L or Z configuration, and a single polynucleotide can contain combinations of such configurations.

As used herein, nucleic acids include DNA, RNA and analogs thereof, including peptide nucleic acids (PNA) and mixtures thereof. Nucleic acids can be single or double-stranded. When referring to probes or primers, which are optionally labeled, such as with a detectable label, such as a colorimetric, luminescent or chemiluminescent label, or a chromophore or a fluorophore or a radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleotides long.

As used herein, the terms "label" and "tag" are used interchangeably to refer to a marker or indicator distinguishable by the observer used to identify an analyte or target molecule. A label may achieve its effect by undergoing a pre-designed detectable process. Labels often are used in biological assays to be conjugated with, or attached to, an otherwise difficult to detect substance. At the same time, labels usually do not change or affect the underlining assay process. A label or tag used in biological assays include, but are not limited to, a radioactive material, a magnetic material, quantum dot, an enzyme, a liposome-based label, a chromophore, a fluorophore, a dye, a nanoparticle, a quantum dot or quantum well, a colloidal metal particle, or a combination thereof.

As used herein, the term "chromophore" refers to a molecule containing a chemical group that absorbs light at a specific frequency and so imparts color to a molecule.

As used herein, the term "fluorophore" refers to a molecule containing a chemical group that has luminescence that is caused by the absorption of radiation at one wavelength followed by nearly immediate re-radiation usually at a different wavelength and that ceases almost at once when the incident radiation stops. A "fluorophore" or "fluorescent compound" can include, but is not limited to, a dye, intrinsically fluorescent protein and a lanthanide phosphor. Dyes, for example, include rhodamine and derivatives, such as Texas Red, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS (5-({2-[(iodoacetyl)amino]ethyl}amino)naphthalene-1-sulfonic acid), 7-dimethyl-N-coumarin-4-acetate, 7-hydroxy-4-methylcoumarin-3-acetate, 7-$NH_2$-4-methylcoumarin-3-acetate (AMCA), monobromobimane, pyrene trisulfonates, such as Cascade Blue, and monobromotrimethyl-ammoniobimane.

As used herein, "luminescence" refers to electromagnetic radiation in the range from UV to IR radiation, and usually refers to visible electromagnetic radiation (i.e., light).

As used herein, the term "biomarker" refers to any compound or molecule, such as a protein or a fragment thereof, a peptide, a polypeptide, a proteoglycan, a glycoprotein, a lipoprotein, a carbohydrate, a lipid, a nucleic acid, an organic or inorganic molecule, a natural polymer, or a small molecule, that is present in the biological sample and that may be isolated from, or measured in, the biological sample, which is useful for measuring the initiation, progression, severity, pathology, aggressiveness, grade, activity, disability, mortality, morbidity, disease sub-classification or other underlying pathogenic or pathologic feature of one or more diseases. A biomarker also may be the target for monitoring the outcome of a therapeutic intervention (e.g., the target of a drug agent). A biomarker can be associated with a phenotype, such as a healthy phenotype or a disease phenotype.

As used herein, the term "phenotype" refers to an observable physical or biochemical characteristic of an organism, as determined by both genetic makeup and environmental influences.

As used herein, the term "healthy phenotype" refers to a biological attribute that can be associated with the normal condition, generally free of a disease state or condition. In general a healthy phenotype refers to a biological attribute that can be evaluated to infer or predict a particular characteristic of the normal condition, such as a clinical sign or diagnostic criteria of the normal condition.

As used herein, the term "disease phenotype" refers to a biological attribute that can be associated with a disease state or condition. In general a disease phenotype refers to a biological attribute that can be evaluated to infer or predict a particular characteristic of a disease state or condition, such as a clinical sign or diagnostic criteria of the disease condition. A disease phenotype can be used to diagnose diseases, to monitor disease progression, and to guide decision-making relating to treatment of diseases.

As used herein, the term "polypeptide" refers to a molecule including at least two amino acids, or amino acid derivatives, including mass modified amino acids and amino acid analogs, which are linked by a peptide bond and which can be a modified peptide bond. A polypeptide can be translated from a polynucleotide, which can include at least a portion of a coding sequence, or a portion of a nucleotide sequence that is not naturally translated due, for example, to it being located in a reading frame other than a coding frame, or it being an intron sequence, a 3' or 5' untranslated sequence, a regulatory sequence such as a promoter. A polypeptide also can be chemically synthesized and can be modified by chemical or enzymatic methods following translation or chemical synthesis. The terms "polypeptide," "peptide" and "protein" are used essentially synonymously herein, although the skilled artisan recognizes that peptides generally contain fewer than about fifty to one hundred amino acid residues, and that proteins often are obtained from a natural source and can contain, for example, post-translational modifications. A polypeptide can be post-translationally modified by, for example, phosphorylation (phosphoproteins), glycosylation (glycoproteins, proteoglycans), which can be performed in a cell or in a reaction in vitro.

As used herein, a peptide refers to a polypeptide that is from 2 to 40 amino acids in length.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain). In keeping with standard polypeptide nomenclature described in *J. Biol. Chem.*, 243: 3552-3559 (1969), and adopted 37 C.F.R. §§1.821-1.822, abbreviations for the amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | proline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | asparagines |
| B | Asx | Asn and/or Asp |
| C | Cys | Cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, a "hydrophobic amino acid" includes any one of the amino acids determined to be hydrophobic using the Eisenberg hydrophobicity consensus scale. Exemplary are the naturally occurring hydrophobic amino acids, such as isoleucine, phenylalanine, valine, leucine, tryptophan, methionine, alanine, glycine, cysteine and tyrosine (Eisenberg et al., (1982) Faraday Symp. Chem. Soc. 17:109-120). Non-naturally-occurring hydrophobic amino acids also are included.

As used herein, an "acidic amino acid" includes among the naturally-occurring amino acids aspartic acid and glutamic acid residues. Non-naturally-occurring acidic amino acids also are included.

As used herein, "naturally occurring amino acids" refer to the 20 L-amino acids that occur in polypeptides.

As used herein, "non-natural amino acid" refers to an organic compound containing an amino group and a carboxylic acid group that is not one of the naturally-occurring amino acids listed in Table 1. Non-naturally occurring amino acids thus include, for example, amino acids or analogs of amino acids other than the 20 naturally-occurring amino acids and include, but are not limited to, the D-isostereomers of amino acids. As used herein, the term "affinity tagged protein" refers to a protein in which a reactive group thereof is attached to an affinity tag, directly or through a linker.

As used herein, the term "affinity tag" refers to a moiety that binds selectively either covalently or non-covalently and with high affinity to a capture reagent. The affinity tag interaction or bond with the protein generally remains intact after extensive and multiple washings with a variety of solutions to remove non-specifically bound components. The affinity tag binds minimally or preferably not at all to other components in the biological sample, except the capture reagent, and does not significantly bind to surfaces of vessels. Any non-specific interaction of the affinity tag with other components or surfaces should be disruptable by multiple washes that leave bond between the affinity tag and the protein intact.

As used herein, the term "DNA segment" refers to a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, the term "polynucleotide" means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term "nucleotides" is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule can not be paired. Such unpaired ends will, in general, not exceed 20 nucleotides in length.

As used herein, "primary sequence" refers to the sequence of amino acid residues in a polypeptide.

As used herein, it is understood that the terms "substantially identical" or "similar" varies with the context as understood by those skilled in the relevant art, but that those of skill can assess such.

As used herein, "specifically hybridizes" refers to annealing, by complementary base-pairing, of a nucleic acid molecule (e.g., an oligonucleotide) to a target nucleic acid molecule. Those of skill in the art are familiar with in vitro and in vivo parameters that affect specific hybridization, such as length and composition of the particular molecule. Parameters particularly relevant to in vitro hybridization further include annealing and washing temperature, buffer composition and salt concentration. Exemplary washing conditions for removing non-specifically bound nucleic acid molecules at high stringency are 0.1×SSPE, 0.1% SDS, 65° C., and at medium stringency are 0.2×SSPE, 0.1% SDS, 50° C. Equivalent stringency conditions are known in the art. The skilled person can readily adjust these parameters to achieve specific hybridization of a nucleic acid molecule to a target nucleic acid molecule appropriate for a particular application. For purposes herein, when oligonucleotides are presented on a molecule to be linked to a magnetic particle that presents complementary oligonucleotides, complementarity is sufficient for affixing the molecules to the particles under conditions of mass spectrometry. Typically such hybrids are stable under stringent conditions.

As used herein, "isolated" or "purified" polypeptide or protein or biologically-active portion thereof is substantially free of cellular material or other contaminating proteins from the cell of tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as proteolytic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

As used herein, the term "substantially free of cellular material" includes preparations of proteins in which the protein is separated from cellular components of the cells from which it is isolated or recombinantly-produced. In one embodiment, the term "substantially free of cellular material" includes preparations of target proteins having less that about 30% (by dry weight) of contaminating proteins, generally less than about 20% of contaminating proteins or 10% of contaminating proteins or less that about 5% of contaminating proteins. When the target protein or active portion thereof is recombinantly produced, it also is substantially free of culture medium, i.e., culture medium represents less than, about, or equal to 20%, 10% or 5% of the volume of the target protein preparation.

As used herein, the term "substantially free of chemical precursors or other chemicals" includes preparations of target proteins in which the protein is separated from chemical precursors or other chemicals that are involved in the synthesis of the protein. The term includes preparations of target proteins having less than about 30% (by dry weight), 20%, 10%, 5% or less of chemical precursors or components.

As used herein, production by recombinant methods by using recombinant DNA methods refers to the use of the well known methods of molecular biology for expressing proteins encoded by cloned DNA.

As used herein, "derivative" or "analog" of a molecule refers to a portion derived from or a modified version of the molecule.

As used herein, a "therapeutic agent" or "therapeutic regimen" refers to conventional drugs and drug therapies, including vaccines, which are known to those skilled in the art.

As used herein, a "combination" refers to any association between two or among more items. The association can be spatial or refer to the use of the two or more items for a common purpose.

As used herein, a "composition" refers to any mixture of two or more products or compounds (e.g., agents, modulators, regulators, etc.). It can be a solution, a suspension, liquid, powder, a paste, aqueous or non-aqueous formulations or any combination thereof.

As used herein, an "article of manufacture" is a product that is made and sold. As used throughout this application, the term is intended to encompass the magnetic separator devices described herein contained in articles of packaging.

As used herein, "fluid" refers to any composition that can flow. Fluids thus encompass compositions that are in the form of semi-solids, pastes, solutions, aqueous mixtures, gels, lotions, creams and other such compositions.

As used herein, a "kit" refers to a combination in which items or components are packaged optionally with instructions for use and/or reagents and apparatus for use with the combination.

As used herein, "antibody" includes antibody fragments, such as Fab fragments, which are composed of a light chain and the variable region of a heavy chain.

As used herein, a "receptor" refers to a molecule that has an affinity for a particular ligand. Receptors can be naturally-occurring or synthetic molecules. Receptors also can be referred to in the art as anti-ligands.

As used herein, "animal" includes any animal, such as, but not limited to; primates including humans, gorillas and monkeys; rodents, such as mice and rats; fowl, such as chickens; ruminants, such as goats, cows, deer, sheep; ovine, such as pigs and other animals. Non-human animals exclude humans as the contemplated animal. The proteases provided herein are from any source, animal, plant, prokaryotic and fungal.

As used here, the singular forms "a," "an" and "the" include plural referents unless the context clearly dictates otherwise.

As used herein, ranges and amounts can be expressed as "about" a particular value or range. About also includes the exact amount. Hence "about 5 percent" means "about 5 percent" and also "5 percent." "About" means within typical experimental error for the application or purpose intended.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

As used herein, a "magnetic material" or "ferro-magnetic material" refers to any material that exhibits a magnetic force or is attracted to a magnetic force or that highly saturates in the presence of a magnetic field.

As used herein, a "non-magnetic material" or "non-ferromagnetic material" refers to any material that is either not attracted to a magnetic force, or only weakly attracted to a magnetic force, and which either does not saturate or does not highly saturate in the presence of a magnetic field. A totally non-magnetic material has a magnetic permeability of 1.

As used herein, "ferromagnetism" refers to the characteristic exhibited by certain metals, alloys, and compounds of the actinide, transition metal and rare-earth elements in which the atomic magnetic moments tend to line up in a common direction below a certain temperature. The internal magnetic moments generally are organizes in a common direction, giving rise to a magnetic permeability considerably greater than that of vacuum and to magnetic hysteresis. Ferromagnetic materials usually have some unpaired electrons so their atoms have a net magnetic moment. They exhibit a strong attraction to magnetic fields and are able to retain their magnetic properties after the external field has been removed. Substances such as cobalt, iron and nickel and alloys thereof tend to be ferromagnetic and exhibit high magnetic permeability. Ferromagnetism usually is characterized by the strong attraction of one magnetized body to another or to a magnetic material. Ferromagnetic material usually displays a high magnetic permeability, a definite saturation point, and appreciable hysteresis. As used herein, the term "ferromagnetic" is specifically meant to include materials possessing paramagnetic, ferromagnetic, and superparamagnetic properties.

As used herein, the term "paramagnetic" refers to materials having a small and positive susceptibility to magnetic fields, which are attracted by a magnetic field. Paramagnetic materials do not retain magnetic properties when the external field is removed. These paramagnetic properties are due to the presence of some unpaired electrons and the realignment of the electron orbits caused by the external magnetic field. Examples of paramagnetic materials include, but are not limited to, magnesium, molybdenum, and lithium.

As used herein, the term "magnetically permeable" refers to any material that can have a force applied to it by magnetic flux such that the material can be retained by the magnetic fields in the devices and methods of the present invention. Magnetically permeable materials include ferromagnetic and paramagnetic materials.

As used herein, "magnetic permeability" refers to a property of a substance of retaining magnetic field lines therein and, accordingly, has a dimension of Telsa meter/ampere or Newton/ampere$^2$.

As used herein, the terms "relative magnetic permeability" and "relative permeability" refer to a ratio of the "magnetic permeability" of a substance of interest to that of air and, therefore, are dimensionless properties. As used herein, the term "permeability" means the dimensionless "relative permeability" unless otherwise specified as the "magnetic permeability" with the above dimension.

As used herein, the term "very or highly permeable" means that the "permeability" is high such as, e.g., at least a few orders of magnitudes higher than that of the air. Ferromagnetic materials, such as those that include elements such as iron, cobalt, nickel, and gadolinium, and certain alloys including or based upon one or more of such elements, may be generally relatively permeable. Accordingly, the "permeabilities" of the ferromagnetic materials are very greater than 1.0, while the "permeabilities" of the paramagnetic and diamagnetic materials are respectively slightly greater than and slightly less than 1.0.

As used herein, the term "magnetic flux" or merely "flux" refers to the presence of a force field in a specified physical medium, or the flow of energy through a surface.

As used herein, the term "magnetically sensitive" refers to any material that responds to a magnetic field by being either attracted to or repelled from it.

As used herein, the term "superparamagnetic" refers to the exhibition of the property of being attracted by a magnet, and of assuming a position parallel to that of an externally applied magnetic force, but not of becoming permanently magnetized, even at temperatures below the Curie temperature or the Neel temperature. The term "paramagnetic" also is used herein essentially synonymously with, and as an abbreviation of, "superparamagnetic", although those in the art recognize the distinctions between the two.

As used herein, the term "magnetic field" refers to the region in space surrounding a magnetic body or entity, such as a permanent magnet or a conductor carrying a current, where an appreciable magnetic force is present. Such a field is represented by magnetic lines of force. In an electromagnetic field, for example, the magnetic field is perpendicular to the electrical field.

As used herein, the term "magnetic field strength" or "magnetic field intensity" ("H") refers to the intensity of a magnetic field at a given point. Magnetic field strength is a vector quantity usually expressed in amperes per meter or in oersteds.

As used herein, the term "magnetic flux density" or "magnetic induction" refers to the amount of magnetic flux through a unit area taken perpendicular to the direction of the magnetic flux.

As used herein, a "magnetizable material" refers to any material that is attracted to a magnet or that is held in place by a magnet.

As used herein, a "magnetizable plate" refers to any sheet of magnetizable material.

As used herein, the term "non-bonded magnet" refers to a magnet in which no binder is used during the process to make the bulk magnet.

As used herein, the term "bonded magnet" refers to a magnet in which binder was used during the process to make the magnet. Exemplary binders that can be used in the production of bonded magnets are epoxy, polyester, nylon, rubber, soft metals, or soft alloys. The soft metals can be selected from Sn, Zn, and combinations thereof. The soft alloys can be selected from Al—Mg, Al—Sn, Al—Zn, and combinations thereof.

As used herein, the term "high performance magnet" refers to a permanent magnet containing 10% or more percent by weight of cobalt, neodymium, samarium, or nickel. In general, a high performance magnet possesses a high maximum energy product, $(BH)_{max}$, a high remanence, Br, and a high intrinsic coercivity.

As used herein, the term "high maximum energy product" or "$(BH)_{max}$" refers to the maximum product B×H, where B is flux density expressed in Gauss (Teslas in SI units) and where H is applied magnetic field expressed in Oersteds (Ampere-Turns per centimeter in SI units). The maximum energy product is sometimes expressed in terms of $BH \times 10^6$ or Mega-Gauss-Oersted.

As used herein, the term "coercive force" refers to the amount of reverse magnetic field which must be applied to a magnetic material to make the magnetic flux return to zero.

As used herein, the term "intrinsic coercivity" or "Hci" refers to a property of the magnet that allows the magnet to withstand a demagnetizing field and is a measure of it permanence. Having a high Hci does not affect the magnet's performance in any other way other than giving it permanence. Neodymium magnets generally exhibit high intrinsic coercivities.

As used herein, the term "remnant flux density" or "residual flux" refers to the magnetic flux density that remains in a material when the magnetizing force is zero. When a material has been magnetized to its saturation point, residual flux and magnetic retentivity are the same.

As used herein, "magnetic remanence" refers to the magnetization that remains in a substance after the magnetizing force, such as an external magnetic field, has been removed.

As used herein, the term "magnetic susceptibility" refers to a difference between the "permeability" and 1. Therefore, the "magnetic susceptibilities" of the ferromagnetic materials are far greater than 0, while those of the paramagnetic and diamagnetic materials may only be slightly greater and less than 0, respectively.

As used herein, a "rare-earth magnet" refers to a magnet that includes as an element of its composition a rare earth metal, and more specifically includes any one of the 15 elements having an atomic number from number 57 to number 71 (the lanthanides: lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb) and lutetium (Lu)), and number 21 scandium (Sc) and number 29 yttrium (Y). Exemplary rare earth magnets include R—Co-based rare earth magnets and R—Fe—B-based rare earth magnets, where R represents a rare earth metal. The magnets can include other components, such as copper and zirconium, and can include inadvertent impurities. Examples of rare-earth magnets are described, e.g., in U.S. Pat. Nos. 7,442,262; 7,431,070; 7,371,292; 7,316,752; 7,285,338; 7,279,053; 7,258,751; 7,211,157; 7,172,659; 7,147,686; 7,141,126; 7,014,718; 7,048,808; 6,527,971; 6,527,874; 6,399,150. Rare-earth magnets are very powerful in proportion to size and are therefore useful in the device disclosed herein.

As used herein, a "neodymium magnet" refers to a rare-earth magnet made of a combination of neodymium, iron, and boron, including a magnet of the composition $Nd_2Fe_{14}B$.

As used herein, a "samarium-cobalt magnet" refers to a rare-earth magnet made of a combination of samarium and cobalt, including a magnet of the composition $SmCO_5$ and a magnet of the composition $Sm_2CO_{17}$.

As used herein, the "magnetic permeability" of a material refers to the quantification of the degree to which it can concentrate magnetic field lines, which can depend on the magnetic flux and temperature.

As used herein, the term "magnifer 75" refers to a soft magnetic nickel-iron alloy containing about 5% copper and 2% chromium.

As used herein, the term "conpernik" refers to an alloy containing nickel and iron with no copper.

As used herein, the term "Hiperco®" alloy refers to a soft magnetic alloy of iron, cobalt and vanadium.

As used herein, the term "Hymu 80®" alloy refers to an alloy of 80% nickel, 5% molybdenum, 0.5% silicon, 0.02% copper and iron.

As used herein, the term "hypernom" refers to an alloy containing 80% nickel, iron and molybdenum.

As used herein, the term "isoperm" refers to alloy containing 50% iron and nickel.

As used herein, the term "nilomag 36" refers to a binary alloy containing iron and 36% nickel.

As used herein, the term "nilomag 42" refers to a binary alloy containing iron and 42% nickel.

As used herein, the term "nilomag 48" refers to a binary alloy containing iron and 48% nickel.

As used herein, the term "NILO alloy K" refers to nickel-iron-cobalt alloy containing 29% nickel and 17% cobalt.

As used herein, "Permalloy" refers to an alloy that includes 4% Mo, 79% Ni, and 17% Fe.

As used herein, "Supermalloy" refers to an alloy that includes 5% Mo, 79% Ni and 16% Fe.

As used herein, "1040 alloy" refers to an alloy that includes 3% Mo, 14% Cu, 72% Ni and 11% Fe.

As used herein, "mumetal" refers to an alloy that includes 5% Cu, 2% Cr, 77% Ni and 16% Fe.

As used herein, "rhometal" refers to an alloy that includes 36% Ni and 64% Fe.

As used herein, "sinimax" refers to an alloy that includes 43% Ni, 54% Fe and 3% Si. As used herein, "monimax" refers to an alloy that includes 48% Ni, 49% Fe and 3% Mo.

As used herein, "45 permalloy" refers to an alloy that includes 45 Ni and 55% Fe.

As used herein, "CARPENTER 49 alloy" refers to an alloy that includes, 47-50% Ni and 50-53% Fe.

As used herein, each of the terms "hipernik" and "hipernik V" and "deltamax" and "48 orthonix" and "isoperm" refers to an alloy that includes 50% Ni and 50% Fe.

As used herein. "78 permalloy" refers to an alloy that includes 78% Ni and 22% Fe. Reference may be made to Chih-Wen-Chen, *Magnetism and Metallurgy of Soft Mag-*

*netic Materials* (Dover Publications, (1986), pp. 386-387) for a listing of the initial permeabilities and coercivities for these alloys.

As used herein, the term "sendust" refers to an alloy containing 85% iron, 9.6% silicon and 5.4% aluminum.

As used herein, the term "ultraviolet light" or "UV light" refers to light having a wavelength from 400 nm to about 100 nm or less but longer than x-rays. UV light from the sun has a wavelength within a range of 240 to 400 nm. UV light is classified into three zones by the wavelength range. That is, they are UV light (UV-A) having a long wavelength of 320 to 400 nm, UV light (UV-B) having a wavelength of 280 to 320 nm and UV light (UV-C) having a low wavelength of 240 to 280 nm which is absorbed in the ozone layer over the earth and scarcely reach the surface of the earth.

As used herein, the term "microfuge tube" refers to a microcentrifuge tube. Microfuge tubes generally are cylindrical plastic containers with round or conical bottoms, and often are made of polystyrene or polypropylene. They come in many different sizes, generally ranging from about 200 µL to 2.0 mL.

As used herein, a support (also referred to as a matrix support, a matrix, an insoluble support or solid support) refers to any solid or semisolid or insoluble support to which a molecule of interest, such as a capture compound, a biological molecule, organic molecule and biospecific ligand, is linked directly or indirectly via a covalent or other high affinity bond. Such materials include any materials that are used as affinity matrices or supports for chemical and biological molecule syntheses and analyses, such as, but are not limited to: polystyrene, polycarbonate, polypropylene, nylon, glass, dextran, chitin, sand, pumice, agarose, polysaccharides, dendrimers, buckyballs, polyacrylamide, silicon, rubber, and other materials used as supports for solid phase syntheses, affinity separations and purifications, hybridization reactions, immunoassays and other such applications. The matrix herein can be particulate or can be in the form of a continuous surface, such as a microtiter dish or well, a glass slide, a silicon chip, a nitrocellulose sheet, nylon mesh, or other such materials. When particulate, typically the particles have at least one dimension in the 5 10 mm range or smaller. Such particles, referred collectively herein as "beads" or "particles", are often, but not necessarily, spherical. Such reference, however, does not constrain the geometry of the matrix, which can be any shape, including random shapes, needles, fibers, and elongated. Roughly spherical "beads", particularly microspheres that can be used in the liquid phase, also are contemplated. The "beads" or "particles" can include additional components, such as magnetic or paramagnetic materials (see, e.g., Dynabeads® (Dynal, Oslo, Norway)) for separation using magnets. Such beads/particles are magnetic beads or magnetic particles.

As used herein, a "solid support" is an insoluble material to which reagents or material can be attached so that they can be readily separated from the original solution. A solid support can be a bead. In other embodiments, the solid support can be an insoluble material to which the beads are attached or associated, such as for example, by magnetic forces. For example, paramagnetic beads can be contained in a solid support such as, but not limited to, microfuge tubes, columns, or multi-well microtiter plates, to which a magnetic force is applied, such as by samarium, cobalt or neodymium magnet, thus attaching the beads to the solid support until removal of the magnetic force releases the beads. A solid support can be a flat surface constructed, for example, of glass, silicon, metal, plastic or a composite; or can be in the form of a bead such as a silica gel, a controlled pore glass, a magnetic or cellulose bead; or can be in the form of a column, such as those used in chromatography; or can be a pin, including an array of pins suitable for combinatorial synthesis or analysis.

A variety of materials can be used as the solid support. The support materials include any material that can act as a support for attachment of the molecules of interest. Such materials are known to those of skill in this art. These materials include, but are not limited to, organic or inorganic polymers, natural and synthetic polymers, including, but not limited to, agarose, cellulose, nitrocellulose, cellulose acetate, other cellulose derivatives, dextran, dextran-derivatives and dextran co-polymers, other polysaccharides, glass, silica gels, gelatin, polyvinyl pyrrolidone, rayon, nylon, polyethylene, polypropylene, polybutylene, polycarbonate, polyesters, polyamides, vinyl polymers, polyvinylalcohols, polystyrene and polystyrene copolymers, polystyrene cross-linked with divinylbenzene, acrylic resins, acrylates and acrylic acids, acrylamides, polyacrylamides, polyacrylamide blends, co-polymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, red blood cells, metals, metalloids, magnetic materials, or other commercially available media.

As used herein, matrix or support particles refers to matrix materials that are in the form of discrete particles. The particles have any shape and dimensions, but typically have at least one dimension that is 100 mm or less, 50 mm or less, 10 mm or less, 1 mm or less, 100 µm or less, 50 µm or less and typically have a size that is 100 $mm^3$ or less, 50 $mm^3$ or less, 10 $mm^3$ or less, and 1 $mm^3$ or less, 100 $µm^3$ or less and can be on the order of cubic microns. Such particles are collectively called "beads" or "particles." When combined with magnetic material or other rendered magnetic, they are referred to as magnetic bead or particles. The term "magnetic particle" or "magnetic bead" refers to a particle that is a magnet, or that is attracted by a magnet. Any particle, such as a bead, that is a magnetic particle or that can be trapped by a magnetic source, such as a magnet, is a magnetic particle. Any particle/bead can be made magnetically responsive by incorporation of a magnetic or paramagnetic substance, such as for example, magnetite, in the interior or surface of the bead. Examples of magnetic particles are ferro-, fern-, para- or superparamagnetic particles, optionally covered with natural or synthetic polymers or a solid support, and include particles, which are composed of iron or other metals such as cobalt, nickel, individually or in the form of alloys, magnetic, paramagnetic or superparamagnetic.

As used herein, the term "conjugated" refers to a stable attachment, typically by virtue of a chemical interaction, including ionic and/or covalent attachment. Among the conjugation means are streptavidin- or avidin- to biotin interaction; hydrophobic interaction; magnetic interaction (e.g., using functionalized magnetic particles, such as magnetic beads, such as DYNABEADS®, which are streptavidin-coated magnetic beads sold by Dynal, Inc. Great Neck, N.Y. and Oslo Norway); polar interactions, such as "wetting" associations between two polar surfaces or between oligo/polyethylene glycol; formation of a covalent bond, such as an amide bond, disulfide bond, thioether bond, or via crosslinking agents; and via an acid-labile or photocleavable linker.

As used herein, the term "multi-well plate" refers to a flat plate with multiple "wells" used as small test tubes. The term encompasses microtiter plates or microplates. The microtiter plate has become a standard tool for performing a large number of chemical or biological assays in parallel in applications such as analytic research, combinatorial synthesis or high throughput screenings. Multi-well plates, such as microtiter plates, typically have 96, 384 or 1536 sample wells arranged in a 2:3 rectangular matrix, although other geometries and matrix configurations are known, although any number of wells can be included. Higher density plates, such as those having 3456 or 6144 wells, are known in the art (e.g., see WO2007/138085) or can be manufactured. Depending on the number of wells on the plate, each well of a plate typically holds between a few to a few hundred microliters of liquid.

As used herein, a "lid" refers a covering that covers the opening and seals a vessel or a plug that partially fills the opening of and seals a vessel. In general, a lid includes one or a plurality of plugs or inserts projecting downwardly from the lid, which fit within the opening of vessel or the chambers of a multi-well vessel and seal the opening. The lid may be for a single vessel, such as a vial, where the lid includes a single plug projecting downwardly, where the plug fits into the opening of the vial and seals it. The lid also can be configured to cover a multi-well vessel, such as a multi-well microtiter plate, in which case the lid includes a plurality of projections aligned in an array with each other in the same pattern as the configuration of wells of a microtiter plate such that each plug of the lid enters a designated well of the microtiter plate and seals the opening of the wells of the plate.

As used herein, the term "chamber" refers to a structure that is capable of containing a fluid sample. The chamber may have various dimensions and its volume may vary, such as between about 1 microliter and 0.5 liter.

As used herein, the term "mixing" refers to the use of physical forces to cause particle movement in a sample, solution, or mixture, such that components of the sample, solution, or mixture become interspersed.

As used herein, the term "probe" or "probe molecule" refers to a molecule that interacts with a target molecule or particular reactive groups on a target molecule. The probe or probe molecule generally, but not necessarily, has a known molecular structure or sequence. The probe or probe molecule generally, but not necessarily, includes a binding moiety that enables it to attach to a solid support. The probe or probe molecule can be a synthetic molecule, such as a small molecule that includes one or a plurality of functional groups, a nucleotide, an oligonucleotide, a polynucleotide, a peptide, a protein, or a carbohydrate, such as an oligosaccharide or polysaccharide. A probe or probe molecule can be a capture molecule.

As used herein, the term "capture compound" refers to functional compounds that can bind to other molecules, by covalent or other stable bonds. These include capture compounds that include mono-functional, bi-functional, tri-functional, quadra-functional or poly-functional compounds that include one or a plurality of chemical moieties that stably interact with a molecule, such as by forming a covalent or high affinity (typically with a $k_a$ of $10^7$ or $10^8$) or sufficiently stable to withstand exposure to a mass spectroscopy laser). Capture compounds include those sold by caprotec bioanalytics GmbH (Berlin, Germany) as caprotec Capture Compound™ compounds.

The capture compounds, such as caprotec Capture Compound™ compounds can include functional groups that confer reactivity, selectivity and separative properties, depending on the specificity of separation and analysis required (which depends on the complexity of the mixture to be analyzed). For example, a capture compound can include one or a combination of a sorting function, a reactivity function, a solubility function and a variable selectivity function. Capture compounds include multifunctional synthetic small molecules that can select, covalently bind ("capture") and isolate molecules, including biomolecules, such as proteins, based on their unique surface features.

As used herein, a "sorting function" refers to a moiety that binds either covalently or noncovalently to a target molecule to permit separation or immobilization of the target molecule, such as by immobilization on a solid support, such as a magnetic particle, or separation at discrete loci on a solid support. Exemplary sorting functions include one member of a specific binding pair, where the corresponding member of the binding pair is attached to a solid support; nucleic acids or nucleic acid analogs that optionally include a single-stranded region that can specifically hybridize to a complementary single-stranded oligonucleotide or analog thereof; a ligand that specifically interacts or binds with a receptor on a solid support; or any molecule that has a cognate binding partner to which it binds with affinity. The sorting function allows the target molecule or molecule of interest, such as a specific protein, to be isolated from a reaction mixture, such as a complex cellular environment, using a solid support (e.g., magnetic bead, DNA chip), enabling subsequent structural and functional characterization of the molecule.

As used herein, a "reactivity function" refers to a moiety that specifically interacts with the molecule of interest, such as a biomolecule, such as a protein. A reactivity function generally binds to a molecule of interest, such as a biopolymer, either covalently or with a high $K_a$ (generally greater than about $10^9$, $10^{10}$, $10^{11}$ or $10^{12}$ liters/mole and/or such that the binding is substantially irreversible or stable, such as under conditions of mass spectrometric analyses, such as MALDI-MS conditions. The reactivity function includes groups that specifically react or interact with functionalities on the surface of a molecule or biomolecule, such as a protein, including hydroxyl, amine, amide, thiol, sulfide and carboxylic acid groups, or that recognize specific surface areas, such as an antibody, a lectin or a receptor-specific ligand, or interacts with the active site of enzymes.

As used herein, a "selectivity function" refers to a moiety that modulates the interaction of a target molecule, such as a biomolecule, with the reactivity function. A selectivity function, which by virtue of its interaction, usually non-covalent interaction, alters the specificity of the reactivity function, typically by increasing specificity. The selectivity functionality interacts with or "looks" at the topology of the molecule of interest around reactivity binding sites and functions to select particular groups on the molecule of interest from among those with which a reactivity group can form a covalent bond (or high affinity bond). A selectivity group can cause steric hindrance, or permit specific binding to an epitope, or anything in between. It can be a substrate for or inhibitor of an enzyme, a drug, a drug metabolite, a lipid, a peptide, an oligonucleotide or a mono- or oligosaccharide. As used herein, a "solubility function" refers to a moiety that influences the solubility of the capture compound, such as by attenuating or altering the hydrophobicity and/or hydrophilicity of the compounds. The solubility function can be selected so that the capture compounds are soluble or not soluble in a particular reaction medium or environment, such as a hydrophobic environment. For example, if membrane proteins are the targeted biomolecules, then the capture compounds can be designed to include solubility functions that increase or provide for solubility in such environment, thereby permitting reactions with membrane components.

Exemplary capture compounds are described in U.S. Pat. Nos. 6,942,974 and 7,094,943, U.S. patent application Ser. No. 10/197,954, published as US-20030119021; U.S. patent application Ser. No. 10/760,085, published as US20050042771 and republished as US20060051879; U.S. patent application Ser. No. 10/388,027, published as US20040209255; Australian Pat. No. AU 2004206856; European Pat. No. EP 1485707; European Pat. App. EP 1 583 972; and Japanese Patent No. JP 3935487; published International PCT application Nos. WO 03/092581 and WO 04/06497 and are commercially available (caprotec bioanalytics GmbH, Berlin, Germany). These capture compounds mediate a reversible affinity interaction between their specific selectivity function and target molecules, such as proteins, and the reactivity function forms a covalent bond with the interacting target molecules, such as proteins. These capture compounds include a sorting function that permits isolation of the complex formed between the probe and the protein directly out of the sample. The capture compounds optionally include a solubility function for rendering the compound soluble in particular conditions. Some capture compounds, such as caprotec Capture Compound™ compounds, which include tri-functional compounds that contain a selectivity function, which reversibly interacts with the surface of biomolecules, such as proteins via affinity interaction; a reactivity function, which can form a covalent bond or other tight bond, such as by chemical or by UV-cross-linking; and a sorting function, for isolating the captured biomolecules, such as proteins.

As used herein, the term "sample" refers to any composition, whether liquid, gas or solid, that includes a molecule or material to be detected or examined. For example, a sample can be a solution containing eukaryotic or prokaryotic cells or cellular material, or virus or viral material, or bacteria or bacterial material, or microorganisms or pathogens. A sample essentially can be water, or a buffered solution or be composed of any artificially introduced chemicals, and may or may not contain nucleic acids, amino acids or peptides. The sample can be a biological sample, such as a biological fluid or a biological tissue obtained from any organism or a cell of or from an organism or a viral particle or portions thereof.

As used herein, "biological sample" refers to any sample that includes material obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples can include biological solid material or biological fluid or a biological tissue. Examples of biological solid materials include tumors, cell pellets and biopsies. Examples of biological fluids include urine, blood, plasma, serum, sweat, saliva, semen, stool, sputum, cerebral spinal fluid, mouth wash, tears, mucus, sperm, and amniotic fluid. Biological tissues are aggregates of cells, usually of a particular kind, together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). Also included are soil, water and other environmental samples including industrial waste and natural bodies of water (lakes, streams, rivers, oceans) that can contain viruses, bacteria, fungi, algae, protozoa and components thereof. In certain embodiments, solid sample materials are mixed with a fluid.

As used herein, "MALDI-TOF" refers to matrix assisted laser desorption ionization-time of flight mass spectrometry.

As used herein, "matrix" refers to the material with which the capture compound biomolecule conjugates are combined for MALDI mass spectrometric analysis. Any matrix material, such as solid acids, including 3-hydroxypicolinic acid, liquid matrices, such as glycerol, known to those of skill in the art for nucleic acid and/or protein analyses is contemplated.

As used herein, "alkyl," "alkenyl" and "alkynyl," if not specified, contain from 1 to 20 carbon atoms, or 1 to 16 carbon atoms, and are straight or branched carbon chains. Alkenyl carbon chains are from 2 to 20 carbon atoms, and, in certain embodiments, contain 1 to 8 double bonds. Alkenyl carbon chains of 1 to 16 carbon atoms, in certain embodiments, contain 1 to 5 double bonds. Alkynyl carbon chains are from 2 to 20 carbon atoms, and, in one embodiment, contain 1 to 8 triple bonds. Alkynyl carbon chains of 2 to 16 carbon atoms, in certain embodiments, contain 1 to 5 triple bonds. Exemplary alkyl, alkenyl and alkynyl groups include, but are not limited to, methyl, ethyl, propyl, isopropyl, isobutyl, n-butyl, sec-butyl, tert-butyl, isopentyl, neopentyl, tert-penylyl and isohexyl. The alkyl, alkenyl and alkynyl groups, unless otherwise specified, can be optionally substituted, with one or more groups, including alkyl group substituents that can be the same or different.

As used herein, "lower alkyl," "lower alkenyl" and "lower alkynyl" refer to carbon chains having less than about 6 carbons.

As used herein, "alk(en)(yn)yl" refers to an alkyl group containing at least one double bond and at least one triple bond.

As used herein, an "alkyl group substituent" includes, but is not limited to, halo, haloalkyl, including halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to aromatic groups containing from 5 to 20 carbon atoms and can be a mono-, multicyclic or fused ring system. Aryl groups include, but are not limited to, phenyl, naphthyl, biphenyl, fluorenyl and others that can be unsubstituted or are substituted with one or more substituents. The term "aryl" also refers to aryl-containing groups, including, but not limited to, aryloxy, arylthio, arylcarbonyl and arylamino groups.

As used herein, an "aryl group substituent" includes, but is not limited to, alkyl, alkenyl, alkynyl, cycloalkyl, cycloalkylalkyl, aryl, heteroaryl optionally substituted with 1 or more, including 1 to 3, substituents selected from halo, halo alkyl and alkyl, aralkyl, heteroaralkyl, alkenyl containing 1 to 2 double bonds, alkynyl containing 1 to 2 triple bonds, alk(en)(yn)yl groups, halo, pseudohalo, cyano, hydroxy, haloalkyl and polyhaloalkyl, including halo lower alkyl, especially trifluoromethyl, formyl, alkylcarbonyl, arylcarbonyl that is optionally substituted with 1 or more, including 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, aralkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl.

As used herein, "aralkyl" refers to an alkyl group in that one of the hydrogen atoms of the alkyl is replaced by an aryl group.

As used herein, "heteroaralkyl" refers to an alkyl group in that one of the hydrogen atoms of the alkyl is replaced by a heteroaryl group.

As used herein, "cycloalkyl" refers to a saturated mono- or multicyclic ring system, in one embodiment, of 3 to 10 carbon atoms, or 3 to 6 carbon atoms; cycloalkenyl and cycloalkynyl refer to mono- or multicyclic ring systems that respectively include at least one double bond and at least one triple bond. Cycloalkenyl and cycloalkynyl groups can contain, in one embodiment, 3 to 10 carbon atoms, with cycloalkenyl groups, in other embodiments, containing 4 to 7 carbon atoms and cycloalkynyl groups, in some embodiments, containing 8 to 10 carbon atoms. The ring systems of the cycloalkyl, cycloalkenyl and cycloalkynyl groups can be composed of one ring or two or more rings that can be joined together in a fused, bridged or spiro-connected fashion, and can be optionally substituted with one or more alkyl group substituents. "Cycloalk(en)(yn)yl" refers to a cycloalkyl group containing at least one double bond and at least one triple bond.

As used herein, "heteroaryl" refers to a monocyclic or multicyclic ring system, in one embodiment of about 5 to about 15 members where one or more, or 1 to 3, of the atoms in the ring system is a heteroatom, which is, an element other than carbon, for example, nitrogen, oxygen and sulfur atoms. The heteroaryl can be optionally substituted with one or more, including 1 to 3, aryl group substituents. The heteroaryl group can be optionally fused to a benzene ring. Exemplary heteroaryl groups include, but are not limited to, pyrroles, porphyrines, furans, thiophenes, selenophenes, pyrazoles, imidazoles, triazoles, tetrazoles, oxazoles, oxadiazoles, thiazoles, thiadiazoles, indoles, carbazoles, benzofurans, benzothiophenes, indazoles, benzimidazoles, benzotriazoles, benzoxatriazoles, benzothiazoles, benzoselenozoles, benzothiadiazoles, benzoselenadiazoles, purines, pyridines, pyridazines, pyrimidines, pyrazines, pyrazines, triazines, quinolines, acridines, isoquinolines, cinnolines, phthalazines, quinazolines, quinoxalines, phenazines, phenanthrolines, imidazinyl, pyrrolidinyl, pyrimidinyl, tetrazolyl, thienyl, pyridyl, pyrrolyl, N-methylpyrrolyl, quinolinyl and isoquinolinyl.

As used herein, "heteroaryl" also refers to heteroaryl-containing groups, including, but not limited to, heteroaryloxy, heteroarylthio, heteroarylcarbonyl and heteroarylamino.

As used herein, "heterocyclic" refers to a monocyclic or multicyclic ring system, in one embodiment of 3 to 10 members, in another embodiment 4 to 7 members, including 5 to 6 members, where one or more, including 1 to 3 of the atoms in the ring system is a heteroatom, which is, an element other than carbon, for example, nitrogen, oxygen and sulfur atoms. The heterocycle can be optionally substituted with one or more, or 1 to 3 aryl group substituents. In certain embodiments, substituents of the heterocyclic group include hydroxy, amino, alkoxy containing 1 to 4 carbon atoms, halo lower alkyl, including trihalomethyl, such as trifluoromethyl, and halogen. As used herein, the term heterocycle can include reference to heteroaryl.

As used herein, the nomenclature alkyl, alkoxy, carbonyl, etc., are used as is generally understood by those of skill in this art. For example, as used herein alkyl refers to saturated carbon chains that contain one or more carbons; the chains can be straight or branched or include cyclic portions or be cyclic.

Where the number of any given substituent is not specified (e.g., "haloalkyl"), there can be one or more substituents present. For example, "haloalkyl" can include one or more of the same or different halogens. As another example, "$C_1$-₃alkoxyphenyl" can include one or more of the same or different alkoxy groups containing one, two or three carbons.

Where named substituents such as carboxy or substituents represented by variables such as W are separately enclosed in parentheses, yet possess no subscript outside the parentheses indicating numerical value and that follow substituents not in parentheses, e.g., "$C_{1-4}$alkyl(W)(carboxy)," "W" and "carboxy" are each directly attached to $C_{1-4}$alkyl.

As used herein, "halogen" or "halide" refers to F, Cl, Br or I.

As used herein, "pseudohalide" refers to a compound that behaves substantially similar to halides. Such compounds can be used in the same manner and treated in the same manner as halides (X, in that X is a halogen, such as Cl or Br). Pseudohalides include, but are not limited to, cyanide, cyanate, isocyanate, thiocyanate, isothiocyanate, selenocyanate, trifluoromethoxy, and azide.

As used herein, "haloalkyl" refers to a lower alkyl radical in that one or more of the hydrogen atoms are replaced by halogen including, but not limited to, chloromethyl, trifluoromethyl, 1-chloro-2-fluoroethyl and the like.

As used herein, "haloalkoxy" refers to RO in that R is a haloalkyl group.

As used herein, "sulfinyl" or "thionyl" refers to S(O). As used herein, "sulfonyl" or "sulfuryl" refers to $S(O)_2$. As used herein, "sulfo" refers to $S(O)_2O$.

As used herein, "carboxy" refers to a divalent radical, C(O)O.

As used herein, "aminocarbonyl" refers to $C(O)NH_2$.

As used herein, "alkylaminocarbonyl" refers to C(O)NHR in that R is hydrogen or alkyl, including lower alkyl.

As used herein "dialkylaminocarbonyl" as used herein refers to C(O)NR'R in that R' and R are independently selected from hydrogen or alkyl, including lower alkyl.

As used herein, "carboxamide" refers to groups of formula NR'COR.

As used herein, "diarylaminocarbonyl" refers to C(O)NRR' in that R and R' are independently selected from aryl, including lower aryl, such as phenyl.

As used herein, "aralkylaminocarbonyl" refers to C(O)NRR' in that one of R and R' is aryl, including lower aryl, such as phenyl, and the other of R and R' is alkyl, including lower alkyl.

As used herein, "arylaminocarbonyl" refers to C(O)NHR in that R is aryl, including lower aryl, such as phenyl.

As used herein, "alkoxycarbonyl" refers to C(O)OR in that R is alkyl, including lower alkyl.

As used herein, "aryloxycarbonyl" refers to C(O)OR in that R is aryl, including lower aryl, such as phenyl.

As used herein, "alkoxy" and "alkylthio" refer to RO and RS, in that R is alkyl, including lower alkyl.

As used herein, "aryloxy" and "arylthio" refer to RO and RS, in that R is aryl, including lower aryl, such as phenyl.

As used herein, "alkylene" refers to a straight, branched or cyclic, in one embodiment straight or branched, divalent aliphatic hydrocarbon group, in certain embodiments having from 1 to about 20 carbon atoms, in other embodiments 1 to 12 carbons, including lower alkylene. The alkylene group is optionally substituted with one or more "alkyl group substituents." There can be optionally inserted along the alkylene group one or more oxygen, sulphur or substituted or unsubstituted nitrogen atoms, where the nitrogen substituent is alkyl as previously described. Exemplary alkylene groups include methylene ($CH_2$), ethylene ($CH_2CH_2$), propylene (—$(CH_2)_3$), cyclohexylene ($C_6H_{10}$), methylenedioxy ($OCH_2O$) and ethylenedioxy ($O(CH_2)_2O$). The term "lower alkylene" refers to alkylene groups having 1 to 6 carbons. In certain embodiments, alkylene groups are lower alkylene, including alkylene of 1 to 3 carbon atoms.

As used herein, "alkenylene" refers to a straight, branched or cyclic, in one embodiment straight or branched, aliphatic hydrocarbon group, in certain embodiments having from 2 to about 20 carbon atoms and at least one double bond, in other embodiments 1 to 12 carbons, including lower alkenylene. The alkenylene group is optionally substituted with one or more "alkyl group substituents." There can be optionally inserted along the alkenylene group one or more oxygen, sulphur or substituted or unsubstituted nitrogen atoms, where the nitrogen substituent is alkyl as previously described. Exemplary alkenylene groups include —CH═CH— CH═CH— and CH═CHCH$_2$. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in one embodiment straight or branched, divalent aliphatic hydrocarbon group, in certain embodiments having from 2 to about 20 carbon atoms and at least one triple bond, in other embodiments 1 to 12 carbons, including lower alkynylene. The alkynylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, C≡C and C≡C—CH$_2$. The term "lower alkynylene" refers to alkynylene groups having 2 to 6 carbons. In certain embodiments, alkynylene groups are lower alkynylene, including alkynylene of 3 to 4 carbon atoms.

As used herein, "arylene" refers to a monocyclic or polycyclic, in one embodiment monocyclic, divalent aromatic group, in certain embodiments having from 5 to about 20 carbon atoms and at least one aromatic ring, in other embodiments 5 to 12 carbons, including lower arylene. The arylene group is optionally substituted with one or more "alkyl group substituents." There can be optionally inserted around the arylene group one or more oxygen, sulphur or substituted or unsubstituted nitrogen atoms, where the nitrogen substituent is alkyl as previously described. Exemplary arylene groups include 1,2, 1,3- and 1,4-phenylene. The term "lower arylene" refers to arylene groups having 5 or 6 carbons. In certain embodiments, arylene groups are lower arylene.

As used herein, "heteroarylene" refers to a divalent monocyclic or multicyclic ring system, in one embodiment of about 5 to about 15 members where one or more, or 1 to 3 of the atoms in the ring system is a heteroatom, which is, an element other than carbon, for example, nitrogen, oxygen and sulfur atoms. The heteroarylene group can be optionally substituted with one or more, or 1 to 3, aryl group substituents.

As used herein, "alkylidene" refers to a divalent group, such as ═CR'R", which is attached to one atom of another group, forming a double bond. Exemplary alkylidene groups are methylidene (═CH$_2$) and ethylidene (═CHCH$_3$). As used herein, "aralkylidene" refers to an alkylidene group in that either R' or R" is and aryl group.

As used herein, "amido" refers to the divalent group C(O)NH. "Thioamido" refers to the divalent group C(S)NH. "Oxyamido" refers to the divalent group OC(O)NH. "Thiaamido" refers to the divalent group SC(O)NH. "Dithiaamido" refers to the divalent group SC(S)NH. "Ureido" refers to the divalent group HNC(O)NH. "Thioureido" refers to the divalent group HNC(S)NH.

As used herein, "semicarbazide" refers to NHC(O)NHNH. "Carbazate" refers to the divalent group OC(O)NHNH. "Isothiocarbazate" refers to the divalent group SC(O)NHNH. "Thiocarbazate" refers to the divalent group OC(S)NHNH. "Sulfonylhydrazide" refers to the group SO$_2$NHNH. "Hydrazide" refers to the divalent group C(O)NHNH. "Azo" refers to the divalent group N═N. "Hydrazinyl" refers to the divalent group NHNH.

As used herein, the term "amino acid" refers to α-amino acids that are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dl-Ala) refers to a mixture of the L- and D-isomers of the amino acid.

As used herein, when any particular group, such as phenyl or pyridyl, is specified, this means that the group is unsubstituted or is substituted. Substituents where not specified are halo, halo lower alkyl, and lower alkyl.

As used herein, the term "adhesive" refers to a material, by means of which any two components can be attached to each other. Properties of an adhesive is that it can be spread on the surface of the component in a relatively fluid form, or otherwise in a form that will conform to the shape of the surface of the component, such as a magnet. Another property of the adhesive is that, after spreading, the adhesive hardens, or can be hardened, at least partly, so that the adhesive will be able to hold the component in place (e.g., the magnet to the sheath). Another property of the adhesive is its ability to stick to the surface being joined together. Exemplary adhesives include, but are not limited to, hot melt adhesives, thermoplastic adhesives, waterborne adhesives, solvent borne adhesives, contact adhesives, moisture curable adhesives, ultraviolet curable adhesives, urethane adhesives, blocked urethane systems, epoxy based adhesives, adhesives comprising an encapsulated cureative, polyurethane adhesives, polyurethane reactive (PUR) adhesives, plastic adhesives, acrylic adhesives, nitrocellulose adhesives, isocyanate adhesives, cyanoacrylate adhesives, caulk, rubber cement, glue, gum, paste, putty, sealant and solvents that can used to bond, join or seal plastics.

As used herein, conformationally altered protein disease (or a disease of protein aggregation) refers to diseases associated with a protein or polypeptide that has a disease-associated conformation. The methods and collections provided herein permit detection of a conformer associated with a disease to be detected. Diseases and associated proteins that exhibit two or more different conformations in which at least one conformation is a conformationally altered protein include, but are not limited to, amyloid diseases and other neurodegenerative diseases known to those of skill in the art and set forth below.

A. Isolation of Target Molecules

A common problem in life science research is the presence of highly abundant proteins, which make it difficult, if not impossible, to analyze other cellular components such as proteins of lower abundance. Current depletion procedures have the drawback that many interesting and important proteins are lost due to non-specific binding or biochemically relevant association to the high abundant proteins. This results in a dramatic reduction of efficiency in the isolation of low abundant proteins. Potential losses of any other proteins ideally should be minimized during the depletion process. To address this concern, the proteins of interest are isolated through affinity interactions out of the complex mixture. For example, immune precipitation can be used to isolate selective proteins via antibodies bound to Sepharose beads in a so-called pull-down (PD) procedure. The drawback of this methodology is that weak interacting proteins may be washed off of the beads. In addition, the Sepharose beads need to be collected at the bottom of the reaction vials by centrifugation. Removal of the reaction mixture typically takes place by a pipetting procedure. This either removes some Sepharose beads with bound proteins or leaves the beads still contaminated with some of the remaining reaction mixture. In order to avoid centrifugation, the use of magnetic beads was introduced.

The targeted analysis of molecules, especially biomolecules, is of high importance. A common method to isolate biomolecules is to use affinity based systems, such as antibodies or systems that use specific binding pairs, such as biotin-streptavidin. For example, a common application of this principle is the isolation of biotinylated nucleic acids from polymerase chain reaction mixtures. In this application, a biotinylated primer is used in a polymerases chain reaction, single stranded molecules are digested with nucleases to remove left over primers and amplified double stranded biotinylated nucleic acid molecules are contacted with streptavidin-coated magnetic beads. The biotin-streptavidin interaction can be used to pull the nucleic acids out of the reaction mixture via streptavidin that is immobilized on a magnetic solid support (e.g., particles such as beads). This principle is used for many different applications in molecular biology (e.g., specific ligand-protein interactions, isolation of peptides and proteins, etc.).

Commercially available magnetic separation devices include, for example, Dynabeads® by Dynal/Invitrogen and MagnetoPURE from Chemicell (Berlin, Germany). In these devices, a magnetic field pulls the molecules of interest, such as tagged biomolecules, or magnetic particles to which the molecules of interest are attached, towards the bottom or the side of the reaction vial and holds them in place while the supernatant is manipulated. Molecules that are not of interest, such as untagged biomolecules and other components of the reaction mixture in the supernatant, are removed with a manual pipette or an automated liquid handling system. To remove untagged material as completely as possible during the wash procedure, the magnetic particles remain in the same reaction vial. There are several important disadvantages of this methodology. For example, during the pipetting step, the supernatant cannot be removed completely in order to avoid removing magnetic beads with the attached biomolecules of interest at the same time. The beads therefore remain contaminated during the wash procedure. Many washing steps are necessary to remove most of the contamination. Due to the many necessary washing/pipetting steps, an unavoidable loss of magnetic beads carrying the biomolecules of interest occurs. Another issue is a significant adhesion of the magnetic beads to the wall of the reaction vial, which also results in reduced yields of tagged biomolecules of interest.

Other methods for separating magnetic beads from a reaction mixture include the use of an array of electromagnets specifically configured to project into the reaction mixture in a vessel (e.g., see U.S. Pat. No. 6,716,580). When the electromagnets are activated, the beads are attracted to them. By then withdrawing the activated array of electromagnets from the vessels, the beads can be removed from the vessel. A problem with this approach is that a specific number and configuration of electromagnets, with their accompanying electrical connections, is required for each type of vessel, such as vials, tube, or multi-well plates, e.g., microtiter plates, and the electromagnets must be individually configured to fit within the vessel so that they can project into the reaction mixture. Thus, multiple sizes and shapes and arrays of electromagnets must be readily available or manufactured for different applications. For example, a standard microtiter plate with 96 chambers would require 96 individual electromagnetics specifically manufactured so that each individual magnet is of a size that projects into each individual well of the plate, and configured into an array corresponding to the array of wells in the plate. Further, the electrical connections (i.e., wires, connects, etc.) that allow activation of the electromagnets must be configured to allow activation of each separate electromagnet. The cost of producing such arrays of electromagnets and creating separate arrays for different types of vessels are very high.

Accordingly, a need exists for a method for removing from a reaction mixture or biological sample magnetic particles to which are attached molecules of interest, such as biomolecules where the device allows for complete or substantially complete removal of any contaminating supernatant of a complex biological sample or reaction mixture, preventing at the same time the loss of magnetic particles carrying the biomolecule of interest, and devices for implementing the methods. The methods and devices provided herein avoid steps that reduce yield and/or efficiency, laborious pipetting and the methods and devices reduce or eliminate loss of magnetic beads.

Provided herein are methods and devices for separating magnetic particles with linked molecules. In the methods, removable sheaths that include one or more magnets are provided at the top of the vessels that contain the magnetic particles to remove the magnetic particles from the reaction mixture. The devices are configured to so-provide the sheaths with one or more magnets.

The methods and magnetic separation devices provided herein prevent or minimize loss of magnetic beads. The methods and magnetic separation devices provided herein allow for the concurrent processing of multiple vials of reaction mixtures. The methods and magnetic separation devices provided herein allow for the separation of molecules of interest, such as biomolecules, e.g., proteins or nucleic acid molecules, from supernatant or a sample or reaction mixture without the need for pipetting steps.

The magnetic separation devices provided herein allow separation of magnetic particles from a solution or reaction mixture and are easily adaptable for any type or configuration of vessel(s). The devices provided herein are not dependent on any particular type or configuration of magnet. The devices provided herein include a sheath with an embedded magnet that optionally is easily removable. The sheath includes one or more orienting pins that orient and concentrate the magnetic field of the attached magnet and orient the magnetic field to the lid of each vessel or vial. The orienting pins in the sheath can be configured and are adaptable for any configuration of vessels. In some embodiments, different sheaths interchangeably can be used with a removable magnet to accommodate different vessel configurations.

C. Device Description

Figure 1:
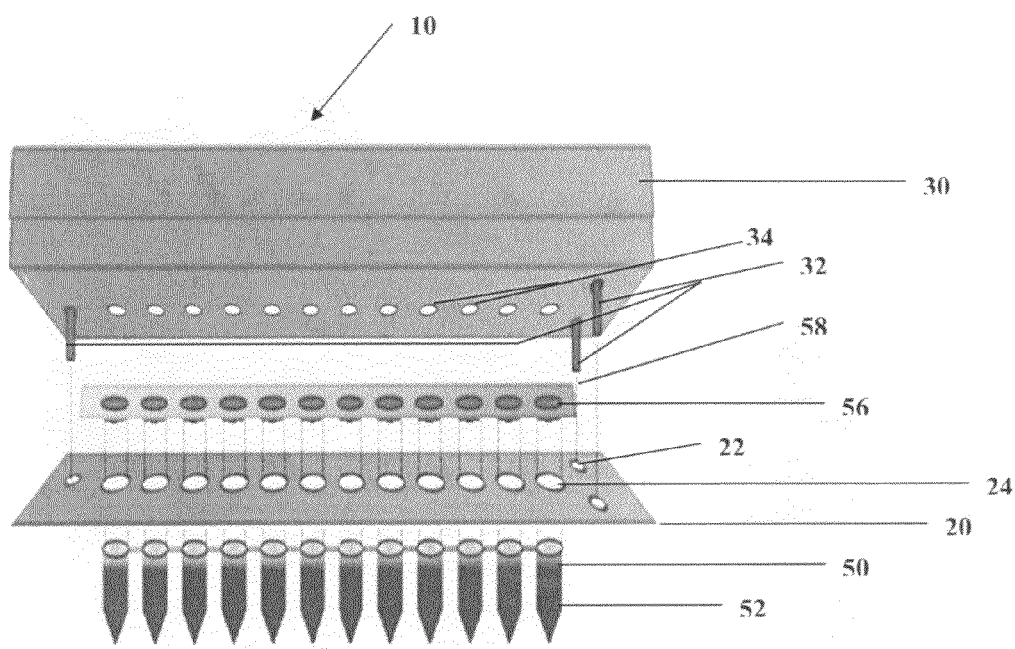
FIG. 1 is an exploded perspective view of one embodiment of a magnetic separation device of the present disclosure.

Provided herein are magnetic separator devices for separating magnetic particles from a reaction mixture. The device includes a sheath containing a magnet and a magnetizable plate. The magnetizable plate is configured to receive the sheath and is configured to receive vessel lid(s), and when the vessel lid(s) is/are engaged with the vessel(s)s, the magnetizable plate is fixed between the vessel lid(s) and the vessel(s). The sheath can include one or more orienting pins that concentrate a magnetic field of the magnet. The magnetizable plate is configured to position the orienting pin(s) over the vessel lid(s). In one embodiment, the magnetic separation device provided herein includes a magnet imbedded in a sheath containing integrated orienting pins that concentrate the magnetic field of the magnet, and a magnetizable plate for accepting lid(s) of vessel(s)s, where the magnetizable plate orients the vessel lids in a manner such that the orienting pins of the sheath direct or orient the magnetic fields of the magnet towards the lids of the vessels to separate target molecules from a reaction mixture in a vessel. The orienting pins allow the concentrated collection of magnetic particles essentially or exactly in the middle of the lid(s). With the magnetic particles collected and retained in the lid(s) of the vessel(s), the vessel(s) can be removed and discarded and replaced with new vessels free of any contaminating solutions, solvents and/or reactants. Many other configurations of the device can be envisioned by those skilled in the art, i.e. the magnet does not need to be embedded in the sheath but could be directly attached to the magnetizable plate to position the orienting pins over the vessel lids. An exemplary device is depicted in FIG. 1 and described in Example 1.

1. Magnet

The magnetic separator device provided herein includes a magnet or a plurality of magnets. The magnet used in the devices provided herein, for example, can be a permanent magnet or "hard" magnetic or made of such permanent magnetic materials that have residual induction (remanence) or can be an electromagnet. Exemplary permanent magnetic materials include alnico magnets, ferrite magnets and rare-earth magnets. In some embodiments, the magnet is a high performance magnet.

In some embodiments, the magnet is a rare-earth magnet. Examples of rare earth magnets that can be used in the disclosed device include R—Co-based rare earth magnets and R—Fe—B-based rare earth magnets, where R represents a rare earth metal, such as lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu)), scandium (Sc) and yttrium (Y). In order to improve the magnetic properties, additive elements such as C, Al, Si, Ti, V, Cr, Mn, Co, Ni, Cu, Zn, Ga, Zr, Nb, Mo, Ag, Sn, Hf, Ta and W are often added to R—Fe—B-based rare earth magnets. In some embodiments, the rare-earth magnet is selected from among a neodymium magnet and a samarium-cobalt magnet. The shape of the rare-earth magnet is not limited, and any desired shape can be used, such as cubic, rectangular, thin film, columnar, cylindrical and fan-shaped magnets. Rare earth magnets are commercially available (e.g., from any of the following suppliers: Dura Magnetics, Inc., Sylvania, Ohio; K&J Magnetics, Inc., Jamison, Pa.; Millennium Magnetics Limited, Hong Kong; One Magnet Electronic Co., Ltd, Fujian, China; and Newland Magnetics Co. Ltd, Zhejiang, China).

The magnet may be in any suitable form, such as ribbons, film, ingots, bars, sheets, discs, rods, cylinders, quadrangles, squares, cubes, circles or spheres and can be a bulk, bonded, and/or non-bonded magnet. In one embodiment, the magnet is a bonded magnet. In one embodiment, the magnet is a non-bonded magnet.

The magnet can be embedded into the sheath during fabrication of the sheath, such as by crimping of the material from which the sheath is made onto the magnet or by direct casting of the sheath onto the magnet, and/or the magnet can be held in place in the sheath, e.g., by threads, friction fit, snap fit, adhesive bonding, welding, mechanical clips, or by any other desired method.

The magnet used in the separator device provided herein can have a maximum energy product $(BH)_{max}$ of at least 3 Mega Gauss-Oersted (MGOe)s. In some embodiments, the magnet has a $(BH)_{max}$ of from about 5 MGOe or 5 MGOe to about 50 MGOe or 50 MGOe. In some embodiments, the magnet has a $(BH)_{max}$ of at least 25 MGOe. In some embodiments, the magnet has a $(BH)_{max}$ of from about 25 MGOe up to about 90 MGOe. In some embodiments, the magnet has a $(BH)_{max}$ of from about 25 MGOe up to about 50 MGOe. In some embodiments, the magnet has a $(BH)_{max}$ of about 30 MGOe to about 80 MGOe. In some embodiments, the magnet has a $(BH)_{max}$ of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 MGOe. Exemplary maximum energy product $(BH)_{max}$ values of magnets that can be used in the device provided herein include 3-5 Mega Gauss-Oersted (MGOe)s for a barium ferrite magnet, 15-20 MGOe for a cesium cobalt magnet, 20-25 MGOe for a samarium cobalt magnet and 26-40 MGOe for Neodymium-Iron-Boron magnets.

In some embodiments, the magnet has a remanence from about 3 kG to about 20 kG. In some embodiments, the magnet has a remanence from about 5 kG to about 15 kG. In some embodiments, the magnet has a remanence from about 8 kG to about 10 kG. In some embodiments, the magnet has a remanence from about 11 kG up to about 18 kG. In some embodiments, the magnet has a remanence of 3, 4, 5, 6, 7, 8, 9, 10, 11, 12, 13, 14, 15, 16, 17, 18, 19 or 20 kG.

The magnet used in the magnetic separator devices provided herein can have intrinsic coercivity between about or at 5 kOe and about or at 30 kOe. In some embodiments, the intrinsic coercivity of the magnet is greater than 5 kOe. In some embodiments, the intrinsic coercivity of the magnet is greater than 10 kOe. In some embodiments, the intrinsic coercivity of the magnet is greater than 15 kOe. In some embodiments, the intrinsic coercivity of the magnet is greater than 20 kOe. In some embodiments, the intrinsic coercivity of the magnet is greater than 25 kOe. In some embodiments, the intrinsic coercivity of the magnet is greater than 30 kOe. In some embodiments, the intrinsic coercivity of the magnet is 5, 6, 7, 8, 9, 10, 11, 12, 13, 14, 15, 16, 17, 18, 19, 20, 21, 22, 23, 24, 25, 26, 27, 28, 29, or 30 kOe.

2. Sheath

Figure 3A:
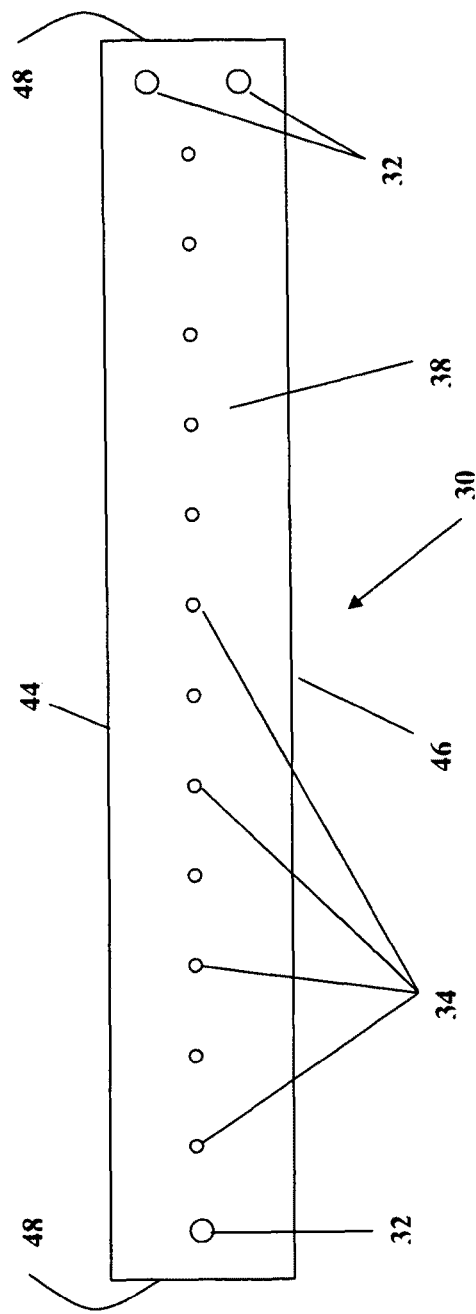
FIG. 3A is a bottom view of a sheath embodiment of the device of FIG. 1.
Figure 3B:
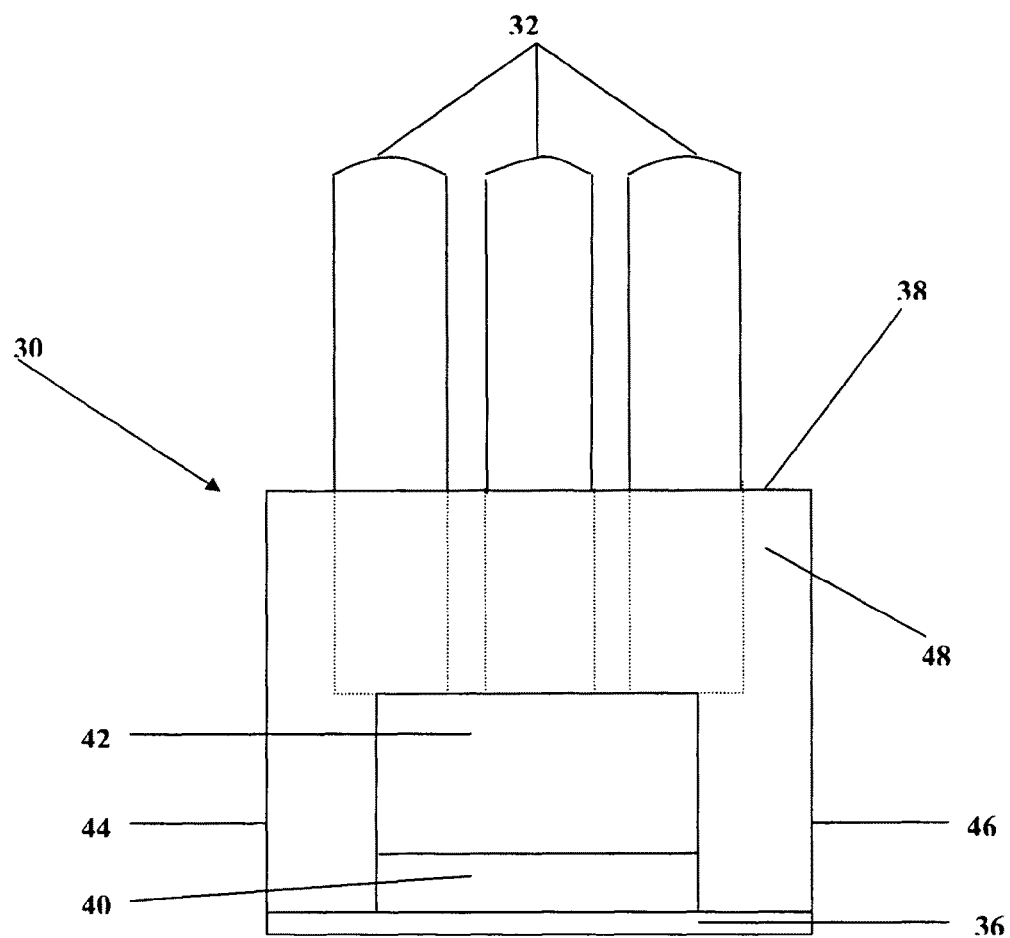
FIG. 3B is a side view of a sheath embodiment of the device of FIG. 1.

The magnetic separator device provided herein includes a sheath containing the orienting pins and in which the magnet is embedded or encased or otherwise attached. For example, the magnet can be attached/glued/screwed to the bottom face 38 of sheath 30 containing the orienting pins 34 (FIGS. 3A and 3B). Sheath 30 may only contain the bottom face 38 containing the orienting pins 34 and may lack any of the other walls or faces (front wall 44, rear wall 46, side walls 48, top face 36). An exemplary depiction of this is shown in FIG. 1 (sheath 30). The sheath is designed to contain the orienting pins and accept and hold the magnet. In some embodiments, the magnet is attached/glued/screwed to the bottom face 38 of sheath 30 containing the orienting pins 34 (FIGS. 3A and 3B) and sheath 30 only contains the bottom face 38 containing the orienting pins 34 and lacks any of the other walls or faces. In some embodiments, the magnet is embedded in the sheath. In some embodiments, the magnet is encased by the sheath. In some embodiments, the magnet is within a cavity of the sheath. In some embodiments, the magnet fills a cavity of the sheath. The magnet can be attached/glued/screwed to or embedded into the sheath during fabrication of the sheath. In some embodiments, the magnet is embedded in the sheath by crimping of the material from which the sheath is made onto the magnet. In some embodiments the magnet is encased in the sheath by direct casting of the sheath onto the magnet. In some embodiments, the magnet can be held in place in the sheath, e.g., by threads, friction fit, snap fit, adhesive bonding, welding, mechanical clips, or by any other desired method.

In some embodiments, as illustrated in side-view FIG. 3B, sheath 30 includes a bottom and at least two sides that define a cavity sized to receive one or more than one magnet. In some embodiments, the sheath has a cavity formed between a top face, a bottom face, a front wall, a rear wall and side walls, where the cavity is sized to receive one or more than one magnet. The magnet can be retained in the cavity of the sheath by any desired method. In some embodiments, the magnet is retained in the sheath by crimping of the material from which the sheath is made onto the magnet. In some embodiments, the magnet is retained in the sheath by threads, friction fit, snap fit, adhesive bonding, welding or mechanical clips. In some embodiments, the sheath optionally includes a removable top that covers the cavity and that allows the sheath to encase totally the magnet. The removable top allows the insertion and removal of the one or more than one magnet as necessary.

The sheath is made of a non-magnetic material. In some embodiments, the sheath is of a material having a permeability of about 1. In some embodiments, the sheath is made of a non-magnetic plastic. In some embodiments, the sheath is made of a non-magnetic alloy. In some embodiments, the non-magnetic alloy contains copper, aluminum, chromium, zirconium, tungsten, magnesium, manganese, silicon or beryllium. In some embodiments, the sheath is made of aluminum or aluminum alloy. Examples of aluminum alloys that can be used include those made of aluminum-copper, aluminum-magnesium, aluminum-manganese, aluminum-silicon, aluminum-magnesium-silicon and aluminum-zinc based aluminum alloys.

The shape of the sheath is not limited, and can be selected from shapes such as quadrangular, rectangular, square, cubic, columnar and cylindrical shapes, depending on the shape of the magnet and the configuration of the vessels. The sheath can be matched to be of the same shape as the shape of the magnet but it is not required that the sheath be of the same shape as the embedded or encased magnet. The sheath generally is of the same configuration as the magnetizable sheet, discussed below. For example, if the magnetizable sheet is rectangular, the sheath generally is rectangular, but can include embedded therein a magnet that is circular, cylindrical or quadrangular, or multiple quadrangular, circular or cylindrical magnets can be used to occupy the full length of the sheath.

In some embodiments, the sheath includes only a bottom face containing the orienting pins to which the magnet is attached/glued/screwed. In some embodiments, the sheath includes a bottom and at least one side wall to receive a magnet. In some embodiments, the sheath includes a bottom and at least two side walls that define a cavity to receive a magnet. In some embodiments, the sheath includes a bottom, a front wall and a back wall that define a cavity to receive a magnet, such as through an open top. In some embodiments, the sheath includes a bottom face, a front wall, a rear wall and one or two side walls that define a cavity to receive a magnet. In some embodiments, the sheath includes a closed top that is removable to expose the cavity. The bottom of the sheath includes one or more than one orienting pin.

The thickness of the bottom, front wall, back wall, side walls and optional top is not limited and need not be of uniform thickness. In some embodiments, the front, back and side walls of the sheath each independently is of a thickness different from the thickness of the bottom of the sheath. In some embodiments, the front, back and side walls of the sheath each is the same thickness as the thickness of the bottom of the sheath. In some embodiments, the removable top, when present, is of a thickness the same as any one of the front, back and side walls of the sheath. In some embodiments, the bottom, front, back and side walls of the sheath each independently is of a thickness selected from 0.1 to 100 mm. In some embodiments, the bottom, front, back and side walls of the sheath each independently is of a thickness selected from 0.25 to 50 mm. In some embodiments, the bottom, front, back and side walls of the sheath each independently is of a thickness selected from 0.5 to 25 mm. In some embodiments, the bottom, front, back and side walls of the sheath each independently is of a thickness selected from 0.5 to 10 mm, and independently can be selected from among 0.5, 1, 1.5, 2, 2.5, 3, 3.5, 4, 4.5, 5, 5.5, 6, 6.5, 7, 7.5, 8, 8.5, 9, 9.5 or 10 mm. In some embodiments, the thickness of the bottom of the sheath is from 0.5 to 10 mm, and can be selected from 0.5, 1, 2, 3, 4, 5, 6, 7, 8, 9 or 10 mm. In some embodiments, the thickness of the front, back and side walls of the sheath each independently is of a thickness selected from among 1, 1.5, 2, 2.5, 3, 3.5, 4, 4.5 or 5 mm and the thickness of the bottom of the sheath is 1, 1.5, 2, 2.5, 3, 3.5, 4, 4.5, 5, 5.5, 6, 6.5, 7, 7.5, 8, 8.5, 9, 9.5 or 10 mm. In some embodiments, the thickness of the front wall and back wall each is 3 mm and the thickness of the bottom of the sheath is 6 mm.

3. Orienting Pins

The sheath contains pins that orient and concentrate the magnetic field. The orienting pins can be of any configuration or geometry, including but not limited to cylindrical, square peg and star-shaped peg. The orienting pins can be of any shape. Exemplary shapes include parallelepiped including cuboid or cubus, block, ovoid, prism, antiprism, cylinder, ellipsoid, sphere, torus, cone, pyramid, obelisk, or truncated forms like truncated cone, frustum or any other polyhedron. The orienting pins can traverse the thickness of the bottom of the sheath. For example, if the thickness of the bottom of the sheath is 6 mm, then the length of the orienting pins can be 6 mm or longer. The orienting pins can also partly traverse the thickness of the bottom of the sheath. Then the orienting pins are hidden by one or both faces inside the bottom of the sheath. The orienting pins are arranged to concentrate magnetic field flowing in one or more directions from the magnet and orient the magnetic field to the lid of each vessel or vial. An exemplary depiction of this is shown in FIG. 1 (orienting pins 34). The sheath includes any number of orienting pins, and generally includes an orienting pin for each reaction vessel or vial. For example, if the magnetizable sheet is configured to receive a linear array of 12 reaction vessel or vial lids, the sheath contains 12 orienting pins configured in a corresponding linear array so that each orienting pin separately aligns with the center (or approximately the center) of each of the separate lids of each reaction vial. If the magnetizable sheet is configured to receive a circular array of 24 reaction vial lids, the sheath includes 24 orienting pins configured in a corresponding circular array so that each orienting pin separately aligns with the center of each of the separate lids of each reaction vial. If the magnetic sheet is configured to receive a lid of a 96 well microtiter plate, then the sheath will include 96 orienting pins configured in a corresponding quadrangular array so that each orienting pin separately aligns with the center of each of the separate lids of each of the 96 chambers or wells.

The sheath can include one orienting pin for collection of magnetic beads from a single vessel. The sheath also can include any linear or circular configuration or any quadrangular array of orienting pins that is a multiple of 2, 3, 4, 5, 6, 7, 8, 9, 10, 11, 12, 13, 14, 15, 16, 17, 18, 19, 20, 21, 22, 23, 24, 36, 48 or 96. Therefore, the sheath can include, for example, 1, 2, 3, 4, 5, 6, 7, 8, 9, 10, 11, 12, 13, 14, 15, 16, 17, 18, 19, 20, 21, 22, 23, 24, 36, 48, 96, 384, 768, 864, 1152 or 1536 orienting pins. The orienting pins can be in an array of concentric circles or can be in an array of rows and columns, resulting in a rectangular or square array of pins. The configuration of the rows and columns in the array can be any configuration. In some embodiments, the configuration of the rows is in a ratio of 1:1, 2:3, 3:4 or 4:5. In some embodiments, the orienting pins can be arranged in a matrix of mutually perpendicular rows and columns. In some embodiments, the orienting pins are arranged in an x×y matrix, where x and y each independently is an integer selected from 1 to 100. In some embodiments, the orienting pins are arranged in an x×y matrix, where x and y each independently is an integer selected from 1 to 50.

In some embodiments, the matrix of orienting pins has a dimension selected from among 2×2, 2×3, 2×4, 2×5, 2×6, 2×7, 2×8, 2×9, 2×10, 2×11, 2×12, 3×3, 3×4, 3×5, 3×6, 3×7, 3×8, 3×9, 3×10, 3×11, 3×12, 4×4, 4×5, 4×6, 4×7, 4×8, 4×9, 4×10, 4×11, 4×12, 5×5, 5×6, 5×7, 5×8, 5×9, 5×10, 5×11, 5×12, 6×6, 6×7, 6×8, 6×9, 6×10, 6×11, 6×12, 7×7, 7×8, 7×9, 7×10, 7×11, 7×12, 8×8, 8×9, 8×10, 8×11, 8×12, 9×9, 9×10, 9×11, 9×12, 10×10, 10×11, 10×12, 11×11, 11×12, 12×12, 16×24, 18×24, 20×24, 22×24, 24×24, 24×48, 32×48 and 48×48.

The orienting pins can be of any material that concentrates magnetic fields, such as a material having a magnetic permeability, $\mu$, higher than the magnetic permeability of the material from which the sheath is fabricated. For example, if the sheath is formed of aluminum (which has a low magnetic permeability), the orienting pins are formed of a material with a magnetic permeability higher than aluminum. The orienting pins also can be magnets and oriented in the way that the magnetic fields of the magnet embedded in the sheath and of the orienting pins are aligned and are additive The orienting pins are made of any material, such as iron, steel, stainless steel, including that recited for the magnet embedded in the sheath, such as alnico magnets, ferrite magnets, rare-earth magnets, and high-performance magnets. For example, the orienting pins can be formed from cold rolled steel or 1040 steel. In some embodiments, the orienting pins can be formed of materials commonly known as mu metals, which include nickel-iron alloys such as 77% nickel, 15% iron, and varying amounts of copper and molybdenum. In some embodiments, the orienting pins are formed of a material selected from among conpernik (an alloy containing nickel and iron with no copper), an iron-cobalt-vanadium soft magnetic alloy (Hiperco®), an alloy of 80% Ni, 5% Mo, 0.5% Si, 0.02% Cu and Fe (Hymu 80®), an alloy containing 45-50% nickel and iron (Hypernik), an 80% Nickel/Iron/Molybdenum alloy (Hypernom), a 50% Fe—Ni alloy (Isoperm), a binary nickel-iron alloy containing 36% nickel (nilomag 36), a binary nickel-iron alloy containing 42% nickel (nilomag 42), a binary nickel-iron alloy containing 48% nickel (nilomag 48), a nickel-iron-cobalt alloy containing approximately 29% nickel and 17% cobalt (NILO alloy K), a nickel-iron-copper-molybdenum soft magnetic alloy (NILO alloy 77), a nickel iron magnetic alloy containing about 20% iron and 80% nickel content (Permalloy), 45 Permalloy (an alloy of 45% nickel and 55% iron), permenorm (an alloy of 50% nickel and 50% iron), Rhometal (an alloy that includes 36% Ni and 64% Fe), sanbold, Sendust, Sinimax (an alloy including 43% Ni, 54% Fe and 3% Si), Supermalloy (an alloy containing Ni (79%), Mo (5%), Fe (15%) and manganese (0.5%)), Permendur (an alloy containing 49% iron, 49% cobalt and 2% vanadium) and 1040 steel alloy. These alloys are commercially available (e.g., from Goodfellow Corp., Oakdale, Pa.; High Temperature Metals, Inc., Sylmar, Calif.; and DRMS Metals USA, Milton, W. Va.).

The orienting pins can be magnets or made of a magnetizable material. The orienting pins can be alnico magnets, ferrite magnets, rare-earth magnets, and high-performance magnets. In embodiments where the orienting pins are magnets, the sheath can include a magnet or the magnet in the sheath can be omitted. When the sheath includes a magnet and the orienting pins are magnets, the magnetic North pole face of each of the orienting pins points towards the magnetic South pole face of the magnet in the sheath or the magnetic South pole face of each of the orienting pins points towards the magnetic North pole face of the magnet in the sheath.

The magnet in the sheath also can be configured to include orienting pins. In some embodiments, the magnet in the sheath is configured to include protrusions that can function as orienting pins. The protrusions on the magnet that can serve or act as orienting pins can be of any shape. Exemplary shapes include parallelepiped including cuboid or cubus, block, ovoid, prism, antiprism, cylinder, ellipsoid, sphere, torus, cone, pyramid, obelisk, or truncated forms like truncated cone, frustum or any other polyhedron.

The relative magnetic permeability of aluminum is about 1. In some embodiments, the relative permeability of the material used to form the orienting pins is greater than 1. In some embodiments, the relative permeability of the material used to form the orienting pins is greater than 2, 3, 4, 5, 6, 7, 8, 9 or 10. In some embodiments, the relative permeability of the material used to form the orienting pins is 10 or greater. In other embodiments, the relative permeability of the material used to form the orienting pins is 100 or greater, including 200, 300, 400, 500, 600, 700, 800, 900 and 1000. In other embodiments, the relative permeability of the material used to form the orienting pins is 1000 or greater, including 2000, 3000, 4000, 5000, 6000, 7000, 8000, 9000, 10,000 and greater.

The orienting pins are retained in the bottom of the sheath by any suitable means. In some embodiments, the orienting pins are retained in the sheath by pressure fit, threads, friction fit, adhesive bonding or welding.

4. Fit Pins

The sheath of the magnetic separator device provided herein includes components to align the sheath with the plate, such as at least one fit pin. The fit pin(s) extend(s) from the sheath and engage(s) with and extend(s) through corresponding fit pin holes in the magnetizable plate. The fit pin allows for proper alignment of the sheath with the magnetizable plate. In some embodiments, the sheath includes on the surface of the sheath that receives and will be adjacent to the magnetizable plate, a different number of fit pins on opposite edges so that the magnetizable plate and the sheath can be aligned in only one orientation. In some embodiments, the sheath includes one fit pin at one edge and two or more fit pins on the opposite edge, which fit pins align with corresponding fit pin holes in the magnetizable plate. An exemplary depiction of this is shown in FIG. 1 (fit pins 32). During attachment of the sheath to the magnetizable plate, the protruding portion of the fit pins is located within the fit pin holes of the magnetizable plate to assure the proper alignment of the orienting pins in the sheath and the vial lid holes of the magnetizable plate.

The fit pins can be made of any material and can be of any configuration or geometry, including cylindrical, square peg and star-shaped peg. In some embodiments, the fit pins are of a non-magnetic material. In some embodiments, the fit pins are of a material having a permeability of about 1. In some embodiments, the fit pins are made of a non-magnetic plastic.

In some embodiments, the fit pins are made of a non-magnetic alloy. In some embodiments, the non-magnetic alloy contains copper, aluminum, chromium, zirconium, tungsten, magnesium, manganese, silicon or beryllium. In some embodiments, the fit pins are of aluminum or aluminum alloy. Examples of aluminum alloys that can be used include those made of aluminum-copper, aluminum-magnesium, aluminum-manganese, aluminum-silicon, aluminum-magnesium-silicon and aluminum-zinc based aluminum alloys.

In some embodiments, the fit pins are of a magnetic or magnetizable material. In some embodiments, the fit pins are made of steel, stainless steel, iron or alloys thereof. In some embodiments, the fit pins are formed of materials commonly known as mu metals, which include nickel-iron alloys such as 77% nickel, 15% iron, and varying amounts of copper and molybdenum. In some embodiments, the fit pins are formed of a material selected from among conpernik (an alloy containing nickel and iron with no copper), an iron-cobalt-vanadium soft magnetic alloy (Hiperco®), an alloy of 80% Ni, 5% Mo, 0.5% Si, 0.02% Cu and Fe (Hymu 80®), an alloy containing 45-50% nickel and iron (Hypernik), an 80% Nickel/Iron/Molybdenum alloy (Hypernom), a 50% Fe—Ni alloy (Isoperm), a binary nickel-iron alloy containing 36% nickel (nilomag 36), a binary nickel-iron alloy containing 42% nickel (nilomag 42), a binary nickel-iron alloy containing 48% nickel (nilomag 48), a nickel-iron-cobalt alloy containing approximately 29% nickel and 17% cobalt (NILO alloy K), a nickel-iron-copper-molybdenum soft magnetic alloy (NILO alloy 77), a nickel iron magnetic alloy containing about 20% iron and 80% nickel content (Permalloy), 45 Permalloy (an alloy of 45% nickel and 55% iron), permenorm (an alloy of 50% nickel and 50% iron), Rhometal (an alloy that includes 36% Ni and 64% Fe), sanbold, Sendust, Sinimax (an alloy including 43% Ni, 54% Fe and 3% Si), Supermalloy (an alloy containing Ni (79%), Mo (5%), Fe (15%) and manganese (0.5%)), Permendur (an alloy containing 49% iron, 49% cobalt and 2% vanadium) and 1040 steel alloy.

In some embodiments, the fit pins are adapted to secure the sheath to the magnetizable plate. In such embodiments, the fit pins are designed to fit snuggly into the fit pin holes in the magnetizable plate. The fit pins can secure the sheath to the magnetizable plate by any method. In some embodiments, the fit pins secure the sheath to the magnetizable plate by magnetic attraction or friction-fit. In some embodiments, the fit pins are screws and the fit pin holes have complementary screw threads for screwing the fit pins into the fit pin holes. In some embodiments, the fit pins are adapted to fit into the fit pin holes and lock into place upon 90° rotation of the fit pins. For example, in some embodiments, the fit pin is shaped as a square stick adapted to fit a square fit pin hole in the plate; the fit pin includes a longitudinal groove or notch parallel to the plate when inserted into the fit pin hole and adapted to accept the plate. When inserted into the fit pin hole in the magnetizable plate and rotated 90°, the groove or notch of the fit pin engages with the plate. Instead of being a square stick adapted to fit a square hole, the fit pins can be any shape, such as round or cylindrical, and include a longitudinal groove or notch parallel to the sheath that does not extend more than half-way around the circumference of the pin, where the notch is adapted to accept the thickness of the plate, and the pin is adapted to fit into fit pin holes in the plate. When inserted into the fit pin hole of the plate and rotated 90°, the fit pin secures the sheath to the magnetizable plate.

5. Magnetizable Plate

The magnetic separator devices provided herein includes a magnetizable plate. The plate is configured for accepting one or more lids of vessels. The plate is configured with one or more lid holes. The lid holes are sized to fit between the vessel lid and the vessel. The plate is configured so that one surface of the plate receives the lids of the vessels but does not interfere with the closure of the vessels by the lids. The vessels are oriented under the plate in alignment with the lid holes containing the lid(s). When the lids of the vessel in the magnetizable plate engage the vessels, the magnetizable plate is fixed between the lids and the vessels. An exemplary depiction of this is shown in FIG. 1. The magnetic plate can include a single hole for receiving a lid of a vessel. The magnetic plate also can include multiple holes for receiving lids of one or more vessels. The holes in the plate for receiving the reaction lids can be configured in any linear or circular configuration or any quadrangular array that is a multiple of 2, 3, 4, 5, 6, 7, 8, 9, 10, 11, 12, 13, 14, 15, 16, 17, 18, 19, 20, 21, 22, 23, 24, 36, 48 or 96. Therefore, the plate can include, for example, 1, 2, 3, 4, 5, 6, 7, 8, 9, 10, 11, 12, 13, 14, 15, 16, 17, 18, 19, 20, 21, 22, 23, 24, 36, 48, 96, 192, 384, 768, 864, 1152 or 1536 orienting pins. The lid holes of the magnetizable plate can be in an array of concentric circles or can be in an array of rows, resulting in a rectangular or square array of lid holes. The lid holes of the magnetizable plate that receive the lids of vessels are configured so that they align with the orienting pins of the sheath, such that each of the separate orienting pins of the sheath separately aligns with and is essentially or exactly in the center of each of the separate lids. For example, if the orienting pins of the sheath are in a linear array of twelve, then the magnetizable plate includes a corresponding linear array of twelve holes for receiving lids of the vessel. If the orienting pins of the sheath are in a circular array of 24, then the magnetizable plate includes a corresponding circular array of 24 holes for receiving lids of vessels configured so that one of each of the orienting pins is essentially or exactly in the center of one of each lid of each vessel.

The magnetizable plate of the magnetic separator device disclosed herein can be made of any magnetic or magnetizable material. In some embodiments, the magnetizable plate is made of steel, stainless steel, iron or alloys thereof. In some embodiments, the magnetizable plate is formed of a material termed "magnifer 75", a soft magnetic nickel-iron alloy containing about 5% copper and 2% chromium. In some embodiments, the magnetizable plate is formed of materials commonly known as mu metals, which include nickel-iron alloys such as 77% nickel, 15% iron, and varying amounts of copper and molybdenum. In some embodiments, the magnetizable plate is formed of a material selected from among conpernik (an alloy containing nickel and iron with no copper), an iron-cobalt-vanadium soft magnetic alloy (Hiperco®), an alloy of 80% Ni, 5% Mo, 0.5% Si, 0.02% Cu and Fe (Hymu 80®), an alloy containing 45-50% nickel and iron (Hypernik), an 80% Nickel/Iron/Molybdenum alloy (Hypernom), a 50% Fe—Ni alloy (Isoperm), a binary nickel-iron alloy containing 36% nickel (nilomag 36), a binary nickel-iron alloy containing 42% nickel (nilomag 42), a binary nickel-iron alloy containing 48% nickel (nilomag 48), a nickel-iron-cobalt alloy containing approximately 29% nickel and 17% cobalt (NILO alloy K), a nickel-iron-copper-molybdenum soft magnetic alloy (NILO alloy 77), a nickel iron magnetic alloy containing about 20% iron and 80% nickel content (Permalloy), 45 Permalloy (an alloy of 45% nickel and 55% iron), permenorm (an alloy of 50% nickel and 50% iron), Rhometal (an alloy that includes 36% Ni and 64% Fe), sanbold, Sendust, Sinimax (an alloy including 43% Ni, 54% Fe and 3% Si), Supermalloy (an alloy containing Ni (79%), Mo (5%), Fe (15%) and manganese (0.5%)), Permendur (an alloy containing 49% iron, 49% cobalt and 2% vanadium) and 1040 steel alloy.

The magnetizable plate includes fit pin holes for receiving the fit pins of the sheath. The holes for receiving the fit pins of the sheath allow for proper alignment of the sheath with the magnetizable plate. In some embodiments, the magnetizable plate includes a different number of fit pin holes on opposite edges so that the magnetizable plate and the sheath can be aligned in only one orientation. In some embodiments, the magnetizable plate includes an edge having one or more fit pins and an opposite edge having a different number of fit pins to ensure only one orientation for the magnetizable plate to receive the sheath. In some embodiments, the magnetizable plate includes one fit pin hole at one edge and two or more fit pin holes on the opposite edge, which fit pin holes align with corresponding fit pins in the sheath. In some embodiments, when the magnetizable plate receives the sheath (the fit pin holes receive the fit pins of the sheath), the plate is retained by the magnetic field of the magnet.

The magnetizable plate can be any shape or geometry, including circular and quadrangular, such as square and rectangular. In some embodiments, the magnetizable plate is of the same size and shape as the sheath. In some embodiments, the plate is of the same shape as the sheath but is of a slightly larger dimension than the sheath, producing a small lip or extension of the plate when attached to the sheath. The extension of the plate can be used to more easily remove the magnetizable plate from the sheath. In some embodiments, one end of the plate is of a geometry or size that produces an extension of the plate that extends past the sheath when the magnetizable plate is attached to the sheath, the extension allowing for an operator or a robot to more easily remove the plate from the sheath.

6. Optional Rack for Holding Vessels

The magnetic separator device provided herein optionally includes a rack for holding the vessels. In embodiments where the vessels are vials, the rack is configured to receive the vials, and can include a support that includes holes through which the vials can be placed, or can include cups configured to fit the vials. In embodiments when the vessel is a multi-well plate, such as a microtiter plate, such as a standard 96-well rectangular microtiter plate, the rack can include a rectangular hole configured to receive and hold the microtiter plate. The rack also can be configured to be a rectangular receptacle having a bottom and at least two sides for receiving and holding the microtiter plate.

The rack can by of any material, including metal, glass or plastic. In some embodiments, the rack is of a material transparent to UV light, such as a clear acrylic plastic that transmits UV light, and the rack allows passage of UV light through the rack to reach the vessel.

7. Vessels Having Lids

The magnetic separator device provided herein is configured to receive lids of vessels. The lids can be separate or can be provided attached together, as in an array or a strip of lids. The lids also can be attached together to form an array of plugs that fits within and seals the opening of each vessel. For example, a lid for a standard 96-well microtiter well plate would have an aligned array of 96 plugs each of which fills the opening of one of the wells in the plate and seals the opening. Similarly, a lid for a standard 384-well microtiter well plate would have an aligned array of 384 plugs each of which fills the opening of one of the wells in the plate and seals the opening. When the vessels are vials, the lid can be a separate plug that fills the opening of the vial and seals it. The vial lids can be separate or can be provided as a strip of lids. In some embodiments, the lid includes a plug with a sealing portion that can engage with the interior of the well or vial or with a ring around the top of the well or vial to seal it. The lids may be in contact with the reaction mixture.

The lids can be made of any suitable material, such as plastic, wax or silicone. The material can be an elastomeric material or a rigid material. In some embodiments, the lids are of chemically inert elastomeric compounds that will fit against the vial or well surface to form a seal. In some embodiments, the lids are of plastic, acrylic, urethane, polypropylene, polystyrene, Teflon or medical grade silicone rubber. In some embodiments, the lids are metal, such as iron or stainless steel, where the metal plugs are coated with a material such as plastic, acrylic, urethane, polypropylene, polystyrene, teflon or medical grade silicone rubber.

D. Magnetic Particles

1. Magnetic Particles/Beads

The methods and devices provided herein use magnetic particles (or beads). Any particle, such as a bead, that is a magnetic particle or that can be trapped by a magnetic source, such as a magnet, is a magnetic particle. Magnetic particles are well known in the art, any of which can be used in the methods and with the devices provided herein. The art has described a number of magnetic particles that can be used. For example, see U.S. Pat. Nos. 4,628,037, 4,695,392, 4,695,393, 4,698,302, 4,554,088, U.K. Patent Application GB 2,005,019A and EP 0,180,384, which provide magnetic particles. Any magnetic particle to which molecules can be attached is intended for use with the devices provided herein. The magnetic particles can be paramagnetic, superparamagnetic or ferromagnetic and can include or be a solid support that can be derivatized. An exemplary magnetic particle is a magnetic bead.

Any solid support in the form of a bead can be made magnetically responsive by incorporation of a magnetic or paramagnetic or superparamagnetic substance, such as for example, magnetite, iron, cobalt, nickel, individually or in the form of alloys in the interior or surface of the bead. The solid support can be constructed of any suitable material, such as, glass, silicon, metal, plastic or a composite, silica gel, dextran or cellulose.

The magnetic particles, such as beads, can have any susceptibility. In some embodiments, the magnetic particles used in the methods or with the magnetic separator device disclosed herein have a susceptibility of at least 0.001 cgs units. In some embodiments, the susceptibility is at least 0.01 cgs units. The magnetic particles may have a broad range of densities, e.g., substantially less than that of water, or from 0.01 to 5 g/mL or from 0.5 to 2 g/mL. The concentration of the particles may range broadly from 1 to 10,000 µg per mL or from 5 to 1000 µg per mL.

In some embodiments, the magnetic particle is a magnetic bead. Magnetic beads are known in the art and are available commercially. When target molecules are attached to magnetic beads, complexes of target molecules and the beads can rapidly be partitioned and isolated from the reaction mixture by the application of a magnetic field to the lid of the vessel. In some embodiments, the magnetic field is applied by use of the magnetic separator device described herein.

The magnetic particles can be of any convenient size. Typically the magnetic particles have at least one dimension in the range of 5-10 mm or smaller, such as less than 1000 µm or less than 100 µm or less than 50 µm or less than 10 µm or less than 5 µm or less than 1 µm. In one embodiment, the diameter of the magnetic bead is in the range of 0.1-100 µm. In one embodiment, the diameter of the magnetic bead is in the range of 0.25-50 μm. In some embodiments, the magnetic particles are from 0.02 to 20 microns in diameter. In some embodiments, the magnetic particles are from 0.05 to 15 microns in diameter. In some embodiments, the diameter of the magnetic particles is in the range of 0.5-25 μm. In one embodiment, the diameter of the magnetic particles is in the range of 1-10 μm. In some embodiments, the magnetic particles are from 0.05 to 5 microns in diameter. In some embodiments, the magnetic particles are from 0.05 to 3 microns in diameter. In some embodiments, the diameter of the magnetic particles is selected from about or at 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 and 10.0 microns. Exemplary magnetic particles are Dynabeads™ magnetic beads (Dynal, Inc. Great Neck, N.Y.), which have a diameter of about 3-5 μm. In some embodiments, the magnetic particles used have a uniform diameter (monodisperse). In some embodiments, the diameters of the magnetic particles vary (polydisperse).

2. Attachment of Molecules to Magnetic Particles

Molecules can be linked to magnetic particles/beads by any suitable method. Typically, the magnetic/bead particle has a surface that is suitable for linkage of molecules or that can be suitably derivatized. Generally, the magnetic particle is a typical solid support combined with a magnet or other magnetized material. Methods for linking molecules to solid supports are very well known. Conjugation of molecules to magnetic particles is described, for example, in U.S. Pat. Nos. 4,935,147 and 5,145,784. For exemplification purposes, linking of capture compounds is described herein.

In some embodiments, the molecule can be attached to the magnetic particle directly. In some embodiment, a capture compound is attached to the magnetic particle and the capture compound is used to capture a molecule from a sample solution or reaction mixture. In some embodiments, a capture compound is attached or bound to a target molecule in a sample to form a complex, and the resulting complex is bound to the magnetic particle. A molecule, such as a capture compound, can be attached to the particle by any means, either directly or indirectly, including adsorption onto the surface, covalent linking to the surface, attachment through one member of a specific binding pair, attachment through a linker, such as a chemical moiety linker or a nucleic acid, or through a linker that can be cleaved chemically or enzymatically.

Covalent attachment of molecules to solid supports, including magnetic particles that serve as solid supports, is well known in the art, and can be achieved using any of the wide variety of derivatization chemistries well known in the art. In some embodiments, the magnetic particles include a solid support functionalized with various molecules or chemical constituents including, but not limited to, avidin, streptavidin, biotin; peptides; haptens; aptamers; nucleic acids (e.g., DNA), nucleotides; esters (e.g., N-hydroxy-succinimide ester); antibodies/antigen interactions (e.g., anti-TNF-α antibody); antigens; vitamins and cofactors (e.g., biotin); or any combinations thereof. Functionalization of the surface of the magnetic particle is achieved with any of the various coupling reagents known in the art, such as, but not limited to, 3-(3-dimethyl-aminopropyl)-1-ethylcarbodiimide (EDC) and biotinamidohexanoyl-6-amino-hexanoic acid N-hydroxy-succinimide (NHS) ester (i.e., Biotin-NHS), as well as other methodologies and reagents as will be known to those of skill in the art.

Thus, the magnetic particles, such as magnetic beads, can include a solid support that includes a surface functionality. Exemplary surface functionalities include one member of a specific binding pair, such as an antigen, an antibody, avidin, NeutrAvidin, CaptAvidin, streptavidin, biotin, protein A, protein G, an oligonucleotide, a peptide or a lectin. The magnetic particles can be functionalized by including a functional group as is known in the art (e.g., see Hawkins, U.S. Pat. No. 5,705,628). The functional group allows attachment of a target molecule or a capture compound to the magnetic particle. The functional groups can include, e.g., a protein, an antibody, an antigen, a nucleic acid, a nucleotide or a specific biomarker.

The surface functional group on the magnetic particle can be a reactive moiety for coupling of a molecule, such as a capture compound, to the bead surface. For example, molecules, such as capture compounds containing carboxyl groups or groups that can be carboxylated can be conjugated to a bead with an amino functionality via the mixed anhydride method, the carbodiimide method, using dicyclohexylcarbodiimide, and the N hydroxysuccinimide ester method. If the molecule contains amino groups or reducible nitro groups or can be substituted with such groups, conjugation to the bead can be achieved by one of several techniques. For example, aromatic amines can be converted to diazonium salts by the slow addition of nitrous acid and then reacted with proteins at a pH of about 9. If the target molecule contains aliphatic amines, such groups can be conjugated to the beads that include a carboxy functionality by various methods, including carbodiimide, tolylene-2,4-diisocyanate, or malemide compounds, such as the N-hydroxysuccinimide esters of malemide derivatives. Also, bifunctional esters, such as dimethylpimelimidate, dimethyladipimidate, or dimethylsuberimidate, can be used to couple amino-group containing moieties to beads.

Molecules, such as capture compounds, containing hydroxyl groups can be conjugated to beads by any of a variety of procedures. For example, the conversion of an alcohol moiety to the half ester of succinic acid (hemisuccinate) introduces a carboxyl group available for conjugation. The bifunctional reagent sebacoyldichloride converts alcohol to acid chloride which, at pH 8.5, reacts readily with amino functionalities.

For example, for molecules, such as capture compounds containing ketones or aldehydes, such carbonyl-containing groups can be derivatized into carboxyl groups through the formation of O-(carboxymethyl) oximes. Ketone groups can also be derivatized with p-hydrazinobenzoic acid to produce carboxyl groups that can be conjugated to the beads. Organic moieties containing aldehyde groups can be directly conjugated to the beads through the formation of Schiff bases which are then stabilized by a reduction with sodium borohydride. Other methods and reagents are described in S. S. Wong, "Chemistry of Protein Conjugation and Cross-Linking," (CRC Press, Inc., Boca Raton, Fla. (1993)). Other cross-linking reagents can be used that introduce spacers in the molecule, such as a capture compound. The selection of spacer can be chosen to alter properties of the molecules, such as to preserve or enhance reactivity between the members of the specific binding pair, or, conversely, to limit the reactivity, as may be desired to enhance specificity and inhibit the existence of cross-reactivity. For example, the length of the spacer can change steric properties, the length and composition of the spacer can alter solubility of the compounds. In the caprotec Capture Compound™ compounds, the spacer can include the solubility functionality designated "W."

The molecule, such as a capture compound, can be attached to the magnetic beads covalently or via noncovalent attachment. Methods for noncovalent attachment of biological recognition molecules to magnetic particles are well known in the art. Non-covalent attachment of molecules includes any of a variety of non-covalent interactions, such as hydrophobic interactions and van der Waals interactions and ionic interactions. The magnetic particle also can be coated with one member of a specific binding pair, which binds to the corresponding binding pair member that is attached to a molecule of interest or a capture compound. For example, a magnetic particle that includes streptavidin will bind with high affinity to a molecule, such as a capture compound, that is conjugated to biotin.

Thus, the reactive moiety on the magnetic particle bead can be a cross-linking reagent, including bifunctional cross-linking agents. Bifunctional cross-linking reagents have been used for a variety of purposes including preparation of affinity matrices, modification and stabilization of diverse structures, identification of ligand and receptor binding sites, and structural studies. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group. Magnetic particles, such as beads, that are pre-coated with one member of a specific binding pair, such as streptavidin, or with antibodies or antigens or with specific surface functionalities, are commercially available (e.g., Dynal, Inc. Great Neck, N.Y. and Oslo Norway; Bioclone, Inc, San Diego, Calif.).

The magnetic particles used herein can be fabricated from any number of known materials. Examples of such materials include inorganic materials, natural polymers and synthetic polymers. Specific examples of these materials include acrylic resins, agarose (e.g., Sepharose®), cellulose, cellulose derivatives, co-polymers of vinyl and acrylamide, dextran, cross-linked dextran, dextran cross-linked with epichlorohydrin (e.g., Sephadex®), gelatin, glass (e.g., controlled-pore glass (CPG)), latex, Merrifield resin (polystyrene cross-linked with divinylbenzene, see Merrifield, Biochemistry 3: 1385-1390 (1964)), metal (e.g., (steel, gold, silver, platinum, aluminum, copper and silicon), nylon, plastic (e.g., polyethylene, polypropylene, polyvinylidenedifluoride (PVDF), polyamide, polyester), polyacrylamide, polystyrene, polystyrene cross-linked with divinylbenzene, polyvinyl pyrrolidone, rubber, silica gel and Wang resin.

E. Capture Compounds

The target molecule can be selected from a reaction mixture by using a capture compound. In some embodiments, the capture compound includes one or more functional groups and optionally is bound to a solid support, such as a magnetic particle. In some embodiments, the capture compounds include one or a plurality of chemical moieties that can interact with a molecule of interest.

Capture compounds are well known in the art (e.g., see U.S. Pat. Nos. 6,942,974 and 7,094,943, U.S. patent application Ser. No. 10/197,954, published as US-20030119021; U.S. patent application Ser. No. 10/760,085, published as US20050042771 and republished as US20060051879; U.S. patent application Ser. No. 10/388,027, published as US20040209255; Australian Pat. No. AU 2004206856; European Pat. No. EP 1485707; European Pat. App. EP 1 583 972; Japanese Patent No. JP 3935487; and International Patent Applications published as WO 01/77668, WO 01/77684, WO 98/059360, WO 98/059361 and WO 98/059362, each of which is incorporated herein in its entirety.

Capture compounds can be used to isolate and/or select any molecule from any solution, reaction mixture or sample. The capture compounds can include functional groups that confer reactivity, selectivity and separative properties, depending on the specificity of separation and analysis required (which depends on the complexity of the mixture to be analyzed). As more functional groups are added to the compounds, the compounds can exhibit increased selectivity and develop a signature for target molecules similar to an antigen binding site on an antibody. In general, the capture compounds include at least two functional groups selected from four types of functions: a reactivity function, which binds to biopolymers either covalently or with a high $K_a$ (generally greater than about $10^9$, $10^{10}$, $10^{12}$ liters/mole and/or such that the binding is substantially irreversible or stable under conditions of mass spectrometric analyses, such as MALDI-MS conditions); a selectivity function, which by virtue of non-covalent interactions alters, generally increases, the specificity of the reactivity function; a sorting function, which permits the compounds to be addressed (arrayed or otherwise separated based according to the structure of the capture compound; and a solubility function, which when selected alters the solubility of the compounds depending upon the environment in which reactions are performed, permitting the conditions to simulate physiological conditions. In some embodiments, the reactivity function specifically interacts with molecules of interest, such as proteins or other biomolecules; and the sorting function permits separation or immobilization of capture compounds. In some embodiments, the sorting function can bind either covalently or noncovalently to a specific molecule(s).

In some embodiments, the capture compounds can include at least a reactivity function and a selectivity function and can be bound to a solid support, such as a magnetic particle, or can include a functionality that permits attachment to a solid support. In some embodiments, the capture compounds include at least a reactivity function, a selectivity function, and a sorting function. In some embodiments, the capture compounds can be attached to a solid support, such as a magnetic particle, via the sorting function, or the capture compounds are attached to a solid support via a linker or functionality other than the sorting function that permits attachment to a solid support. These capture compounds also optionally include one or more solubility functions, which are moieties that influence the solubility of the resulting compound, to attenuate or alter the hydrophobicity or hydrophilicity of the compounds.

Collections of capture compounds can be used to generate compound arrays to capture target proteins or groups of related proteins that can mimic biological structures such as nuclear and mitochondrial transmembrane structures, artificial membranes or intact cell walls. Thus, the capture compounds and capture compound arrays are capable of mimicking biological entities and biological surfaces, thereby allowing for capture of molecules, such as biomolecules, e.g., proteins, which would otherwise be difficult or impossible to capture, such as those found in transmembrane regions of a cell.

The capture compounds for use in isolating molecules of interest can be classified in at least two sets: one for reactions in aqueous solution (e.g., for reaction with hydrophilic biomolecules), and the other for reaction in organic solvents (e.g., chloroform) (e.g., for reaction with hydrophobic biomolecules). Thus, in certain embodiments, the capture compounds discriminate between hydrophilic and hydrophobic molecules, such as biomolecules, including, but not limited to, proteins, and allow for analysis of both classes of molecules.

In some embodiments, the capture compounds include a core or scaffold "Z" that presents one or more reactivity functions "X" and optionally at least a selectivity function "Y" and/or a sorting function "Q", and also optionally one or more solubility functions "W." Additionally, cleavable linkers and other functions can be included in the molecules. A reactivity function X effects the covalent binding or a high binding affinity (high $K_a$) binding, and least one of three other groups (also referred to herein as functions or functionalities). A selectivity function Y modulates the interaction of a molecule with the reactivity function. A sorting function Q allows for addressing the capture compound or for its removal, such as on a solid support, e.g., a magnetic bead. A solubility function W alters solubility of the capture compound, such as by increasing the solubility of the capture compound under selected conditions, such as various physiological conditions, including hydrophobic conditions of cell membranes.

The particular manner in which the functions are presented on the core or scaffold Z is a matter of design choice, but the manner of presentation is selected such that the resulting capture compound molecule has the property that it captures molecules, such as biomolecule, e.g., proteins, with sufficient specificity and either covalently or with bonds of sufficient stability or affinity to permit analysis, such as by mass spectrometry, including MALDI mass spectrometric analysis, so that at least a portion of bound molecules, such as biomolecules, remain bound (generally having a binding affinity of $10^9$, $10^{10}$, $10^{11}$ liters/mole or greater, or a $K_{eq}$ of $10^9$, $10^{10}$, $10^{11}$, $10^{12}$ or greater).

In one embodiment, the capture compounds for use in the methods provided herein have formulae: Q-Z-X or Q-Z-Y. In such embodiments, when an optional solubility function W is present, the capture compounds can have the formula:

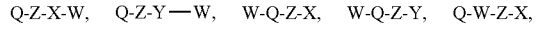

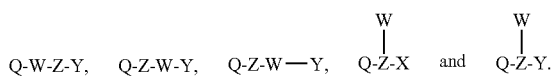

In another embodiment, the capture compounds for use in the methods provided herein have the formula:

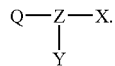

In such embodiments, when an optional solubility function W is present, the capture compounds can have, e.g., any of the following formulae:

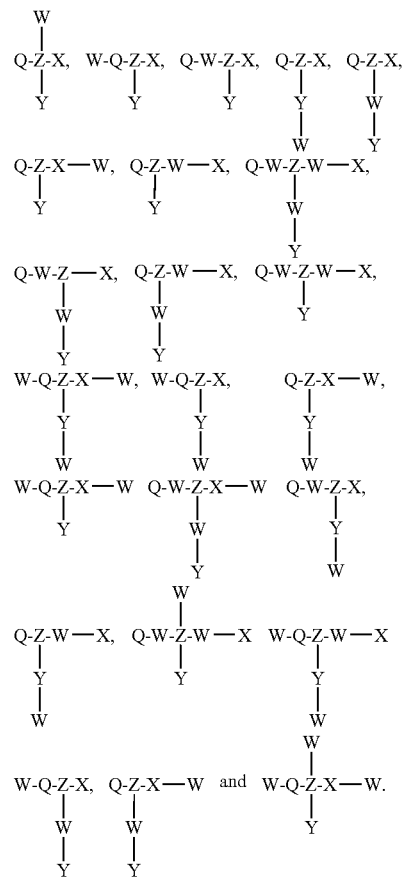

Other configurations also are contemplated.

In some embodiments, the compounds for use in the methods provided herein have the formulae:

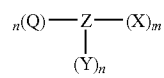

or $(Q)_n$-Z-$(X)_m$ or $(Q)_n$-Z-$(Y)_n$, where Q, Z, X and Y are as defined above; m is an integer from 1 to 100, in one embodiment 1 to 10, in another embodiment 1, 2, 3, 4 or 5; and n in an integer from 1 to 100, in one embodiment 1 to 10, in another embodiment 1, 2, 3, 4 or 5. In such embodiments, an optional solubility function W can be present.

A collection of capture compounds can be used. In some embodiments, a variety of different sorting groups can be used and each set of capture compounds has a unique Q compared to the other sets. In some embodiments, a collection of capture compounds is used and the collection can include sets of capture compounds, each of which set differs in Q and at least one or both X and Y.

1. Reactivity Function—X

In general, the reactivity function covalently interacts with groups on a particular target molecule, such as a protein, or portions thereof, such as amine groups on the surface of a protein. The reactivity function interacts with molecules to form a covalent bond or a non-covalent bond that is stable under conditions of analysis, generally with a $K_a$ of greater than $10^9$ liters/mole or greater than $10^{10}$ liters/mole. Conditions of analysis include, but are not limited to, mass spectrophotometric analysis, such as matrix assisted laser desorption ionization-time of flight (MALDI-TOF) mass spectrometry.

The reactivity function, X, is a group or moiety that forms a covalent bond or a bond of high affinity that is stable under conditions of mass spectrometric analysis, particularly MALDI analysis. For example, the reactivity function X includes groups that specifically react or interact with functionalities on the surface of a protein such as hydroxyl, amine, amide, sulfide, thiol and carboxylic acid groups, or that recognize specific surface areas, such as an antibody, a lectin or a receptor-specific ligand, or interacts with the active site of enzymes. Those skilled in the art can select from a library of functionalities to accomplish this interaction. While this interaction can be highly reaction-specific, these compounds can react multiple times within the same protein molecule depending on the number of surface-accessible functional groups. Modification of the reaction conditions allows the identification of surface accessible functional groups with differing reactivity, thereby permitting identification of one or more highly reactive sites used to separate an individual protein from a mixture. Available technologies do not separate species in the resulting reaction mixture. The collections and compounds provided herein solve that problem through a second functionality, the selectivity function, which alters binding of the reactivity groups to the biomolecule.

In one embodiment, the reactivity function covalently "captures" or binds to the molecule, such as a biomolecule, e.g., a selected protein. While the selectivity function, described below, serves as the "bait" for the molecule of interest, the reactivity function serves as the "hook." A molecule, such as a biomolecule, e.g., protein, thus captured will be able to survive downstream purification and analytical processes. The reactivity function(s) are chemically reactive with certain functionalities on the molecule, such as side chains on a protein (e.g., N-hydroxy succinimide (NHS) forms a bond with a lysine amino function), or require an activation step (i.e. light) prior to forming a covalent bond (e.g., the reactivity function can be a photoactivatable moiety such as azide, diazirine, benzophenone which forms a nitrene, a carbine or radical respectively).

In some embodiments, the reactivity function is a moiety that binds to or interacts with the surface of a molecule, including, but not limited to, the surface of a protein; an amino acid side chain of a protein; or an active site of an enzyme (protein) or to functional groups of other biomolecule, including lipids, polynucleotides and polysaccharides.

Thus, for example, the reactivity function is a group that reacts or interacts with functionalities on the surface of a molecule, such as a protein, to form covalent or non-covalent bonds with high affinity. When the target molecule is a protein, a wide selection of different functional groups are available with which the reactivity function can interact. For example, the reactivity function can act either as a nucleophile or an electrophile to form covalent bonds upon reaction with the amino acid side chains on the surface of a protein. Exemplary reagents that bind covalently to amino acid side chains include, but are not limited to, protecting groups for hydroxyl, carboxyl, amino, amide, and thiol moieties, including, for example, those disclosed in T. W. Greene and P. G. M. Wuts, "Protective Groups in Organic Synthesis," 3rd ed. (1999, Wiley Interscience). These protecting groups react with amino acid side chains such as hydroxyl (serine, threonine, tyrosine); amino (lysine, arginine, histidine, proline); amide (glutamine, asparagine); carboxylic acid (aspartic acid, glutamic acid); and sulfur derivatives (cysteine, methionine), and are readily adaptable for use in the capture compounds as the reactive function moiety X.

It is in addition to the wide range of group-specific reagents that are known to persons of skill in the art, reagents that are known in natural product chemistry also can serve as the reactive function moiety in forming covalent linkages. Other choices for the reactive function moiety include protein purification dyes, such as acridine or methylene blue, which have a strong affinity for certain proteins.

In some embodiments, the reactivity function moiety includes groups that are inert toward reaction with the target molecule, such as a biomolecule such as a protein, until activated. Such groups include photoactivatable groups, including but not limited to, azide, benzophenone and diazirine groups. In another embodiment, an active ester (e.g., N-hydroxy succinimide (NHS)) is used as the reactivity function. For example, the active ester is inert toward reaction with amine groups under acidic conditions, but will react upon raising the pH. In some embodiments, the reactivity function moiety is a photoactivatable group and the capture compounds includes a selectivity function and the capture compound is allowed to interact with a mixture of molecules, such as a biomolecular mixture until, for example, equilibrium is reached. The photoactivatable reactivity function moiety then is activated by exposure to the appropriate wavelength of light, whereby the reactivity function moiety then reacts with a surface group of the biomolecule to capture it. In one embodiment, the photoactivatable group is an arylazide, such as a phenylazide. Following exposure to light, the resulting nitrene will react with, e.g., the side chain of tyrosine to capture the protein. In another embodiment, the photoactivatable group is a diazirine group, such as 3-trifluoromethyldiazirine and the resulting carbene forms a covalent bond with functional groups on the surface of the biomolecule such as a protein.

In certain embodiments, the reactivity function moiety is an active ester, such as $C(=O)OPhpNO_2$, $C(=O)OC_6F_5$ or $C(=O)O(Nsuccinimidyl)$, an active halo moiety, such as an α-halo ether or an α-halo carbonyl group, including, but not limited to, $OCH_2I$, $OCH_2Br$, $OCH_2Cl$, $C(O)CH_2I$, $C(O)CH_2Br$ and $C(O)CH_2Cl$; amino acid side chain-specific functional groups, such as maleimido (for cysteine), a metal complex, including gold or mercury complexes (for cysteine or methionine), an expoxide or isothiocyanate (for arginine or lysine).

In some embodiments X is an N-hydroxysuccinimidyl ester, or is selected from among 1,3-dioxoisoindolin-2-yl acetate, 1-acetyl-1H-pyrrole-2,5-dione, oxiran-2-yl acetate, (2-oxo-1,3-dioxolan-4-yl)methyl acetate, 4-methyl-1,3-dioxolan-2-one, acetic pivalic anhydride and N-(3-aminopropyl)acetamide.

In some embodiments X is selected from among an active ester, an active halo moiety, an amino acid side chain-specific functional group and a metal complex. In some embodiments X is an α-halo ether, an α-halo carbonyl group, maleimido, a gold complex, a mercury complex, an expoxide or an isothiocyanate. In some embodiments X is —C(=O)O-Ph-pNO_2, —C(=O)O—C_6F_5, —C(=O)—O—(N-succinimidyl), —OCH_2—I, —OCH_2—Br, —OCH_2—Cl, —C(O)CH_2I, —C(O)CH_2Br or —C(O)CH_2Cl.

In other embodiment, the reactivity function moiety is linked to the central core Z via a spacer. A spacer can be any group that provides for spacing, typically without altering desired functional properties of the capture compounds and/or capture compound/biomolecule complexes. The reactivity function X linked with the spacer can be extended from the central core Z, to reach to the active sites on the surface of the biomolecule, such as proteins. Those of skill in the art in light of the disclosure herein, can readily select suitable spacers. In some embodiments, S is selected from $(CH_2)_r$, $(CH_2O)$, $(CH_2CH_2O)_r$, $(NH(CH_2)_rC(=O))_s$, $(O(CH)_rC(=O))_s$, $-((CH_2)_{r1}-C(O)NH-(CH_2)_{r2})_s-$ and $-(C(O)NH-(CH_2)_r)_s$, where r, r1, r2 and s are each independently and integer from 1 to 10.

2. Selectivity Function—Y

In general, the selectivity function alters the specificity of the reactivity function or modulates the interaction of the reactivity function with a target molecule, and in some embodiments the selectivity function can be selected as a moiety whose interactions are to be assessed. In some embodiments, the selectivity function influences the types of molecules, such as biomolecules, that can interact with the reactivity function through a non-covalent interaction. The selectivity function can alter the specificity for the particular groups, generally reducing the number of such groups with which the reactivity functions react. A goal is to reduce the number of molecules, such as biomolecules, e.g., proteins, bound at a locus, so that the proteins can then be separated more selectively and optionally analyzed, such as by mass spectrometry.

The selectivity function Y is used for electronic (e.g., mesomeric, inductive) and/or steric effects to modulate the activity of the reactivity function as well as the resulting affinities of the capture compound and the stability of the resulting reactivity function—target molecule linkage. In these embodiments, molecular mixtures, such as mixtures of biomolecules including, but not limited to, protein mixtures, can react and be analyzed due to the modulation of the reactivity function by the selectivity function Y, which changes the electronic or steric properties of X and, therefore, increases the selectivity of the reaction of X with the target molecule, such as a biomolecule, e.g., a protein.

Selectivity function moieties include any functional groups that increase the selectivity of the reactivity group so that the reactivity group binds to fewer different molecules, such as biomolecules, than in the absence of the selectivity function or binds with greater affinity to molecules, such as biomolecules, than in its absence. In the capture compounds provided herein, the selectivity function Y is allowed to be extensively varied depending on the goal to be achieved regarding steric hindrance and electronic factors as they relate to modulating the reactivity of the reactive function X. For example, a reactivity function X can be selected to bind to amine groups on proteins; the selectivity function can be selected to ensure that only groups exposed on the surface can be accessed. The selectivity function is such that the capture compounds bind to or react with (via the reactivity function) fewer different molecules, such as biomolecules, when it is part of the capture compound than when it is absent and/or the capture compounds bind with greater specificity and higher affinity. The selectivity function can be attached directly to a compound or can be attached via a linker, such as $CH_2CO_2$ or $CH_2-O-(CH_2)_n-O$, where n is an integer from 1 to 12, or 1 to 6, or 2 to 4. In certain embodiments, the linker is chosen such that the selectivity function can reach the binding pocket of a target or non-target protein. In another embodiment, the selectivity function is a chiral group, which allows for stereoselective capture of molecules such as biomolecules.

In some embodiments, the selectivity function, Y, is a group or moiety that "looks" at the topology of the protein around reactivity binding sites and functions to select particular groups on molecules, such as biomolecule, from among those with which a reactivity group can form a covalent bond (or high affinity bond). For example, a selectivity function Y can cause steric hindrance, or permit specific binding to an epitope, or anything in between. It can be a substrate for or an inhibitor or co-factor of an enzyme, a drug, a pro-drug, a drug metabolite, ligand interacting with a receptor, a nucleic acids/ oligonucleotide, a lipid, a peptide or a carbohydrate. It can be selected to modify the environment of the groups with which the reactivity function interacts. The selectivity function Y can be one whereby a capture compound forms a covalent bond with a molecule, such as a biomolecule, in a mixture or interacts with high stability such that the affinity of binding of the capture compound to the molecule, such as a biomolecule, through the reactivity function in the presence of the selectivity function is at least five-fold, ten-fold or 100-fold greater than in the absence of the selectivity functionality. In some embodiments, the selectivity function Y increases the selectivity of the binding by X such that the capture compound binds to fewer biomolecules when Y is present than in its absence, whereby Y modulates the one or more of the affinity, steric properties and electronic properties of the capture compound.

In certain embodiments, the selectivity function is selected from ATP analogs and inhibitors; peptides and peptide analogs; polyethyleneglycol (PEG); activated esters of amino acids, isolated or within a peptide; cytochrome C; and hydrophilic trityl groups.

In another embodiment, Y is a small molecule moiety, a natural product, a protein agonist or antagonist, a peptide or an antibody. In another embodiment, Y is a hydrophilic compound or protein (e.g., PEG or trityl ether), a hydrophobic compound or protein (e.g., polar aromatics, lipids, glycolipids, phosphotriesters, oligosaccharides), a positive or negatively charged group, a small molecule, a pharmaceutical compound or a biomolecule that creates defined secondary or tertiary structures.

In certain embodiments, the selectivity function Y is an enzyme inhibitor, an enzyme agonist or antagonist, a pharmaceutical drug or drug fragment, a prodrug or drug metabolite or drug synthetic intermediate that modifies the selectivity of the capture compounds or collections thereof, to interact with the biomolecules or mixtures thereof, including, but not limited to specific receptors, to form covalent or non-covalent bonds with high affinity. In one embodiment, the capture compounds/collections thereof have a selectivity function, which is a COX-2 inhibitor, and a mixture of biomolecules contains COX receptors among other biomolecules.

The selectivity function Y, such as pharmaceutical drugs or drug fragments, can be attached to the central core Z, in different orientations via different points of attachment, thereby modulating the selectivity of the capture compound. The attachment of the selectivity function Y, such as a drug/ drug fragment to the central core can be carried out by methods known to a person with skill in the art.

In another embodiment, the capture compounds provided herein include those where the selectivity function is a drug, drug fragment, drug metabolite or a prodrug and the capture compounds also include a reactivity function, as described herein. In other embodiments, the capture compounds also include a sorting function, as described herein.

Selectivity function can interact noncovalently with target molecules, such as proteins, to alter the specificity or binding of the reactivity function. Such selectivity function moieties include chemical groups and biomolecules that can sterically hinder proteins of specific size, hydrophilic compounds or proteins (e.g., PEG and trityls), hydrophobic compounds or proteins (e.g., polar aromatic, lipids, glycolipids, phosphotriester, oligosaccharides), positively or negatively charged groups, and groups or molecules which create defined secondary or tertiary structure.

Exemplary selectivity functions include, but are not limited to, ligands that bind to receptors such as insulin and other receptors; cyclodextrins; enzyme substrates; lipid structures; prostaglandins; antibiotics; steroids; therapeutic drugs; enzyme inhibitors; transition state analogs; specific peptides that bind to biomolecule surfaces, including glue peptides; lectins (e.g., mannose type, lactose type); peptide mimetics; statins; functionalities, such as dyes and other compounds and moieties employed for protein purification and affinity chromatography. Other selections for Y are can be identified by those of skill in the art and include, for example, those disclosed in *Techniques in Protein Chemistry, Vol.* 1 (1989) T. Hugli ed. (Academic Press); *Techniques in Protein Chemistry, Vol.* 5 (1994) J. W. Crabb, ed. (Academic Press); Lundblad *Techniques in Protein Modification* (1995) (CRC Press, Boca Raton, Fla.); Glazer et al. (1976) *Chemical Modification of Proteins* (North Holland (Amsterdam)) (American Elsevier, N.Y.); and Hermanson (1996) *Bioconjugate Techniques* (Academic Press, San Diego, Calif.).

In some embodiments, the selectivity function interacts via non-covalent interactions with a protein e.g. in the active site of enzymes or ligand binding site of receptors ("Biased approach" for e.g. non-target identification), or at a surface affinity motif (SAM) outside of the binding site ("Unbiased approach" for e.g. target discovery). A biased selectivity group enables isolation of specific proteins from complex mixtures. In one embodiment, the selectivity function is a drug (or metabolite thereof) known to cause side effects, attached in several different orientations to make different parts of the molecule accessible to proteins. An unbiased selectivity function utilizes chemical features underlying affinity interactions with the protein surface. The unbiased selectivity function tends to be less specific than the biased, since it is designed to interact with a broader set of proteins. Use of the unbiased capture compounds to screen for global protein profile differences between healthy and disease cells would require the development of a library of capture compounds which as a set interact with the majority of the proteins in the proteome. This approach enables monitoring of protein profile differences induced by the influence of a drug molecule, or discovering new potential drug targets or biomarkers based on the differences between healthy with disease cells.

In certain embodiments, the capture compounds that contain a drug, drug fragment, drug metabolite or prodrug as a selectivity function moiety can include an amino acid core. In one embodiment, the amino acid core can be an amino acid that does not have a functionality on the side chain for attachment of a third function. Such amino acid cores include, but are not limited to, glycine, alanine, phenylalanine and leucine. In these embodiments, the capture compounds include a reactivity function and a selectivity function, which are attached to the amino and carboxy groups of the amino acid.

In another embodiment, the amino acid core may be an amino acid that possesses a functionality on the side chain for attachment of a third function. Such amino acid cores include, but are not limited to, serine, threonine, lysine, tyrosine and cysteine. In these embodiments, the capture compound includes a reactivity function, a sorting function and a selectivity function, which are attached to the amino, carboxy and side chain functional groups of the amino acid.

In one embodiment, the core is tyrosine and the capture compounds have the formula:

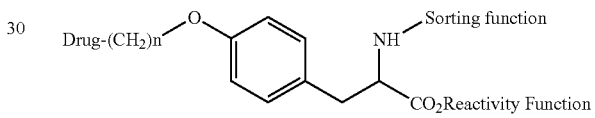

where "drug" refers to a drug, drug fragment, drug metabolite, drug intermediate or prodrug.

In one embodiment, the drug is LIPITOR® (atorvastatin calcium) and the capture compounds have the formulae:

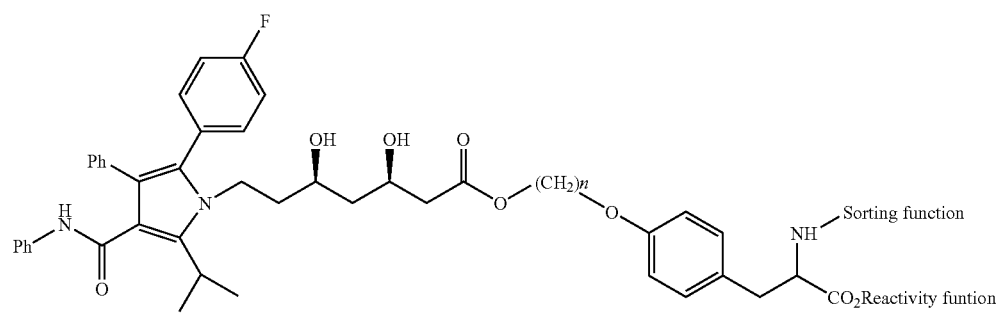

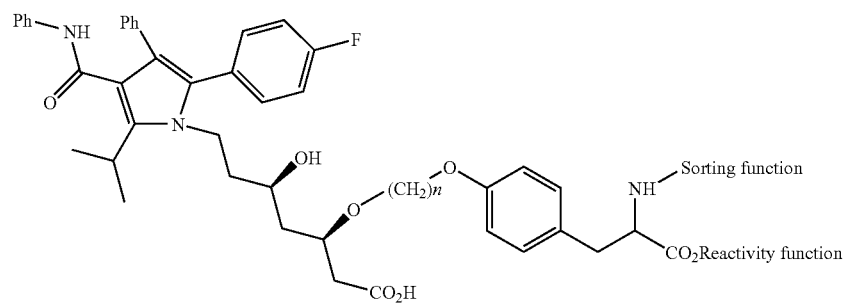

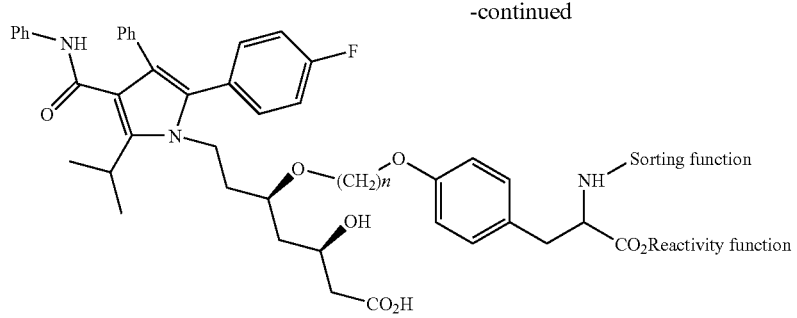
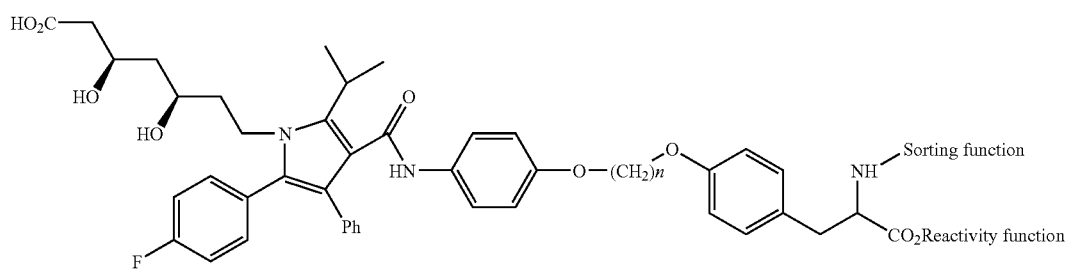
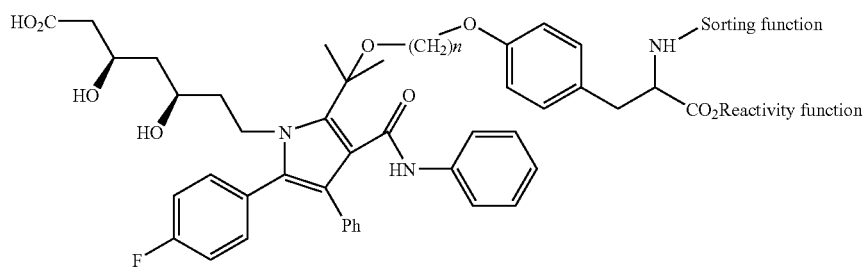
In other embodiments, the drug is CELEBREX® (celecoxib) and the capture compounds have the formulae:
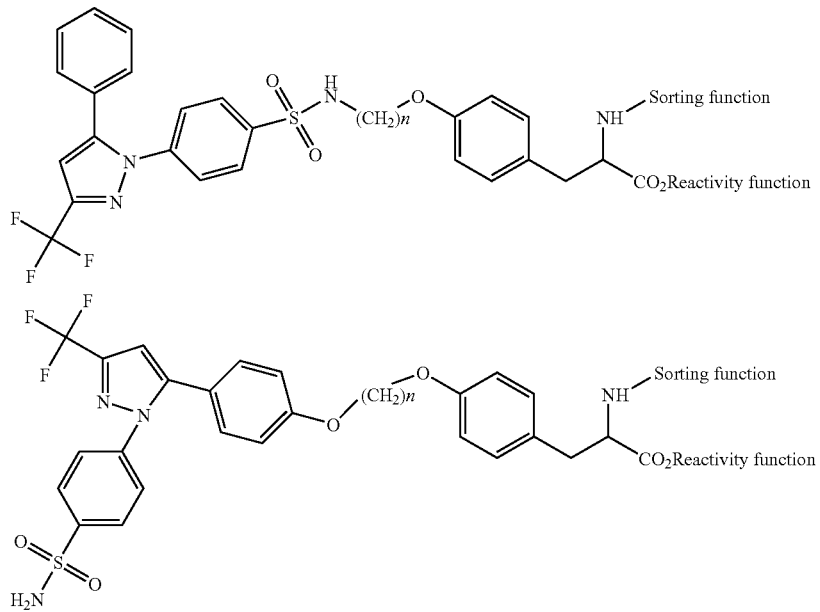

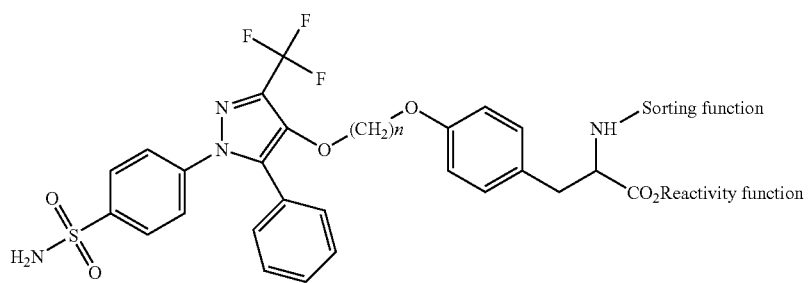
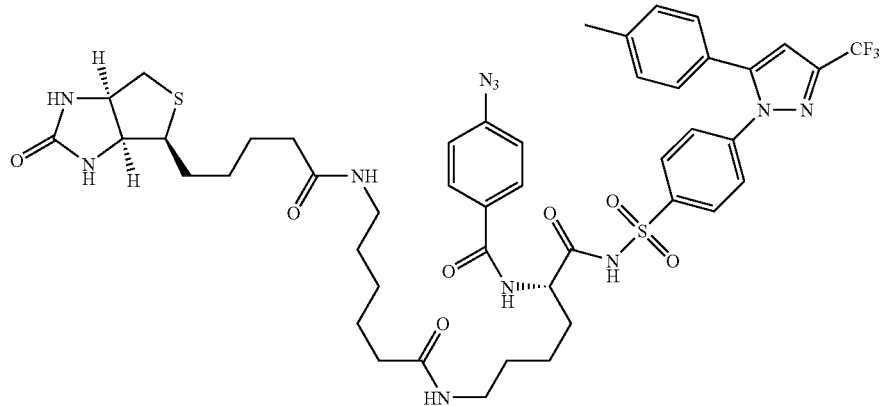
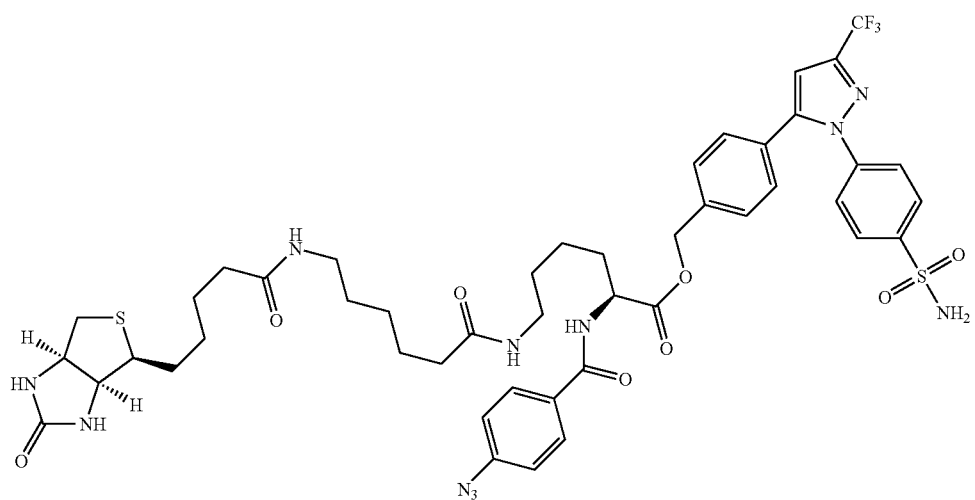
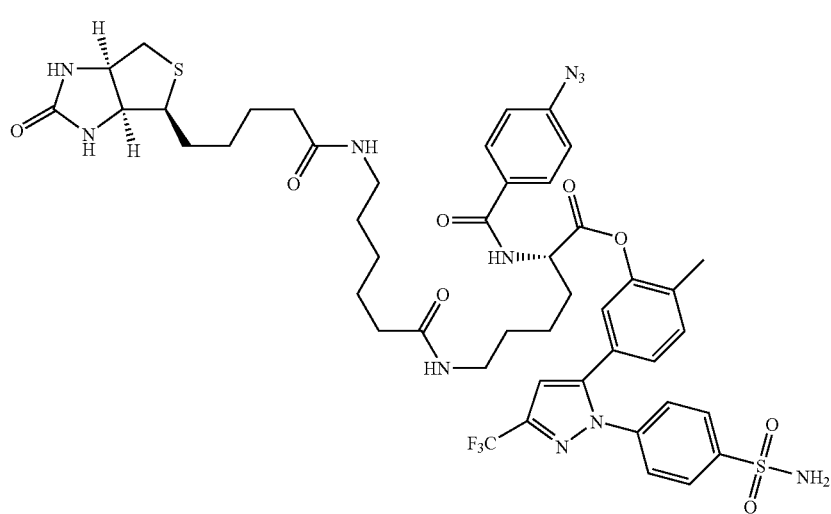

-continued
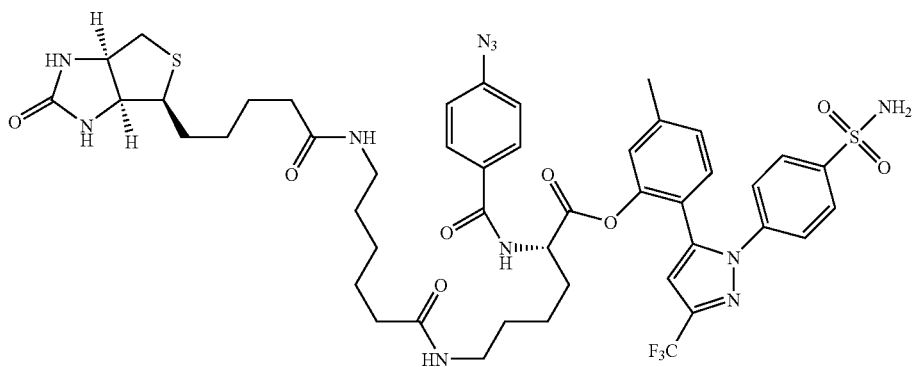
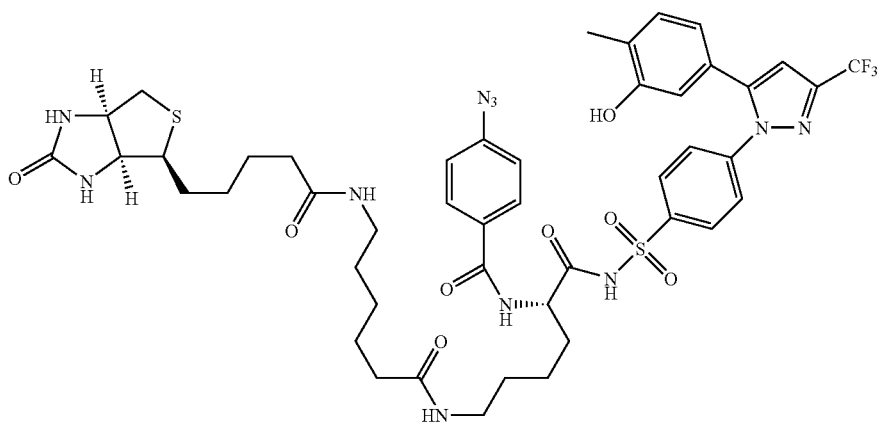
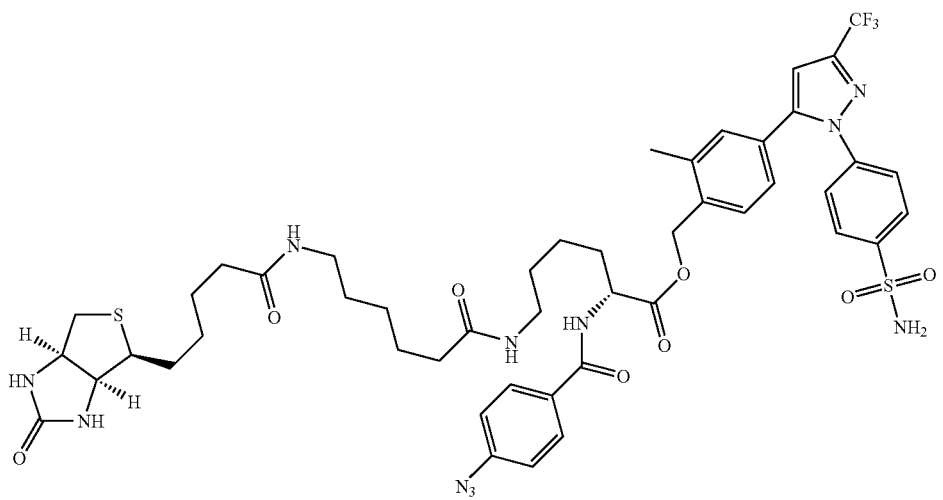

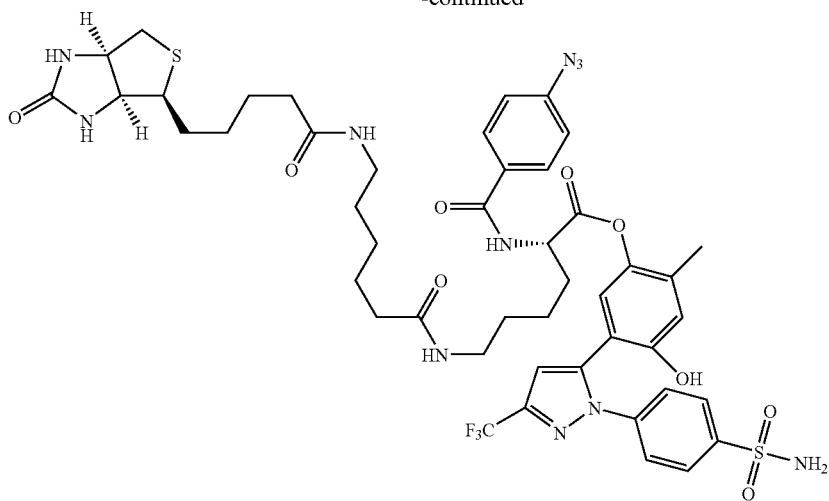
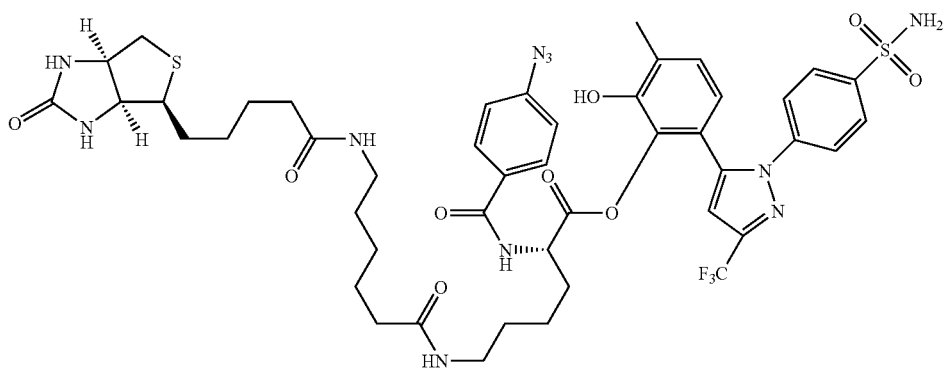
In another embodiment, the drug is VIOXX® (rofecoxib) and the capture compounds have the formulae:
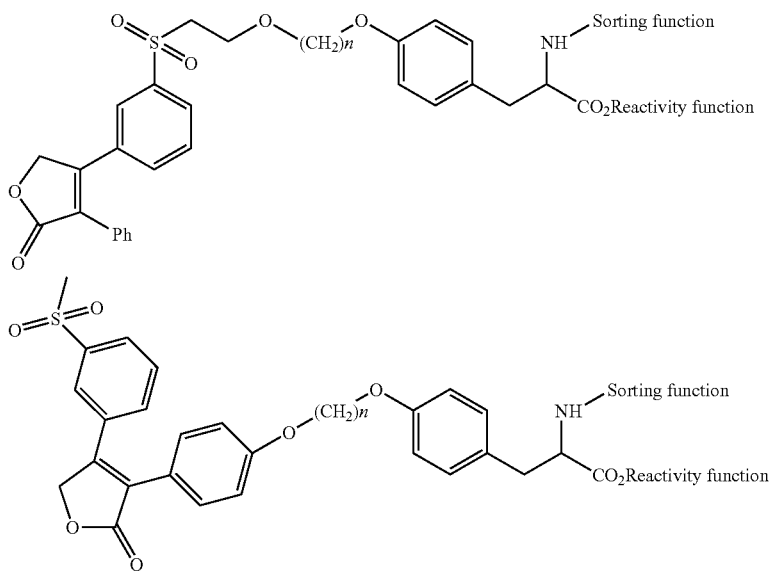

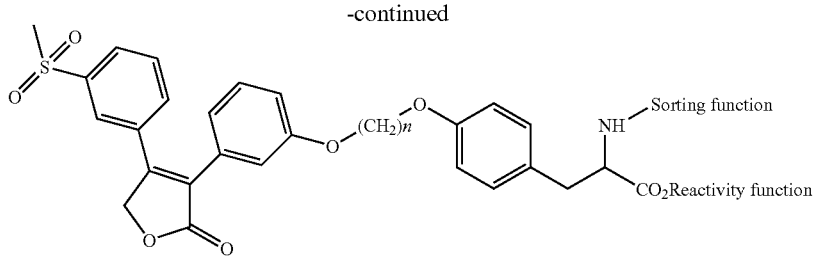
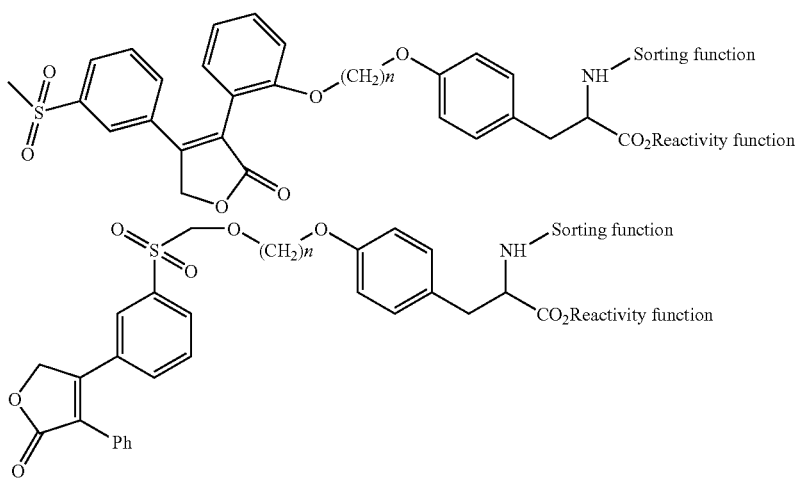
In another embodiment, the drug is BAYCOL® (cerivastatin sodium) and the capture compounds have the formula:
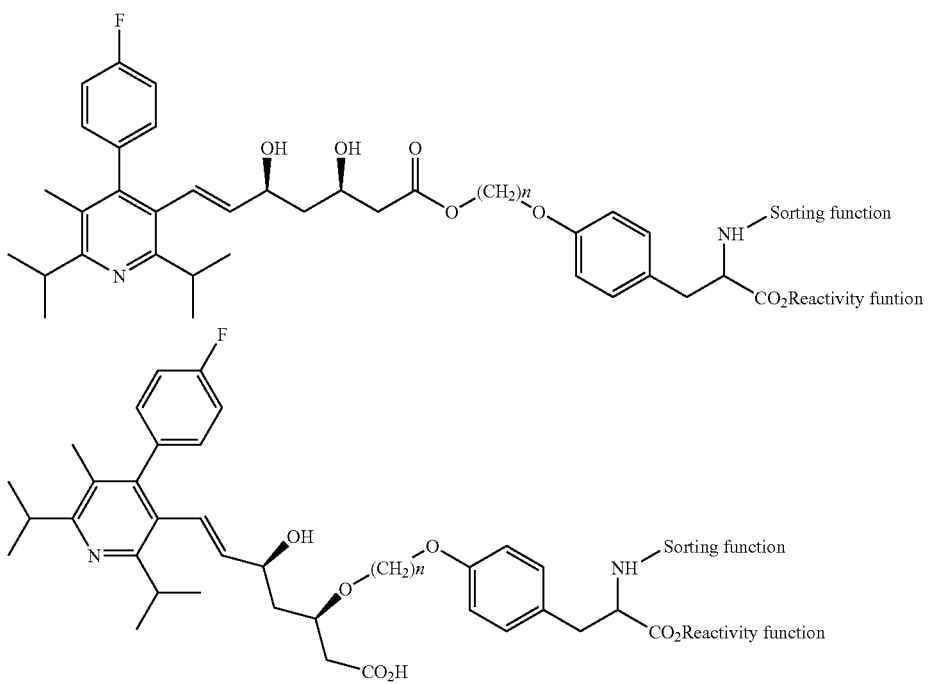

-continued
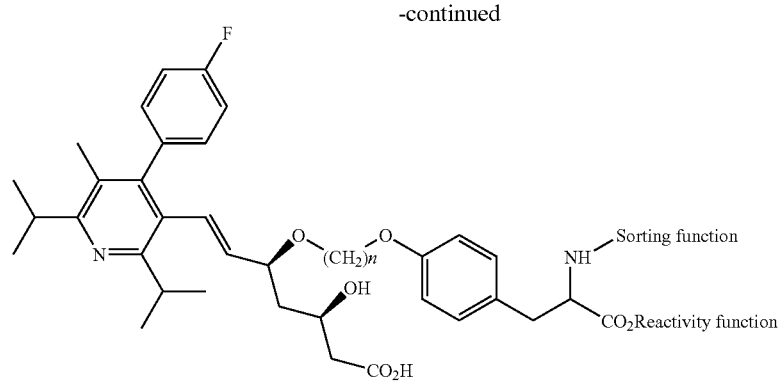
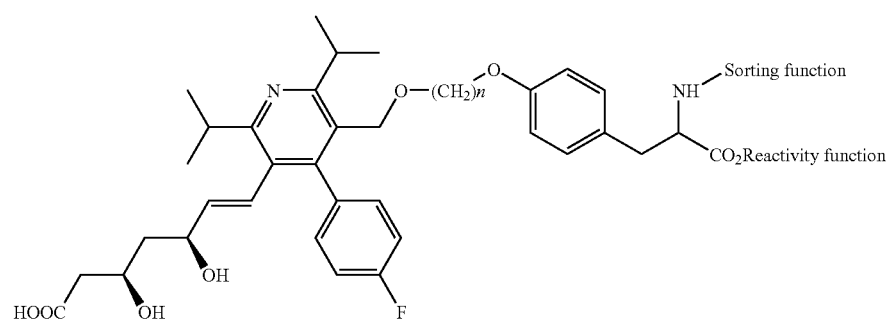
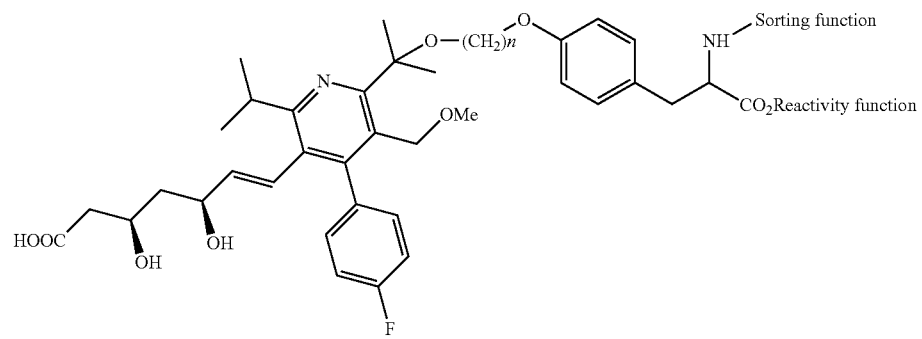
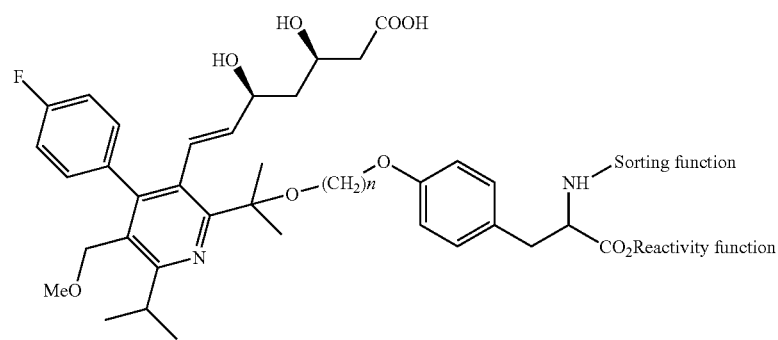

In another embodiment, the drug is methotrexate and the capture compounds have the formulae:
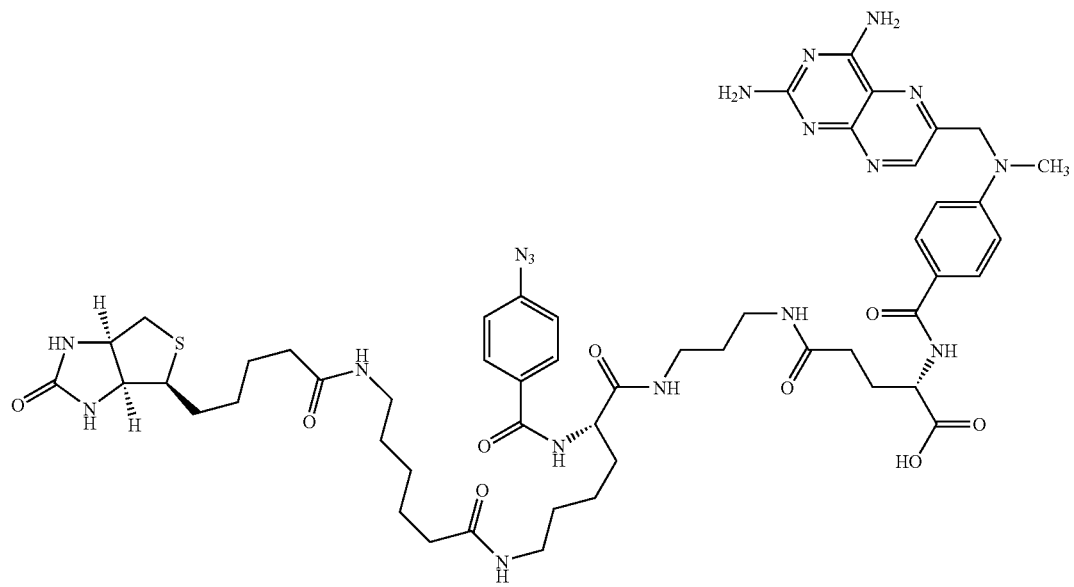
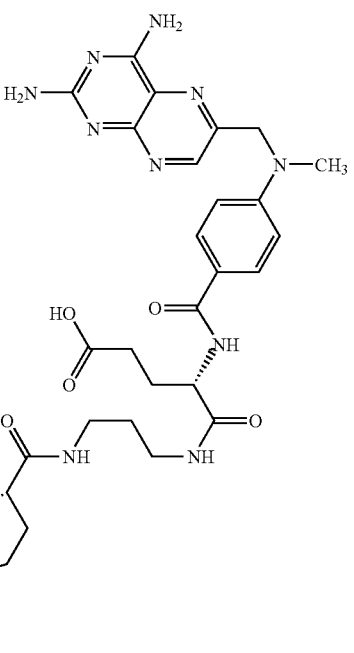

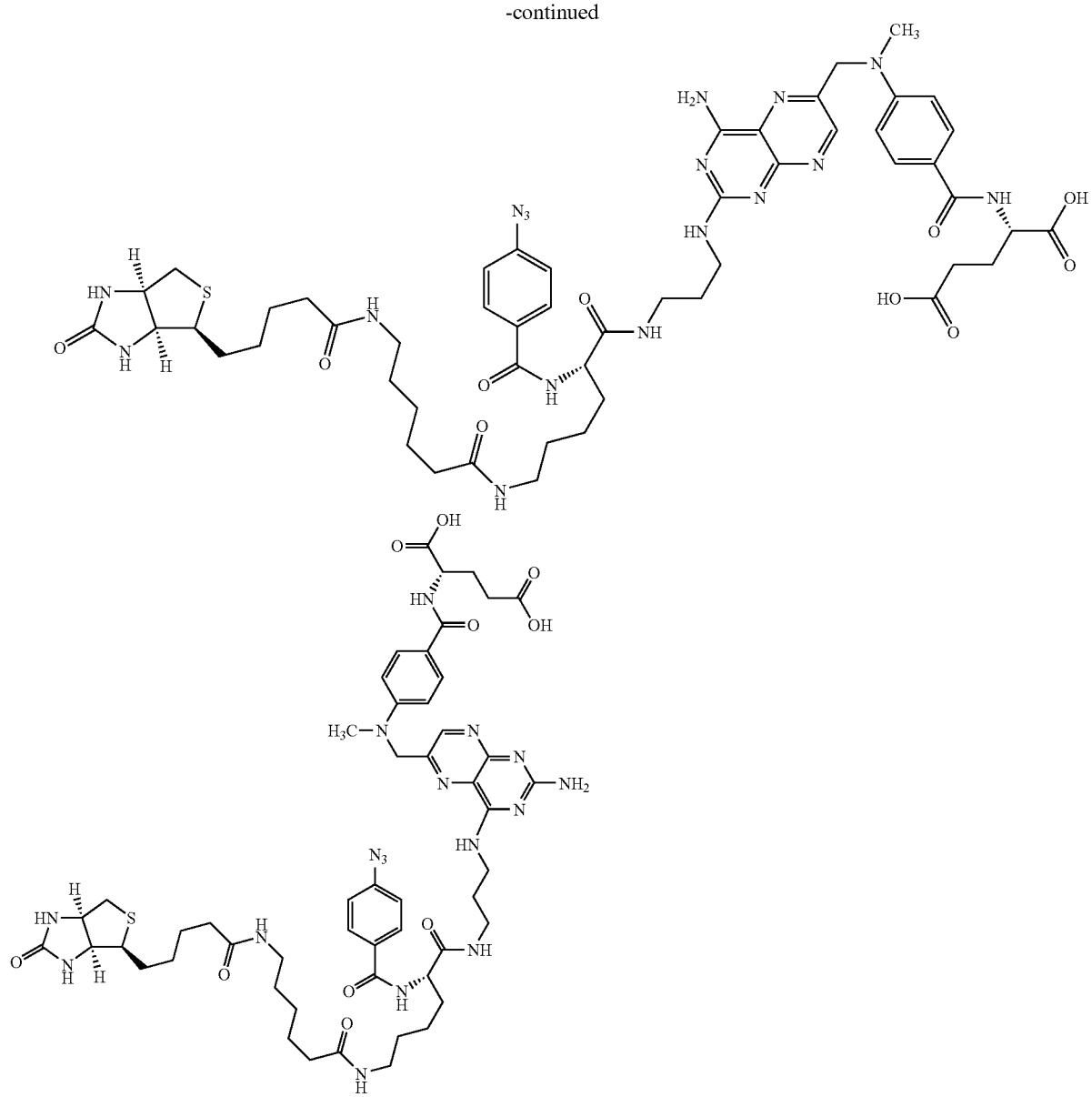

3. Sorting Function—Q

A sorting function is a moiety that binds either covalently or noncovalently to a specific molecule, such as a biomolecule, to permit separation or immobilization of the compounds, such as by separation at discrete loci on a solid support, or to allow identification or addressing of the target molecule. For example, the sorting function Q can permit the compounds to be addressed, such as by capture on a solid support, such as in a 2-D array. In certain embodiments, the sorting function is selected to not interact with certain molecules in a mixture (e.g., selected to interact with target molecules but not non-target molecule) in the sample.

In some embodiments, the sorting function, Q, is a group or moiety that provides a means for separating each set of capture compounds from the others, such as by arraying, and includes groups, such as one member of a specific binding pair, such as biotin, generally a spacer, binding to the other member of the specific binding pair, e.g., avidin on a surface.

In some embodiments, the sorting function Q is any molecule that has a cognate binding partner to which it binds with sufficient affinity to survive mass spectrometric analysis, such as MALDI-MS analysis, can be selected.

Exemplary sorting functions include one member of a specific binding pair, such as biotin and streptavidin, antibody and antigen, receptor and ligand, lectin and carbohydrate or other similar types of reagents (where the corresponding member of the binding pair is attached to a solid support, such as a magnetic particle) and nucleic acids or nucleic acid analogs that optionally include a single-stranded region that can specifically hybridize to a complementary single-stranded oligonucleotide or analog thereof. In some embodiments, the sorting function allows for the isolation of the specific protein from its complex cellular environment using a solid support (e.g., magnetic bead), enabling subsequent structural and functional characterization.

The well-known binding pairs are readily adaptable for use in the capture compounds as the sorting function Q. These moieties are selected so that the resulting conjugates (also referred to herein as complexes) have strong interactions that are sufficiently stable enough for suitable washing of the unbound molecules, including biomolecules, such as proteins, out of the complex biological mixtures.

Other sorting functions in the capture compounds for use in the methods provided herein include (His)$_6$, BODIPY (4,4-difluoro-4-bora-3a,4a-diaza-s-indacene), oligonucleotides, nucleosides, nucleotides, antibodies, immunotoxin conjugates, adhesive peptides, lectins, liposomes, PNA (peptide nucleic acid), activated dextrans and peptides. In one embodiment, the sorting function is an oligonucleotide, particularly, either a single-stranded or partially single-strained oligonucleotide to permit hybridization to single-stranded regions on complementary oligonucleotides on solid supports.

Mixtures of molecules, including biomolecules, such as protein mixtures, can have different hydrophobicities and/or solubilities than the capture compounds. In certain embodiments, in order to achieve high reaction yields between the reactivity function X on the capture compounds and, e.g., a protein surface, the reaction is performed in solution. In other embodiments, the reaction is performed at a solid/liquid or liquid/liquid interface. In certain embodiments, the solubility properties of the capture compounds are dominated by the sorting moiety Q. A change in the structure of the sorting moiety can, in these embodiments, accommodate different solubilities. For example, if a protein mixture is very water soluble, then the sorting function Q can have natural phosphodiester linkages; if the biomolecular mixture is very hydrophobic (lipids, glycolipids, membrane proteins, lipoproteins), then the sorting function Q can have it's phosphodiester bonds protected as phosphotriesters, or alternatively, these bonds can be methylphosphonate-diesters or peptide nucleic acids (PNAs). If the biomolecule mixture is of an intermediate hydrophobicity, solubility is achieved, e.g., with phosphothioate diester bonds. Intermediate solubility also can be attained by mixing phosphodiester with phosphotriester linkages. Those skilled in the art can easily conceive of other means to achieve this goal, including, but not limited to, addition of substituents on the core Z, such as solubility function W, as described elsewhere herein. The sorting function can be selectively cleavable to permit its removal.

In addition, the sorting function Q can be a labeling means that allows sorting by virtue of the label, such as fluorescent tags or color-coded tags. These can be readily sorted after reaction so that each set can be separately analyzed to identify bound molecules, such as biomolecules. For example, the capture compounds can include a fluorescent moiety as the sorting function, and the magnetic beads can include an antibody having specificity to the fluorescent moiety, allowing the capture compound to be sorted and attached on a surface of a magnetic bead by virtue of the anti-fluorescent moiety antibody on the beads. The collections can include capture compounds that have a variety of sorting functions Q. In some embodiments, Y is a group that is a component of a luminescent system, including a fluorescent, phosphorescent, chemiluminescent and bioluminescent system, or is a group that can be detected in a colorimetric assay; in certain embodiments, Y is a monovalent group selected from among straight or branched chain alkyl, straight or branched chain alkenyl, straight or branched chain alkynyl, cycloalkyl, cycloalkenyl, cycloalkynyl, heterocyclyl, straight or branched chain heterocyclylalkyl, straight or branched chain heterocyclylalkenyl, straight or branched chain heterocyclylalkynyl, aryl, straight or branched chain arylalkyl, straight or branched chain arylalkenyl, straight or branched chain arylalkynyl, heteroaryl, straight or branched chain heteroarylalkyl, straight or branched chain heteroarylalkenyl, straight or branched chain heteroarylalkynyl, halo, straight or branched chain haloalkyl, pseudohalo, azido, cyano, nitro, $OR^{60}$, $NR^{60}R^{61}$, $COOR^{60}$, $C(O)R^{60}$, $C(O)NR^{60}R^{61}$, $S(O)_qR^{60}$, $S(O)_qOR^{60}$, $S(O)_q NR^{60}R^{61}$, $NR^{60}C(O)R^{61}$, $NR^{60}C(O)NR^{60}R^{61}$, $NR^{60}S(O)_q R^{60}$, $SiR^{60}R^{61}R^{62}$, $P(R^{60})_2$, $P(O)(R^{60})_2$, $P(OR^{60})_2$, $P(O)(OR^{60})_2$, $P(O)(OR^{60})(R^{61})$ and $P(O)NR^{60}R^{61}$, where q is an integer from 0 to 2;

each $R^{60}$, $R^{61}$, and $R^{62}$ is independently hydrogen, straight or branched chain alkyl, straight or branched chain alkenyl, straight or branched chain alkynyl, aryl, straight or branched chain aralkyl, straight or branched chain aralkenyl, straight or branched chain aralkynyl, heteroaryl, straight or branched chain heteroaralkyl, straight or branched chain heteroaralkenyl, straight or branched chain heteroaralkynyl, heterocyclyl, straight or branched chain heterocyclylalkyl, straight or branched chain heterocyclylalkenyl or straight or branched chain heteorcyclylalkynyl.

Fluorescent, colorimetric and phosphorescent groups are known to those of skill in the art (see, e.g., U.S. Pat. No. 6,274,337; Sapan et al. (1999) *Biotechnol. Appl. Biochem.* 29 (*Pt.* 2):99-108; Sittampalam et al. (1997) *Curr. Opin. Chem. Biol.* 1(3):384-91; Lakowicz, J. R., Principles of Fluorescence Spectroscopy, New York: Plenum Press (1983); Herman, B., Resonance Energy Transfer Microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361 and the Molecular Probes Catalog (1997), OR, USA). Fluorescent moieties include, but are not limited to, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-amino-equilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolyl-phenylamine, 2-oxo-3-chromen, indole, xanthen, 7-hydroxycoumarin, phenoxazine, calicylate, strophanthidin, porphyrins, triarylmethanes and flavin. Fluorescent compounds that have functionalities for linking to a compound provided herein, or that can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-amino-aphthalene-6-sulfonate; ethidium bromide; stebrine; auromine-0,2-(9'-anthroyl)palmitate; dansyl phosphatidylethanolamine; N,N'-dioctadecyl oxacarbocyanine: N,N'-dihexyl oxacarbocyanine; merocyanine, 4-(3' pyrenyl)stearate; d-3-aminodesoxy-equilenin; 12-(9'-anthroyl)stearate; 2-methylanthracene; 9-vinylanthracene; 2,2'(vinylene-p-phenylene) bisbenzoxazole; p-bis(2-(4-methyl-5-phenyl-oxazolyl)) benzene; 6-dimethylamino-1,2-benzophenazin; retinol; bis (3'-aminopyridinium) 1,10-decandiyl diiodide; sulfonaphthyl-hydrazone of hellibrienin; chlorotetracycline; N-(7-dimethylamino-4-methyl-2-oxo-3-chromenyl)maleimide; N-(p-(2-benzimidazolyl)-phenyl)maleimide; N-(4-fluoranthyl)-maleimide; bis(homovanillic acid); resazarin; 4-chloro-7-nitro-2,1,3-benzooxadiazole; merocyanine 540; resorufin; rose bengal; and 2,4-diphenyl-3(2H)-furanone. Many fluorescent tags are commercially available from SIGMA chemical company (Saint Louis, Mo.), Molecular Probes, R&D systems (Minneapolis, Minn.), Pharmacia LKB Biotechnology. (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.) as well as other commercial sources known to one of skill in the art.

Chemiluminescent groups intended for use herein include any components of light generating systems that are catalyzed by a peroxidase and require superoxide anion (O) (and/or hydrogen peroxide ($H_2O_2$)) (see, e.g., Musiani et al. (1998) *Histol. Histopathol.* 13(1): 243-248). Lightgenerating systems include, but are not limited to, luminol, isoluminol, peroxyoxalate-fluorophore, acridinium ester, lucigenin, dioxetanes, oxalate esters, acridan, hemin, indoxyl esters including 3-O-indoxyl esters, naphthalene derivatives, such as 7-dimethylamino-naphthalene-1,2-dicarbonic acid hydrazide and cypridina luciferin analogs, including 2-methyl-6-[p-methoxyphenyl]-3,7-dihyroimidazo[1,2-a]pyrazin-3-one, 2-methyl-6-phenyl-3,7-dihyroimidazo[1,2-a]pyrazin-3-one and 2-methyl-6-[p-[2-[sodium 3-carboxylato-4-(6-hydroxy-3-xanthenon-9-yl]phenyl-thioureylene]ethyleneoxy]phenyl]-3,7-dihyroimidazo[1,2-a]pyrazin-3-one. In other embodiments, the chemiluminescent moieties intended for use herein include, but are not limited to, luminol, isoluminol, N-(4-aminobutyl)-N-ethyl isoluminol (ABEI) and N-(4-aminobutyl)-N-methyl isoluminol (ABMI).

Bioluminescent groups for use herein include luciferase/luciferin couples, including firefly [*Photinus pyralis*] luciferase, the *Aequorin* system (i.e., the purified jellyfish photoprotein, aequorin). Many luciferases and substrates have been studied and well-characterized and are commercially available (e.g., firefly luciferase is available from Sigma, St. Louis, Mo., and Boehringer Mannheim Biochemicals, Indianapolis, Ind.; recombinantly produced firefly luciferase and other reagents based on this gene or for use with this protein are available from Promega Corporation, Madison, Wis.; the aequorin photoprotein luciferase from jellyfish and luciferase from *Renilla* are commercially available from Sealite Sciences, Bogart, Ga.; coelenterazine, the naturally-occurring substrate for these luciferases, is available from Molecular Probes, Eugene, Oreg.]. Other bioluminescent systems include crustacean, such as *Cyrpidina* (*Vargula*), systems; insect bioluminescence generating systems including fireflies, click beetles, and other insect systems; bacterial systems; dinoflagellate bioluminescence generating systems; systems from molluscs, such as *Latia* and *Pholas*; earthworms and other annelids; glow worms; marine polycheate worm systems; South American railway beetle; fish (i.e., those found in species of *Aristostomias*, such as *A. scintillans* (see, e.g., O'Day et al. (1974) *Vision Res.* 14:545-550), *Pachystomias*, and *Malacosteus*, such as *M. niger*; blue/green emitters include cyclothone, myctophids, hatchet fish (agyropelecus), vinciguerria, howella, florenciella, and Chauliodus); and fluorescent proteins, including green (i.e., GFPs, including those from *Renilla* and from *Ptilosarcus*), red and blue (i.e., BFPs, including those from *Vibrio fischeri*, *Vibrio harveyi* or *Photobacterium phosphoreum*) fluorescent proteins (including *Renilla mulleri* luciferase, *Gaussia* species luciferase and *Pleuromamma* species luciferase) and phycobiliproteins.

4. Solubility Function—W

The solubility function, W, is a group or moiety that permits alteration in properties of the capture compound components. For example, W can be selected so that the capture compounds are soluble in a particular reaction medium or environment, such as a hydrophobic environment, thereby permitting reactions with membrane components.

Exemplary solubility functions for use in the compounds provided herein include polyethylene glycols, sulfates, polysulfates, phosphates, sulfonates, polysulfonates, carbohydrates, dextrin, polyphosphates, poly-carboxylic acids, triethanolamine, alcohols, water soluble polymers, salts of alkyl and aryl carboxylic acids and glycols. Amphiphilic compounds, such as quaternary ammonium salts (i.e., betaine, choline, sphingomyelin, tetramethyl (or tetrabutyl) alkyl ammonium salts, cationic, ionic and neutral tensides may also be used as the solubility function W.

In other embodiments, W also can be used to modulate the solubility of the compounds to achieve homogeneous solutions, if desired, when reacting with biomolecule mixtures, including, but not limited to, protein mixtures. In certain embodiments, W is a sulfonate, a polar functionality that can be used to make the compounds more water-soluble. In other embodiments, W is a hydrophobic group, including lower alkyl, such as tert-butyl, tert-amyl, isoamyl, isopropyl, n-hexyl, sec-hexyl, isohexyl, n-butyl, sec-butyl, iso-butyl and n-amyl, or an aryl group, including phenyl or naphthyl.

5. Core or Scaffold—Z

Generally, all capture compounds include a core or scaffold function, even if it is one atom, such as carbon, for presenting the functional groups. In certain embodiments of the capture compounds for use in the methods provided herein, Z is a moiety that is cleavable prior to or during analysis of the biomolecule, including mass spectral analysis, without altering the chemical structure of the molecule of interest, such as a biomolecule, including, but not limited to, a protein. In certain embodiments of the capture compounds for use in the methods provided herein, Z is a moiety that is not cleavable prior to or during analysis of the target molecule, such as a biomolecule.

In certain embodiments, Z is a difunctional moiety attached to a magnetic bead. In some embodiments, Z is a trifunctional moiety containing three functionalities. In some embodiments, Z is a trifunctional moiety containing three functionalities that are each capable of being derivatized selectively in the presence of the other two functionalities. Non-limiting examples of such trifunctional moieties include, but are not limited to, trifunctionalized trityl groups and amino acids that possess a functionality on the side chain (e.g., tyrosine, cysteine, aspartic acid, glutamic acid, lysine, threonine, serine, etc.). Such amino acids include natural and non-natural amino acids.

For example, in some embodiments, the selected or isolated molecules, such as biomolecules, are analyzed by mass spectrometry. In certain embodiments, the target molecules are bound to an array of single oligonucleotides that include single-stranded portions (or portions that can be made single-stranded) that are complementary to the oligonucleotide portions, or oligonucleotide analog portions, (Q, the sorting function) of the capture compounds. In these embodiments, Z can be selected to be a group that is (i) stable to the reaction conditions required for reaction of the capture compounds with the molecule of interest, such as a biomolecule, such as a protein, (ii) stable to the conditions required for hybridization of the Q moiety with the single stranded oligonucleotides, and (iii) cleavable prior to or during analysis of the molecule of interest.

In other embodiments, Z with the linked functional groups can be designed so that the capture compound partitions into lipid bilayers of a cell membrane, thereby contacting internal portions of cell membrane proteins through the X and Y functions. In this embodiment, the capture compound captures molecules of interest, such as biomolecules, including proteins, such as membrane proteins and organelle proteins, and proteins within cell membranes. The capture compounds and functional groups thereof can be selected so that the resulting capture compounds function under selected physiological conditions. Thus, the choice of Z, Q, X, W and/or Y allows for design of surfaces and supports that mimic cell membranes and other biological membranes.

In some embodiments, a lipid bilayer, such as those used for forming liposomes and other micelles, can be provided on the surface of a solid support, such as a magnetic bead, as a way of maintaining the structures of membrane proteins to make a lipid bilayer on the surface. This can be used where the capture compounds are linked to a support, such as a magnetic particle, through a Q group, such as by double-stranded oligonucleotides, or where Q is one member of a specific binding pair, where the other member of the binding pair is attached to the magnetic particle. The resulting immobilized capture compounds can be coated with or dissolved in a lipid coating. As a result, the capture compounds and collections thereof can act as an artificial membrane, dendrimer polymer chemistry can be employed for controlled synthesis of membranes having consistent pore dimensions and membrane thicknesses, through synthesis of amphiphilic dendrimeric or hyperbranched block copolymers that can be self-assembled to form ultrathin organic film membranes on porous supports. In one embodiment, an organic film membrane is composed of a linear-dendritic di-block copolymer composed of polyamidoamine (PAMAM) dendrimer attached to one end of a linear polyethylene oxide (PEO) block. In certain embodiments, Z is alkylene, phenylene, biphenylene or a multivalent or divalent heterobifunctional trityl derivative. Z can be unsubstituted or can be substituted with 1 to 4 groups, each independently selected from $R^{15}$, where $R^{15}$ is selected from among H, OH, $OR^{51}$, SH, $SR^{51}$, $NH_2$, $NHR^{51}$, $NR^{51}_2$, F, Cl, Br, I, $SO_3H$, $PO^2_4$, $CH_3$, $CH_2CH_3$, $CH(CH_3)_2$ or $C(CH_3)_3$; where $R^{51}$ is straight or branched chain alkyl, straight or branched chain alkenyl, straight or branched chain alkynyl, aryl, heteroaryl, cycloalkyl, heterocyclyl, straight or branched chain aralkyl, straight or branched chain aralkenyl, straight or branched chain aralkynyl, straight or branched chain heteroaralkyl, straight or branched chain heteroaralkenyl, straight or branched chain heteroaralkynyl, straight or branched chain cycloalkylalkyl, straight or branched chain cycloalkylalkenyl, straight or branched chain cycloalkylalkynyl, straight or branched chain heterocyclylalkyl, straight or branched chain heterocyclylalkenyl or straight or branched chain heterocyclylalkynyl.

a. Z is Cleavable Under the Conditions of Mass Spectrometric Analysis

In one such embodiment, Z is a photocleavable group that is cleaved by a laser used in MALDI-TOF mass spectrometry. In another embodiment, Z is an acid labile group that is cleaved upon application of a matrix for mass spectrometric analysis to arrayed, such as hybridized compound-biomolecule conjugates, or by exposure to acids (e.g., trifluoroacetic or hydrochloric acids) in a vapor or liquid form, prior to analysis. In this embodiment, the matrix maintains the spacial integrity of the array, allowing for addressable analysis of the array.

b. Z is not Cleavable Under the Conditions of Mass Spectrometric Analysis

In certain embodiments, the capture compounds for use in the methods provided herein have a Z moiety that is not cleavable under conditions used for analysis of biomolecules, including, but not limited to, mass spectrometry, such as matrix assisted laser desorption ionization-time of flight (MALDI-TOF) mass spectrometry. Capture compounds of these embodiments can be used, for example, in methods provided herein for identifying biomolecules in mixtures thereof, for determining biomolecule-biomolecule, including protein-protein, interactions, and for determining biomolecule-small molecule, including protein-drug or protein-drug candidate, interactions. In these embodiments, it is not necessary for the Z group to be cleaved for the analysis.

Thus, as noted, Z can be virtually any moiety that serves as a core or scaffold to present functional groups of the capture compounds, such as the binding (the selectivity and reactivity functions) and the solubility and sorting functions. A variety of core function Zs are exemplified herein, but others may be substituted. The core Z can be a matter of design choice in view of the disclosure herein and the skill of the skilled artisan The capture compounds can include a core Z that has a variety of valencies. Among the capture compounds are those in which Z is at least trivalent. Also among the capture compounds, alone or in collections thereof, are those where Z is divalent and linked to either a Q and an X, or a Q and a Y, or an X and a Y, or a Q and an X and a Y and a W, or other combination of the functionalities provided herein.

6. Optional Spacer Moiety—E

The capture compounds also optionally can include one or more spacer moieties E that can be present between the core Z and any or all attached functional groups. A spacer moiety E can be selected that, for example, reduces steric hindrance in reactions with the surface of large molecules, such as biomolecules, and/or for facilitating sorting. The spacer moiety E can be any group or moiety that provides for spacing, typically without altering desired functional properties of the capture compounds and/or capture compound/molecule complexes. Those of skill in the art, in light of the disclosure herein, can readily select suitable spacers. Exemplary spacers are set forth below.

In some embodiments, such as where the molecule of interest and the sorting function possess low steric hindrance, a spacer is optional. In certain embodiments, steric hindrance also can enhance selectivity in conjunction with selectivity function Y (or in the absence of a Y moiety). This enhanced selectivity can be achieved either by the presence of a selectivity function, Y, that is attached to Z or by the selection of the appropriate spacer moiety E. In other embodiments, the spacer moiety E is selected such that the selectivity function reaches the targeted area of the molecule of interest, such as a binding pocket of a target or non-target protein. Spacer moieties can be hydrophilic (e.g., PEGs or phosphodiesters) or hydrophobic; their length may be varied to achieve efficient sorting or selectivity or capture; and/or they may be rigid (e.g., trans olefins, C—C triple bond). The spacer moiety E can be selected based on the properties (hydrophobic/hydrophilic, size, etc.) of the reaction mixture or sample, such as a biological sample, to be analyzed. In some embodiments, the spacer moiety E can be a solubility function W.

7. Optional Cleavable Linker—L

The capture compounds provided herein also optionally include a cleavable linker or bond L between the core Z and any or all attached functional groups. The reactivity of the cleavable linker or bond can be influenced by one or more substituted functionalities, for example, $R^{15}$ on Z. Electronic (e.g., mesomeric, inductive) and/or steric effects can be used to modulate the stability of the cleavable bond L. For example, if Z is a trityl derivative, the linkage to the biomolecule, including, but not limited to, a protein, is in one embodiment a trityl ether bond. The sensitivity of this bond to mild acids, such as acetic acid or the vapor of trifluoroacetic acid, can be significantly enhanced by having as $R^{15}$ one or two electron donating groups, including, but not limited to, alkoxy groups, such as methoxy groups, in the para positions of the aryl rings. Alternatively, the trityl ether bond can be stabilized by the introduction of electron withdrawing groups, including, but not limited to, either halogen, including bromo and chloro, groups, nitro groups or ester moieties, in the para and/or ortho positions of the aromatic rings.

In certain embodiments, $S^P$ is selected from among $(CH_2)_r$, $(CH_2O)$, $(CH_2CH_2O)$, $(NH(CH_2)_rC(=O))_s$, $(NHCH(R^{52})C(=O))_s$, $(O(CH)_rC(=O))_s$,

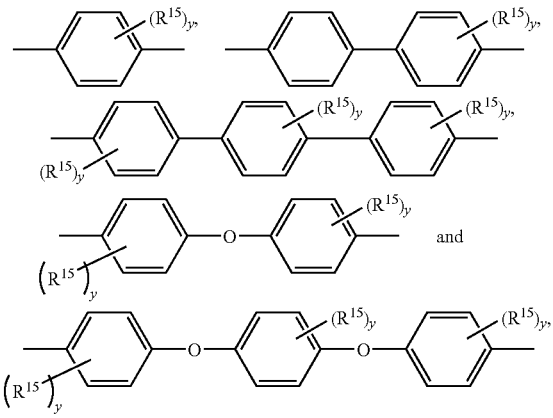

where $R^{15}$ is selected as above; r and s each independently is an integer from 1 to 10; $R^{52}$ is the side chain of a natural α-amino acid; and y is an integer from 0 to 4. In one embodiment, y is 0 or 1.

In certain embodiments, the cleavable linker or bond L is cleaved either prior to or during analysis of the molecule, such as a biomolecule, such as a protein. The analysis can include mass spectral analysis, for example MALDI-TOF mass spectral analysis. The cleavable group L is selected so that the group is stable during conjugation to a molecule of interest, such as a biomolecule, and during sorting, such as hybridization of a single stranded oligonucleotide Q moiety to a complementary sequence, and washing of the hybrid; but is susceptible to cleavage under conditions of analysis of the molecule, including, but not limited to, mass spectral analysis, for example MALDI-TOF analysis. In certain embodiments, the cleavable group L can be a disulfide moiety, created by reaction of the compounds where X=SH, with the thiol side chain of cysteine residues on the surface of biomolecules, including, but not limited to, proteins. The resulting disulfide bond can be cleaved under various reducing conditions including, but not limited to, treatment with dithiothreitol and 2-mercaptoethanol.

In another embodiment, L is a photocleavable group, which can be cleaved by a short treatment with UV light of the appropriate wave length either prior to or during mass spectrometry. Photocleavable groups, including those bonds that can be cleaved during MALDI-TOF mass spectrometry by the action of a laser beam, can be used. For example, a trityl ether or an ortho nitro substituted aralkyl, including benzyl, group are susceptible to laser induced bond cleavage during MALDI-TOF mass spectrometry. Other useful photocleavable groups include, but are not limited to, o-nitrobenzyl, phenacyl, and nitrophenylsulfenyl groups.

Other photocleavable groups for use herein include those disclosed in U.S. Pat. No. 7,198,893 and International Patent Application Publication No. WO 98/20166. In one embodiment, the photocleavable groups have formula I:

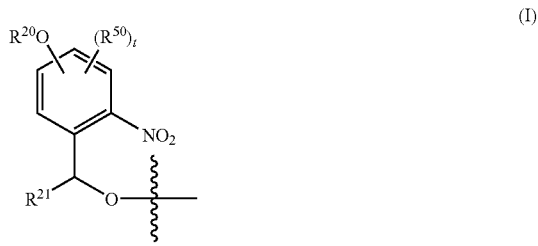

where $R^{20}$ is ω-hydroxy-alkylene; $R^{21}$ is selected from hydrogen, alkyl, aryl, alkoxycarbonyl, aryloxycarbonyl and carboxy; t is 0-3; and $R^{50}$ is alkyl, alkoxy, aryl or aryloxy. In one embodiment, Q is attached to $R^{20}$ through a linking moiety and the biomolecule of interest is captured onto the $R^{21}$CHO moiety via a reactive derivative of the oxygen (e.g., X).

In another embodiment, the photocleavable groups have formula II:

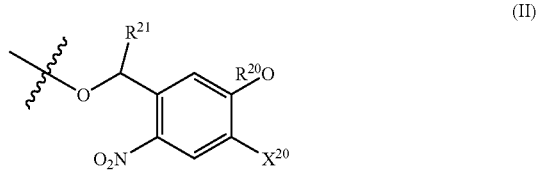

where $R^{20}$ is ω-hydroxyalkylene or alkylene; $R^{21}$ is selected from hydrogen, alkyl, aryl, alkoxycarbonyl, aryloxycarbonyl and carboxy; and $X^{20}$ is hydrogen, alkyl or $OR^{21}$. In one embodiment, Q is attached to $R^{20}$ through a linking moiety; and the biomolecule of interest is captured onto the $R^{21}$CHO moiety via a reactive derivative of the oxygen (e.g., X).

In some embodiments, $R^{20}$ is $O(CH_2)_3$ or methylene; $R^{21}$ is selected from hydrogen, methyl and carboxy; and $X^{20}$ is hydrogen, methyl or $OR^{21}$. In other embodiments, $R^{21}$ is methyl; and $X^{20}$ is hydrogen. In some embodiments, $R^{20}$ is methylene; $R^{21}$ is methyl; and $X^{20}$ is 3-(4,4'-dimethoxytrityloxy)propoxy.

In another embodiment, the photocleavable groups have formula III:

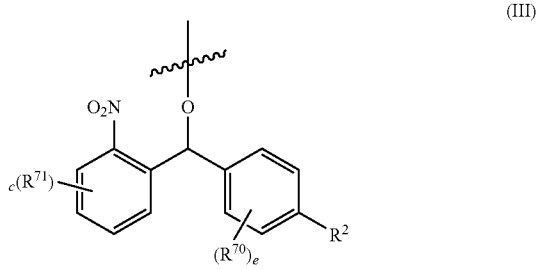

where $R^2$ is selected from ω-hydroxyalkylenehydroxy and ωhydroxyalkylene, and is unsubstituted or substituted on the alkylene chain with one or more alkyl groups; c and e are each independently 0-4; and $R^{70}$ and $R^{71}$ are each independently alkyl, alkoxy, aryl or aryloxy. In certain embodiments, $R^2$ is ω-hydroxyalkylene, and is substituted on the alkylene chain with a methyl group. In one embodiment, Q is attached to $R^2$ through a linking moiety; and the biomolecule of interest is captured onto the Ar$_2$CHO moiety via a reactive derivative of the oxygen (e.g., X).

In some embodiments, R$^2$ is selected from among 3-hydroxy(CH$_2$)$_3$O, 4-hydroxy(CH$_2$)$_4$, 3-hydroxy-(CH$_2$)$_3$, 2-hydroxy-CH$_2$CH$_2$, OCH$_2$,

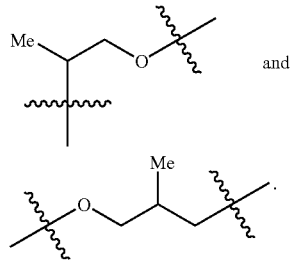

and

In other embodiments, c and e are 0.

Other cleavable linker or bond L moieties include acid sensitive groups, where bond cleavage is promoted by formation of a cation upon exposure to mild to strong acids. For these acid-labile groups, cleavage of the group L can be effected either prior to or during analysis, including mass spectrometric analysis, by the acidity of the matrix molecules, or by applying a short treatment of the array with an acid, such as the vapor of trifluoroacetic acid. Exposure of a trityl group to acetic or trifluoroacetic acid produces cleavage of the ether bond either before or during MALDI-TOF mass spectrometry.

The capture compound-biomolecule array can be treated by either chemical or enzymatic reagents to effect cleavage. For example, treatment with cyanogen bromide will result in chemical cleavage. In embodiments where the biomolecule is a protein, treatment with trypsin, chymotrypsin and/or an exopeptidase (e.g., aminopeptidase and carboxypeptidase) enzyme will effect enzymatic cleavage. Partial digestion also can be of advantage to identify and characterize proteins following desorption from the array. During MALDI-TOF mass spectrometry, the cleaved protein/peptide fragments are desorbed, analyzed, and characterized by their respective molecular weights.

7. Optional Mass Modifying Tags

In other embodiments, core Z includes a mass modifying tag. A mass modifying tag is any moiety that modifies the mass of a molecule to which it is attached, thereby allowing differentiating during analysis by mass spectrometry. In certain embodiments, the mass modifying tag is attached to the cleavable linker L. Mass modifying tags for use herein include, but are not limited to, groups of formula X$^1$R$^{10}$, where X$^1$ is a divalent group such as O, OC(O)(CH$_2$)$_y$C(O)O, NHC(O), C(O)NH, NHC(O)(CH$_2$)$_y$C(O)O, NHC(S)NH, OP(O-alkyl)O, OSO$_2$O, OC(O)CH$_2$S, S, NH and 1,3,3,4-tetramethyl-4-(methylthio)pyrrolidine-2,5-dione, and R$^{10}$ is a divalent group selected from among alkylene, alkenylene, alkynylene, (CH$_2$CH$_2$O)$_z$CH$_2$CH$_2$O, (CH$_2$CH$_2$O)$_n$CH$_2$CH$_2$O-alkylene, arylene, heteroarylene, (CH$_2$)$_z$CH$_2$O, (CH$_2$)$_z$CH$_2$Oalkylene, (CH$_2$CH$_2$NH)$_z$CH$_2$CH$_2$NH, CH$_2$CH(OH)CH$_2$O, Si(R$^{12}$)(R$^{13}$), CHF and CF$_2$; where y is an integer from 1 to 20; z is an integer from 0 to 200; R$^{11}$ is the side chain of an α-amino acid; and R$^{12}$ and R$^{13}$ are each independently selected from alkyl, aryl and aralkyl. In other embodiments, the mass tag is selected from among SS, S, (NH(CH$_2$)$_y$NHC(O)(CH$_2$)$_y$C(O))$_z$NH(CH$_2$)$_y$NHC(O)(CH$_2$)$_y$C(O)O, (NH(CH$_2$)$_y$C(O))$_z$NH(CH$_2$)$_y$C(O)O, (NHCH(R$^{11}$)C(O))$_z$NHCH(R$^{11}$)C(O)O, and (O(CH$_2$)$_y$C(O))$_z$NH(CH$_2$)$_y$C(O)O.

In the above embodiments, where R$^{10}$ is an oligo-/polyethylene glycol derivative, the mass-modifying increment is 44, i.e., five different mass-modified species can be generated by changing z from 0 to 4, thus adding mass units of 45 (z=0), 89 (z=1), 133 (z=2), 177 (z=3) and 221 (z=4) to the compounds. The oligo/polyethylene glycols also can be monoalkylated by a lower alkyl such as methyl, ethyl, propyl, isopropyl, t-butyl and the like.

Other mass modifying tags include, but are not limited to CHF, CF$_2$, Si(CH$_3$)$_2$, Si(CH$_3$)(C$_2$H$_5$) and Si(C$_2$H$_5$)$_2$. In other embodiments, the mass modifying tags include homo- or heteropeptides. A non-limiting example that generates mass-modified species with a mass increment of 57 is an oligoglycine, which produce mass modifications of, e.g., 74 (y=1, z=0), 131 (y=1, z=2), 188 (y=1, z=3) or 245 (y=1, z=4). Oligoamides also can be used, e.g., mass-modifications of 74 (y=1, z=0), 88 (y=2, z=0), 102 (y=3, z=0), 116 (y=4, z=0), etc., are obtainable. Those skilled in the art will appreciate that there are numerous possibilities in addition to those exemplified herein for introducing, in a predetermined manner, many different mass modifying tags to the compounds provided herein.

In other embodiments, R$^{15}$ and/or S$^2$ can be functionalized with X$^1$R$^{10}$H or X$^1$R$^{10}$alkyl, where X$^1$ and R$^{10}$ are defined as above, to serve as mass modifying tags.

9. Exemplary Capture Compounds

In another embodiment, the capture compounds for use in the methods provided herein include those of formulae:

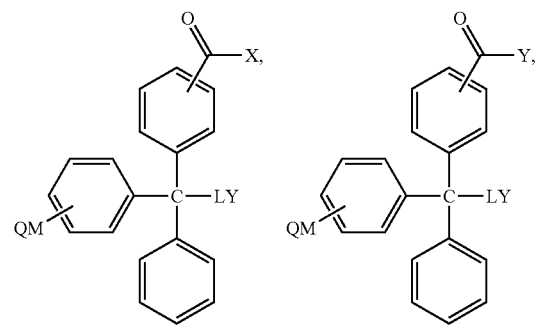

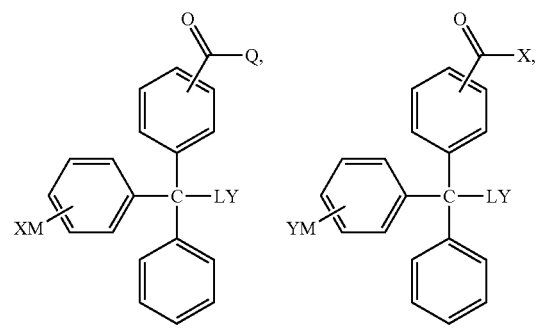

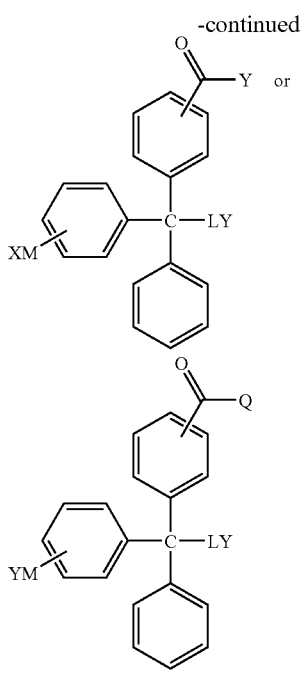

where L and M are each independently O, S or $NR^3$; X is a reactivity function, as described above; Y is a selectivity function, as described above; Q is a sorting function, as described above; and each $R^3$ is independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl.

In another embodiment, the capture compounds provided herein have the formula:

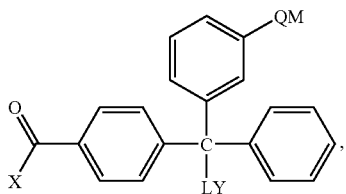

where L, M, X, Y and Q are as defined above.

In another embodiment, the capture compounds provided herein have the formula:

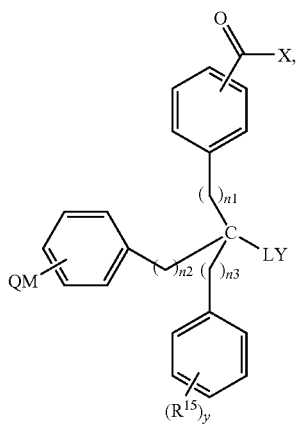

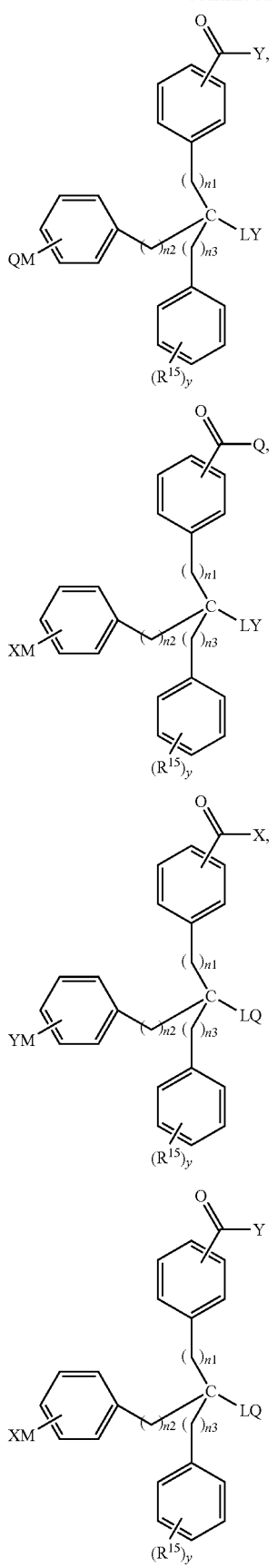

-continued

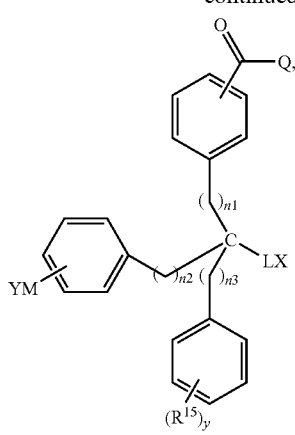

where L, M, X, Y and Q are as defined above, n1, n2 and n3 are 0 to 5. In another embodiment, n1, n2 and n3 are selected with the proviso that n1, n2 and n3 are not all 0.

In another embodiment, the capture compounds provided herein have the formula:

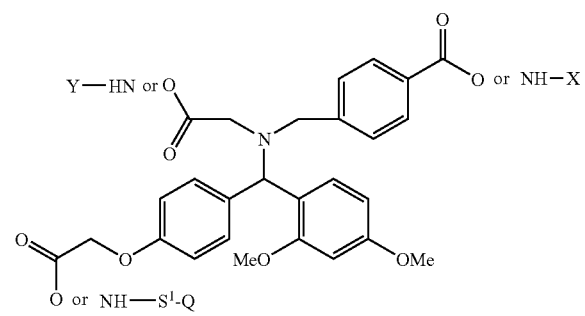

where X, Y, Q and $S^1$ are as defined above.

In another embodiment, the capture compounds provided herein have the formula:

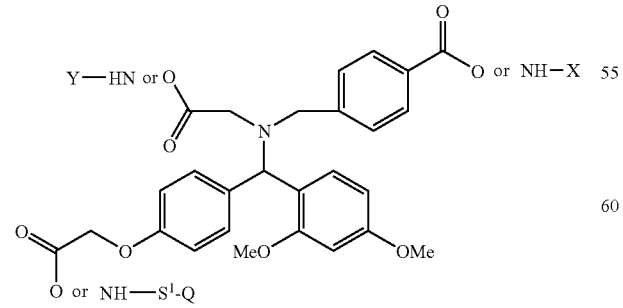

where Q, Y, X and $S^1$ are as defined above.

In another embodiment, the capture compounds provided herein have the formula:

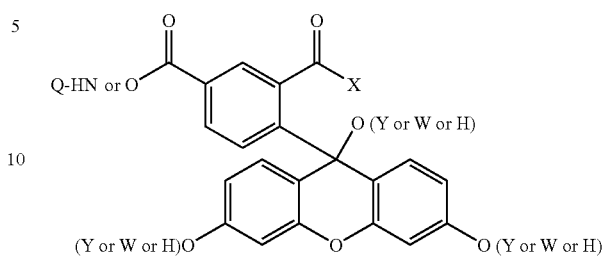

where X, Y, Q and W are as defined above.

In another embodiment, the capture compounds provided herein have the formula:

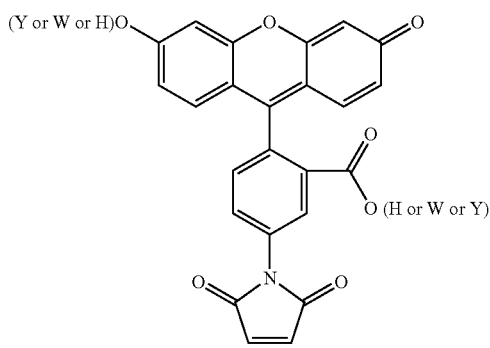

where X, Y, Q and W are as defined above.

In another embodiment, the capture compounds for use in the methods provided herein have the formulae:

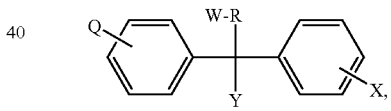

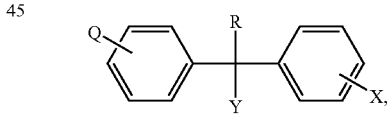

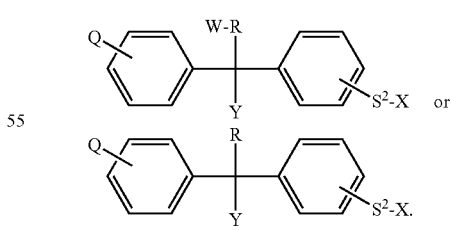

where X, Y, Q and W are selected as above; and R is substituted or unsubstituted alkyl, substituted or unsubstituted cycloalkyl, substituted or unsubstituted cycloalkylalkyl, or substituted or unsubstituted aralkyl. In another embodiment, R is selected from cyclohexyl, cyclohexyl-$(CH_2)$—, isopropyl, and phenyl-$(CH_2)$—, where n is 1, 2 or 3. As shown in the formulae above, R is optionally substituted with W.

In other embodiments, the capture compounds for use in the methods provided herein include:
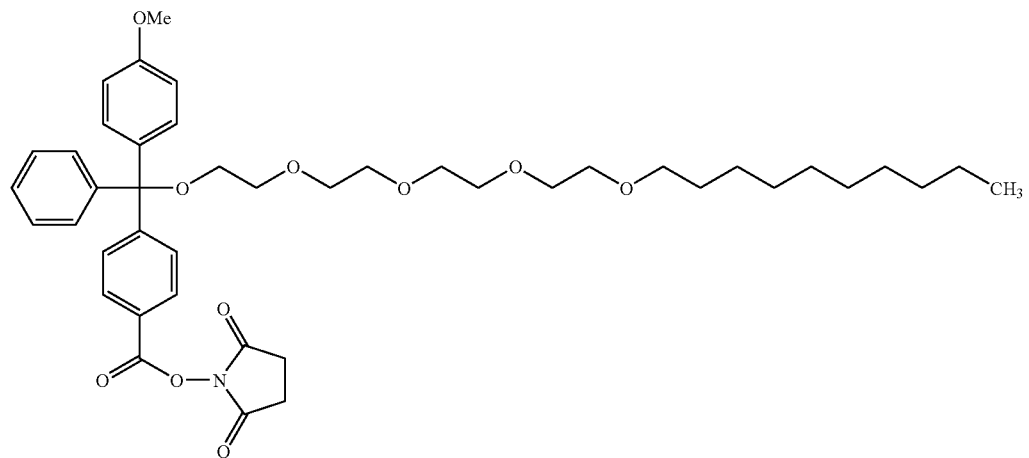
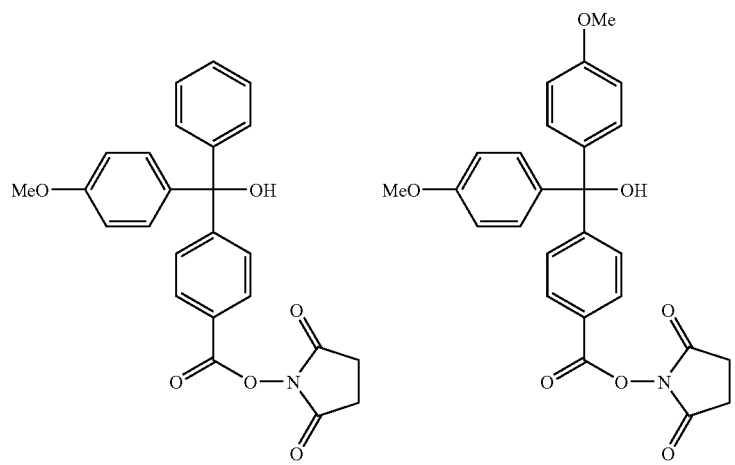
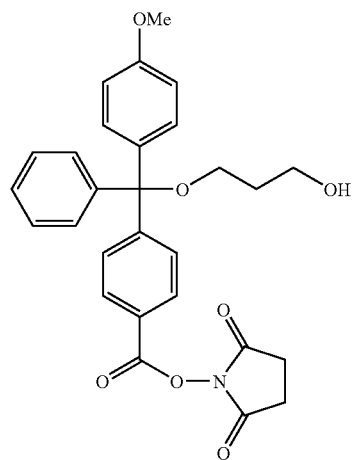

91
92
-continued
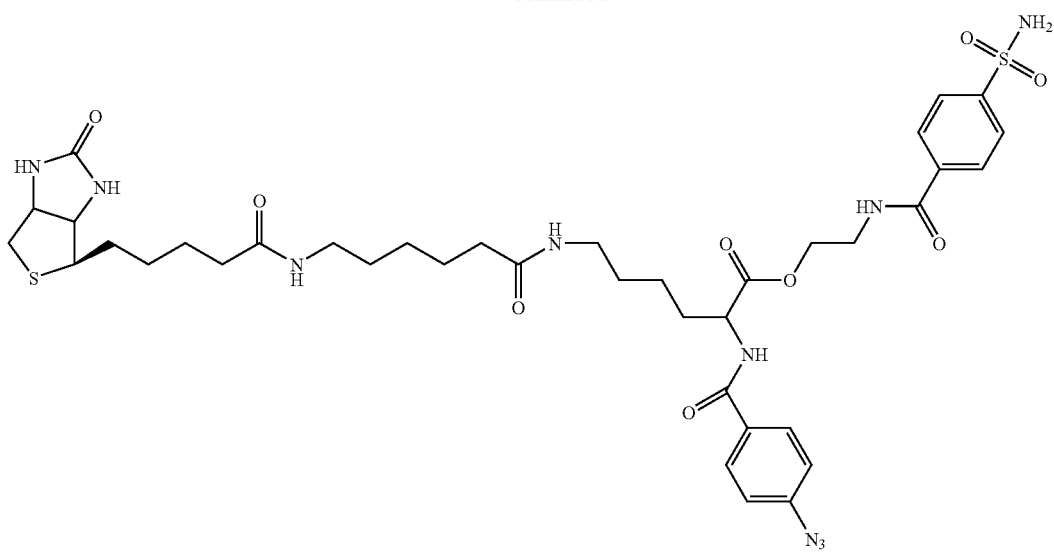
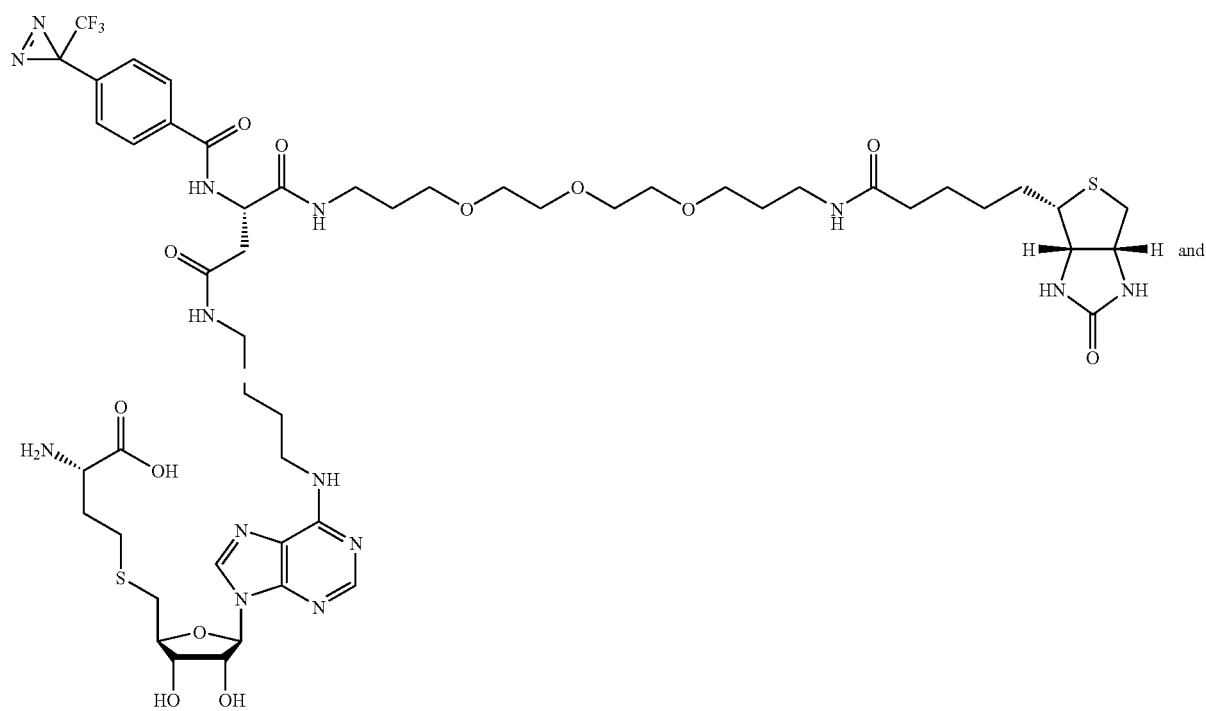
B2-N6-SAH
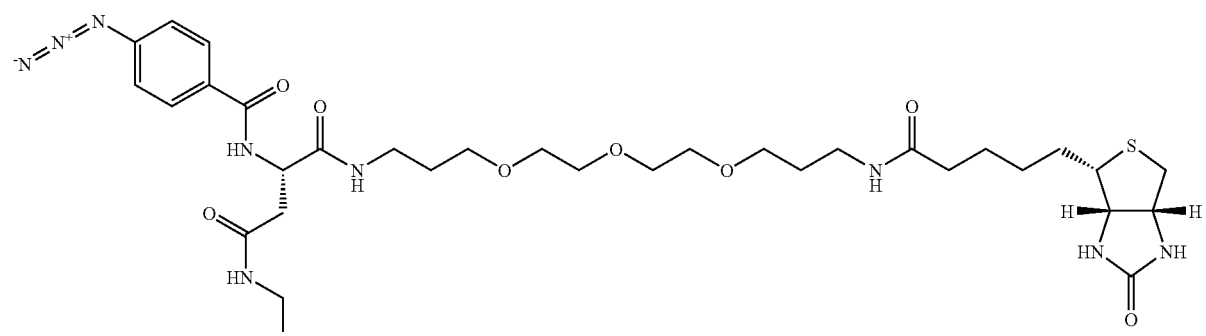

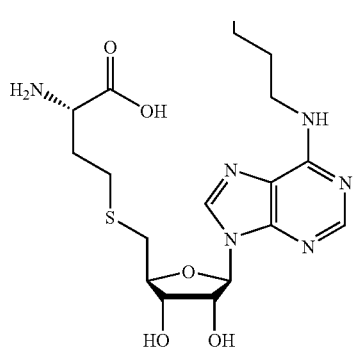

B1-N6-SAH

Specific compounds within these embodiments are those resulting from all combinations of the groups listed above for the variables contained in this formula and all can include Q groups. It is intended herein that each of these specific compounds is within the scope of the disclosure herein.

F. Methods

The magnetic separator devices provided herein can be used to separate any magnetic particle from a reaction mixture, solution or sample for analysis. They can be used for example in embodiments of methods practiced on solid supports and with capture compounds described, for example published International PCT application Nos. WO 03/092581 and WO 04/06497. Samples for analysis include any sample that potentially contains a molecule of such interest, including, but are not limited to, macromolecules, biological particles and biomolecules, particularly protein-containing samples, such as protein mixtures, including, but not limited to, natural and synthetic sources, such as cell lysates or compositions containing proteins. Proteins can be prepared by translation from isolated chromosomes, genes, cDNA and genomic libraries. Proteins can be isolated from cells, and other sources. In certain embodiments, the capture compounds that are designed to selectively capture different post-translational modifications of the same protein (i.e., phosphorylation patterns (e.g., oncogenes), glycosylation and other post-translational modifications) are used.

The methods include any for the discovery and identification of one or more molecules in a sample or for assessing interactions of molecules. The methods described in applications International PCT application Nos. WO 03/092581 and WO 04/06497 allow biomolecules, such as proteins, to bind under physiological conditions while maintaining the correct secondary and tertiary conformation. The methods can be performed under physiological and other conditions that permit discovery of biologically important proteins, including membrane proteins, that are selected based upon a defined phenotype.

In the methods provided herein, the capture compounds are provided on or linked during reaction to magnetic particles or beads, and thus include a moiety or functionality that allows immobilization of the capture compound to a magnetic particle/bead.

In methods provided herein, capture compounds can be attached to a solid support, such as a magnetic bead, before, during or after contacting with a molecule of interest, such as a biomolecule, such as a protein. In one example, the caprotec Capture Compound™ compounds can be attached to a magnetic bead through the sorting function of the capture compound. The sorting function, for example, can be an oligonucleotide, or analog thereof, and the magnetic beads/particles present complementary oligonucleotides or analogs thereof. The compounds are allowed to hybridize to a complementary strand of immobilized oligonucleotide(s), or analog(s) thereof, before, during or after contacting with molecules, such as biomolecules, to effect immobilization on the magnetic particle/bead for separation using the devices provided herein.

In the methods provided herein, molecules of interest, such as biomolecules, can be analyzed or identified by any method known to one of skill in the art, such as, for example, electrophoretic mobility, e.g., PAGE and SDS-PAGE, HPLC, chromatography, NMR, and mass spectrometry, such as matrix assisted laser desorption ionization-time of flight (MALDI-TOF) and Electrospray Ionization (ESI) mass spectrometry and Surface Plasmon Resonance (SPR). Capture compounds or other molecules to be immobilized on the magnetic particles/beads can include colorimetric, fluorescent and chemiluminescent tags or mass modifying tags to allow for increased resolution during analysis, such as by mass spectrometry, including MALDI-TOF and ESI mass spectrometry.

1. Capture Methods—Kinetic Conditions

The methods and magnetic separation devices provide herein can be used for probing a sample and detecting and/or isolating target molecules in s solution, sample or reaction mixture. In these methods, the capture compounds includes a reactivity function X for covalently capturing target molecules. In practice these methods are performed under kinetically controlled conditions. For a reaction to be "kinetically controlled" means that it is time dependent—the amount of reactants and products changes over time. This occurs until a reaction reaches equilibrium. To perform a reaction that is kinetically controlled means to perform it under non-equilibrium conditions, such that the amount of product is a function of time of reaction. In the instant case, to perform a reaction under conditions such that the interactions are kinetically controlled means that the reaction is performed such that the interactions of the reactivity X and the selectivity moiety Y are a function of time of the reaction Exemplary capture methods use capture compounds or collections thereof that include a core function Z that presents at least a reactivity function X and a selectivity function Y. The reactivity function X is selected to interact with the target molecule(s) and the selectivity function Y modifies the interaction of the reactivity function X with molecules in the sample. In these methods, the reactivity function X can be almost any molecule or moiety that covalently binds to the molecule of interest. For methods of detecting or isolating molecules from a mixture or sample, the selectivity function Y is a moiety selected to modulate interactions of the reactivity function X and allows studying molecules in a sample, such as biomolecules in a sample, by capturing biomolecules via their interaction with reactivity function X as modulated by selectivity function Y. The selectivity function Y modifies the interaction of the reactivity function X with molecules in the sample, and is used to functionally reduce the complexity of a biological sample. In some embodiments, the collections of capture compounds include a selectivity function Y selected to modulate interactions of the reactivity function X. Provided are methods for studying biomolecules in a samples by capturing biomolecules via their interaction with X as modulated by Y.

In the capture methods, the capture compounds detect or isolate target molecules in the sample or mixture. In these capture methods, the capture compounds include a reactivity function X for covalently capturing target molecules. The capture compounds optionally include a selectivity function Y moiety, which modulates that interaction of the reactivity function X moiety with the target molecules. The capture compounds also include a sorting function Q for immobilizing the capture compounds on a solid support. In some embodiments, the sorting function Q is one member of a specific binding pair, and the corresponding member of the binding pair is attached to the surface of a solid support, such as a magnetic particle, such as a magnetic bead. Exemplary specific binding pairs include ligand-receptor binding pairs; hormones and hormone receptors, e.g., epidermal growth factor and epidermal growth factor receptor, tumor necrosis factor and tumor necrosis factor-receptor, and interferon and interferon receptor; a chemokine and chemokine receptor, a growth factor and growth factor receptor, avidin and biotin; NeutrAvidin and biotin; CaptAvidin and biotin; biotin and streptavidin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; β-glucan and a β-glucan-binding protein; specific carbohydrate and lectin binding pair; endotoxin and an endotoxin-neutralizing protein; and stimulating factors and there receptors, such as granulocyte-macrophage colony stimulating factor (GMCSF) and GMCSF receptor and macrophage colony stimulating factor (MCSF) and MCSF receptor. In some embodiments, the sorting function Q is one member of a bind pair selected from among avidin and biotin; NeutrAvidin and biotin; CaptAvidin and biotin; biotin and streptavidin; and antibody and antigen pairs. In some embodiments, the sorting function Q is biotin and the magnetic beads include streptavidin. In some embodiments, the sorting function Q is streptavidin and the magnetic beads include biotin.

In some embodiments, the methods use collections of capture compounds, and can be used to probe the proteome. The collection of capture compounds can include compounds with the same sorting function Q and different reactivity functions X, or the same sorting function Q and reactivity function X and different selectivity functions Y, and other variations thereof. In some embodiments, each compound in the collection can have a different sorting functions Q.

Also provided are methods for reducing diversity of a complex mixture of molecules, which include contacting the mixture with a collection of capture compounds attached to a magnetic particle to form capture compounds with bound molecules; and after contacting, separating capture compounds with bound molecules from the mixture. In some embodiments, the magnetic particles with the attached capture compounds with bound molecules can be separated from the mixture using the magnetic device described herein.

Also provided are methods for identification of phenotype-specific molecules, the method including the steps of sorting cells from a single subject according to a predetermined phenotype to produce at least two separated sets of cells; contacting mixtures of biomolecules from each set of sorted cells with a collection of capture compounds attached to magnetic particles to form capture compounds with bound biomolecules captured on magnetic beads; separating the magnetic beads from the mixture; and comparing the binding patterns of biomolecules from each set bound to capture compounds to identify biomolecules that differ for each set, thereby identifying phenotype-specific biomolecules. In some embodiments, the magnetic particles with the attached capture compounds with bound molecules can be separated from the mixture using the magnetic device described herein. In some embodiments, the cells are synchronized or frozen in a metabolic state before sorting and/or after sorting. In some embodiments, the biomolecules include proteins. In some embodiments, the bound biomolecules are identified by electrophoretic mobility or mass spectrometry or surface plasmon resonance. In some embodiments, the phenotypes are diseased and healthy phenotypes. In some embodiments, the diseased phenotype is a tumor and the healthy phenotype is non-tumor.

2. Assessing the Interaction with a Molecule—Equilibrium Conditions

The methods and magnetic separation devices provide herein can be used for probing a sample and assessing the interactions of a molecule, such as a biomolecule, in a solution, reaction mixture or sample. In some embodiments, the methods are for assessing the interactions of groups, such as drugs, drug fragments, drug metabolites and/or drug intermediates with molecules in a sample. The group interacts with molecules in a sample and the interaction is allowed to proceed until it reaches equilibrium. In these methods, capture compounds are selected to include an activatable reactivity function X that forms a covalent bond, such as by activation with the biomolecule with which Y interacts. This permits assessment of the molecules with which selectivity function Y interacts. The activatable reactivity function X does not form a covalent bond with the target molecule until activated, such as by exposure to irradiation or to a change in pH.

This method can be used, for example, to identify so-called non-drug targets and to assess affinities of a drug with its target and non-targets. As is known in the art, a particular drug is designed to target a molecule, such as a receptor or enzyme. Interaction of a drug or its metabolites or fragments with other molecules besides the target can lead to side effects. The method permits identification of molecules, such as biomolecules, with which such drugs, metabolites or fragments interact, thereby permitting redesign of drugs to reduce or alter such interactions, which can reduce or eliminate unwanted side effects due to interaction with non-target molecules.

For example, if selectivity function Y is a drug, then contacting it with a sample from a biological fluid or cell sample can be used to identify and/or assess with what other non-target molecules(s), in addition to the drug target, the drug interacts. The non-target molecules can be responsible, for example, for undesirable side-effects. When non-target molecules are identified and their interaction with the drug or drug metabolite is characterized and/or analyzed, the drug can be redesigned to eliminate or reduce interactions with non-target molecules, and thereby reduce undesirable side-effects. In these methods, the sample is permitted to interact under equilibrium conditions with capture compounds that include the selectivity function Y. In these methods, the selectivity function Y is the molecule that is under study, such as a pharmaceutical drug, drug fragment, drug intermediate, drug metabolite, prodrug, enzyme substrate or inhibitor, a co-factor, a receptor ligand, a transition state analog or a peptide. The capture compounds present the pharmaceutical drug, drug fragment, drug intermediate, drug metabolite, prodrug, enzyme substrate or inhibitor, a co-factor, a receptor ligand, a transition state analog, or a peptide or nucleic acid or oligonucleotide to the molecules present in the reaction mixture or sample, such as a biological sample. A period of time for presentation of the pharmaceutical drug, drug fragment, drug intermediate, drug metabolite, prodrug, enzyme substrate or inhibitor, a co-factor, a receptor ligand, a transition state analog, or a peptide, or nucleic acid or oligonucleotide to the molecules in the reaction mixture or sample is allowed for the pharmaceutical drug, drug fragment, drug intermediate, drug metabolite, prodrug, enzyme substrate or inhibitor, a co-factor, a receptor ligand, a transition state analog, or a peptide or a nucleic acid or oligonucleotide presented by the capture compound and molecules, e.g., biomolecules in the sample to reach equilibrium. Once equilibrium is reached, or after a sufficient presentation time, the activatable reactivity function X on the capture compound is activated, such as by exposure to irradiation or a change in pH, resulting in the formation of a covalent bond between the reactivity function X on the capture compound and any molecules with which the pharmaceutical drug, drug fragment, drug intermediate, drug metabolite, prodrug, enzyme substrate or inhibitor, a co-factor, a receptor ligand, a transition state analog, or a peptide or nucleic acid or oligonucleotide interacts, such as target molecules and possibly other non-target molecules in the reaction mixture or sample. The captured target and any non-target molecules then are identified. The captured non-target molecules, for example, in the case where the selectivity function Y is drug, drug fragment or metabolite, can be responsible or related to side effects of the drug.

The method can include as an optional step identifying a function of the captured molecule, such as a target or non-target molecule. In some embodiments, a function of a molecule, such as a biomolecule, is determined by sequence alignment, pharmacophores, homology models and protein motif correlation, liver microsome assays and metabolic pathway analysis, cDNA-expressed enzymes, signal pathways and back-mapping to other pathways, such as yeast pathways, simulations and protein/protein interaction, native polymorphisms, knock-out/knock-in approaches, flow cytometry, therapeutic activity of the molecule, prospective genotyping and prospective phenotyping. In some embodiments, the method includes digesting captured molecules, such as biomolecules, by chemical or enzymatic treatment prior to the analysis step.

In some embodiments, the activatable reactivity function X is photoactivatable. In some embodiments, the method includes activating the photoactivatable reactivity function moiety by exposure to the appropriate wavelength of light, whereby the reactivity function moiety then reacts with a surface group of a target and/or non-target molecule to capture it. In one embodiment, the photoactivatable group is selected from among an arylazide, such as a phenylazide, a diazirine group, such as 3-trifluoromethyl-diazirine or a benzophenone moiety. In some embodiments, the reactivity function X is a latent group requiring activation prior to its formation of a covalent bond with a target or non-target molecule, and is selected from among 1,3-dioxoisoindolin-2-yl acetate, 1-acetyl-1H-pyrrole-2,5-dione, oxiran-2-yl acetate, (2-oxo-1,3-dioxolan-4-yl)methyl acetate, 4-methyl-1,3-dioxolan-2-one, acetic pivalic anhydride and N-(3-aminopropyl)acetamide.

Accordingly, provided herein are methods of drug screening, which include exposing a capture compound that includes a selectivity function Y that is a pharmaceutical drug, drug fragment, drug intermediate, drug metabolite, prodrug, enzyme substrate or inhibitor, a co-factor, a receptor ligand, a transition state analog, or a peptide or nucleic acid or oligonucleotide and a activatable reactivity function X and a sorting function Q to a mixture of target and/or non-target molecules in a sample; allowing the capture compound and molecules, e.g., biomolecules in the sample, to reach equilibrium; and activating the reactivity function to capture the molecules that interact with the selectivity function (e.g., pharmaceutical drug, drug fragment, drug intermediate, drug metabolite, prodrug, enzyme substrate or inhibitor, a co-factor, a receptor ligand, a transition state analog, or a peptide or nucleic acid or oligonucleotides). Any non-target molecules that interact with the pharmaceutical drug, drug fragment, drug intermediate, drug metabolite, prodrug, enzyme substrate or inhibitor, a co-factor, a receptor ligand, a transition state analog, or a peptide or nucleic acid or oligonucleotide can be identified.

3. Functional Isolation of Target Proteins Using Capture Compounds

Capture compounds are used to isolate biomolecules, such as proteins of interest, from a complex biological sample. Any capture compound that includes a functionality that selectively interacts or binds with the biomolecule, such as a protein of interest, with high affinity resulting in a complex that can be recovered from the biological sample can be used. In some embodiments, the capture compounds include a sorting function, a reactivity function and a variable selectivity function and optionally a solubility function are used to selectively interact with and bind to proteins of interest in a complex biological sample, thereby allowing isolation of the biomolecule, such as a protein of interest, from the complex biological sample. A reactivity function on the capture compounds allows for a covalent attachment of the capture compound to the biomolecule. For example, the reactivity function can be selected such that upon exposure to UV light, the reactivity function is activated and forms a covalent attachment to the biomolecule. Exemplary capture compounds are available from caprotec bioanalytics GmbH, Berlin, Germany.

The sample that contains the molecule(s) of interest, such as biomolecules, e.g., proteins, can be any sample obtained from any source, such as an environmental sample, including water samples, food samples, and biological samples, including suspensions, extracts, or leachates of environmental or biological samples. In some embodiments, the sample is a biological sample, such as a sample obtained from a living or viral source or other source of macromolecules and biomolecules. Biological samples can include any cell type or tissue of a subject from which a biomolecule, such as a nucleic acid molecule or protein or other macromolecule can be obtained. Exemplary biological samples include blood, a bone marrow sample, an effusion of any type, ascites fluid, pleural fluid, spinal fluid, lymph, serum, plasma, sweat, mucus, sputum, saliva, urine, semen, sperm, ova, amniotic fluid, stool, mouth wash, tears, ocular fluid, extracts of nasal, throat or genital swabs, cell suspension from digested tissue and extracts of fecal material. Biological samples can also be samples of organs or tissues, including tumors, such as fine needle aspirates, cell pellets, biopsies, biological tissues and lysates thereof or samples from perfusions of organs or tissues. Biological samples also can be samples of cell cultures, including both primary cultures and cell lines. The volume of a sample can be very small, such as in the nanoliter to microliter range, and may require dilution, or a sample can be very large, such as up to about two liters for ascites fluid. In some embodiments, the molecule of interest is a biomolecule.

The capture compounds are incubated with the sample and selectively interact with one or more molecules, such as biomolecules, including a protein of interest. A reversible affinity driven interaction between the selectivity function of the capture compounds and the molecules, such as target proteins, occurs.

In a subsequent step, the sample including the molecule, such as a biomolecule, e.g., the target protein, and the capture compounds are subjected to conditions, such as exposure to UV light or other activating conditions, that activate the reactivity function. Irradiation of the sample with UV light can be performed at any suitable temperature including room temperature and below, such as at 0-4° C.

The capture compounds include a sorting function to isolate captured biomolecules, such as target proteins, from the biological sample. In some embodiments, the capture compounds include one member of a specific binding pair. Any specific binding pair can be selected. Exemplary binding pairs include biotin-streptavidin, biotin-avidin, a chemokine-chemokine receptor, a growth factor-growth factor receptor, an antigen-antibody, a specific sugar and the corresponding physiologically active substance such as lectin, β-glucan and a β-glucan-binding protein, and endotoxin and an endotoxin-neutralizing protein. In some embodiments, the capture compounds includes biotin as a sorting function. In some embodiments, the capture compounds includes avidin or streptavidin as a sorting function or fluorescein as sorting function interacting with anti-fluorescein antibodies attached to a solid support such as magnetic particles.

Magnetic particles, such as beads, which include on their surface the corresponding member of the binding pair used as the sorting function on the capture compounds can be used for isolation of the captured proteins. For example, in embodiments where the capture compounds include biotin as the sorting function, avidin- or streptavidin-coated magnetic beads can be used to isolate the captured biomolecules, such as target proteins, from the reaction mixture. In embodiments where the capture compounds include avidin as the sorting function, biotin-coated magnetic beads are used to isolate the captured biomolecules, such as target proteins, from the reaction mixture. The isolated biomolecules can be analyzed and directly identified, such as by electrophoretic analysis or by mass spectrometry or surface plasmon resonance.

Magnetic particles modified to include on their surface one member of a specific binding pair are known in the art and/or are commercially available (e.g., Dynal, Inc. Great Neck, N.Y. and Oslo Norway; Bioclone, Inc, San Diego, Calif.). These include avidin coated magnetic beads, streptavidin coated magnetic beads, oligosaccharide coated magnetic beads (Rye et al., Glycobiology 7(2): 179-182 (1997)), antibody coated magnetic beads and antigen coated magnetic beads.

An advantage of using the capture compounds that include a sorting function, a reactivity function and a variable selectivity function and optionally a solubility function as described above is that the target protein capture reactions are performed in a simple "one-pot" reaction protocol that is amenable to automation and scale-up using readily available liquid handling and robotic devices.

4. Separation of Magnetic Particles with Biomolecules from a Reaction Solution

The magnetic separator device described herein is used to separate magnetic particles from a reaction system. For example, a vessel including a solution in which magnetic particles having biomolecules of interest attached thereto are suspended is placed in a holding rack and the lid(s) of the vessel is/are removed.

The magnetizable plate of the device is placed over the vessel. The lid(s) of the vessel is/are then placed in the magnetizable plate of the device, such that the magnetic plate is in-between the lid(s) of the vessel and the vessel. An exemplary depiction of this is shown in FIG. 1. Subsequently, the reaction vials are sealed by engaging the lid(s) with the vessel (either each vial or each well of the multi-well plate individually). The sheath of the separator device containing the magnet is placed over the lids and the magnetic plate, and the fit pins of the sheath are aligned with the fit pin holes of the magnetizable plate, aligning the sheath with the magnetizable plate. The magnet in the sheath attracts the magnetizable plate. The magnetic separator device then is rotated by 180° so that magnet of the device is on the bottom and the inverted vessel(s) is/are on top, the suspension(s) has/have moved down and is/are now in direct contact with the lid(s) and the magnetic particles are collected onto the lid(s) by the magnetic field. The device is allowed to remain in this position for a period of time, such as 10, 15, 20, 30, 40, 50, 60, 70, 80, 90, 100, 110, 120, 130, 140, 150, 160, 170, 180, 190, 200, 210, 220, 230, 240, 250, 260, 270, 280, 290 or 300 seconds to collect all of the magnetic particles in the vessel onto the lid(s). The device is inverted back to its original position by turning 180°, resulting in the sheath containing the magnet to be on top and the vessel(s) to be on the bottom. With the magnetic particles held in the lid(s) by the magnetic separator device, the reaction solution moved back to the bottom of the vessel(s) is free from magnetic particles carrying the biomolecules of interest. The vessel(s) is/are placed back again into the rack. The magnetizable plate is held towards the sheath of the separator device and removed from the vessel(s) thereby removing the lid(s) from the vessel(s). The magnetic particles carrying the biomolecules of interest are retained in the middle of the lid(s), which are held by the magnetizable plate, which is attracted towards the sheath of the device by the magnet. The reaction solution, now free of magnetic particles, remains in the bottom of the vessel. The vessel with the reaction solution is discarded. A new vessel filled with a wash solution is placed in the rack. The magnetic separator device, which has the lids with the magnetic particles attached, is repositioned on the vessel(s) and the separator device is pushed towards the vessel, pushing the lid(s) in the magnetizable sheet onto the vessel(s), sealing each opening of the vessel(s). The sheath of the device containing the magnet is removed, and the magnetic particles that were retained on the lid(s) can be released from the lid by shaking because there is no magnetic field, resulting in the magnetic particles being resuspended in the wash solution within the new vessel. The old lid(s) is/are removed from the magnetizable plate of the separator device and discarded, and new lid(s) is/are used to seal the new vessel(s) with the magnetizable plate of the device now being positioned between the new lid(s) and the new vessel(s).

After the magnetic particles have been washed in the wash solution by incubating for a certain time, they can be collected from the wash solution using the separator device as described for the suspension of the magnetic particles in the initial reaction solution, i.e. by repeating the steps of placing the sheath of the separator device containing the magnet over the lids and the magnetic plate and aligning the fit pins of the sheath with the fit pin holes in the magnetizable sheet; rotating the magnetic separator device by 180° so that magnet of the device is on the bottom and the inverted vessels is on top; allowing the device to remain in this position for a period of time from 10 seconds to 5 minutes to collect all of the magnetic particles in the vessel onto the lid(s); inverting the device back to its original position by turning 180° so that the magnet of the device is on top and the vessel(s) is/are on the bottom; holding the magnetizable plate of the device towards the sheath of the device and removing the device to remove the lid(s)s including the magnetic particles from the vessel; discarding the vessel with the wash solution; replacing the vessel(s) with new vessel(s) with a different washing solution; placing the device onto the new vessel(s) with a different wash solution, thereby engaging the lid(s) with the vessel(s), sealing each opening of the vials or well of the multi-well plate; and removing the sheath of the device containing the magnet from the magnetizable sheet, thereby releasing the magnetic particles into the new vessel with the new wash solution. The wash procedure can be repeated several times to wash the magnetic particles free from any contaminants originating from the reaction mixture. In the final step, new vessel(s) containing the desired processing solution is selected, and the device is placed over the new vessel(s), the lids retained in the separator device are engaged with the new vessel(s), and the sheath with the magnet of the device is removed, releasing the magnetic particles into the new vessel containing the desired solution for further processing.

G. Systems

The magnetic separation device described herein can be used in combination with capture compounds, including trifunctional capture compounds, for manipulation of molecules, including biomolecules. In some embodiments, provided is a system that includes a magnetic separator device as described herein and one or more capture compounds, such as capture compounds that contain one member of a specific binding pair as a sorting function and magnetic particles having attached to their surface the corresponding member of the specific binding pair. In some embodiments, provided is a system that includes a magnetic separator device as described herein and one or more capture compounds, such as trifunctional capture compounds attached to magnetic particles. Exemplary of such capture compounds attached to magnetic particles is caprotec's Capture Compound™ compounds attached to magnetic beads, such as caproBeads™ magnetic beads, which are streptavidin-coated magnetic beads with capture compounds that include biotin, which interacts with the streptavidin.

Also provided are systems that include the magnetic separation device provided herein, and capture compounds linked to magnetic beads and a source of UV light. The UV light is for activating the photoreactive moiety of the capture compounds, so that the compounds react with other molecules, such as biomolecules, including protein, nucleic acids and carbohydrates. The UV light source can include a box or housing that includes a UV lamp. The UV light source also can include a timer that controls the duration of illumination of the UV lamp. The UV light source also can include a cooling device that can modulate the temperature within the box housing the UV light source. The UV light source also can include a thermometer or thermoresistor or other device that automatically monitors or senses the temperature within the box housing the UV light source. In some embodiments, the UV light source includes a temperature control system that monitors the temperature within the box housing the UV light source and automatically controls the temperature within the box to a preset or predetermined temperature. In some embodiments, the temperature controller of the light source is programmable to maintain one or a plurality of temperatures for a given time for a predetermined duration of time. In one embodiment, the system includes a magnetic separator device provided herein and a UV light source configured to accept and contain the magnetic separator device. In some embodiments, the UV light source includes a timer that controls the duration of illumination of the UV lamp and a cooling device that modulates the temperature within the box housing the UV light source and containing the separation device. Included in the system housing the UV light source is a microtitre plate holder connected to a cooling device (Peltier element), which keeps the temperature in the biological sample during heat generating photoactivation at a low and controlled temperature to prevent denaturation of biomolecules such as proteins during crosslinking.

To increase the throughput of complex reaction protocols, including multiple washing protocols and reaction protocols, the magnetic separation device provided herein can be used in conjunction with currently available robotic systems (e.g., the BioRobot 9600 from Qiagen, the Zymate from Zymark or the Biomek from Beckman Instruments), most of which use the multi-well microtiter plate format. Incorporation of commercially available fluid handling instrumentation can significantly reduces the time frame of manual washing procedures and permits efficient analysis of many compounds, including biomolecules of interest.

In addition, high throughput screening systems are commercially available (see, e.g., Zymark Corp., Hopkinton, Mass; Air Technical Industries, Mentor, Ohio; Beckman Instruments, Inc. Fullerton, Calif.; Precision Systems, Inc., Natick, Mass., etc.). These systems typically automate entire procedures, including all sample and reagent pipetting, liquid dispensing and timed incubations. These configurable systems provide high throughput and rapid start up as well as a high degree of flexibility and customization. The manufacturers of such systems provide detailed protocols for various high throughput systems. The high throughput methods also can contain software to facilitate the high throughput reading and storage of data in the form of images and measurements, such as the relative expression levels of a fluorescent, luminescent or colored protein or product from the reaction. These high throughout screen systems can be configured to receive the vessels from the magnetic separator device, or to automate the performance of the steps outlined above for separation of magnetic particles including target proteins from reaction mixtures. These commercial systems could also be upgraded by the magnetic separation device provided herein.

High throughput assays for the presence, absence, or quantification of particular nucleic acids or protein products are well known to those of skill in the art. Similarly, binding assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

The magnetic separation devices provided herein also can be used in conjunction with or integrated with automated PCR systems, such as the GenXpert® system (Cepheid, Sunnyvale, Calif.), COBAS AMPLICOR PCR system (Roche Diagnostic Systems, see e.g., Jungkind et al., J Clinical Microbiology 34(11): 2778-2783 (1996)); and Agencourt® AMPure® PCR purification system (Agencourt Bioscience Corporation, Beverly, Mass.).

The magnetic separation devices provided herein also can be used in conjunction with or integrated with devices for performing chemical reactions on a solid support, such as described in U.S. Pat. No. 7,364,897. The magnetic separation devices provided herein also can be integrated with fully automated modular analytical systems that include integrated instrumentation for analysis of biopolymer samples, such as described in U.S. Pat. No. 6,730,517. The magnetic separation devices provided herein also can be integrated into an automated system that includes a mass spectrometry devices for analysis of nucleic acids and mutations or modifications thereof, such as described in U.S. Pat. Nos. 7,332,275, 7,198,893, 7,076,092, 7,074,563, 7,070,740, 7,019,288, 6,991,903, 6,764,822, 6,602,662, 6,558,902, 6,500,621, 6,436,635, 6,428,955, 6,300,076, 6,277,573, 6,268,144, 6,225,450, 6,258,538, 6,238,871, 6,235,478, 6,221,605, 6,221,601, 6,197,498, 6,194,144, 6,140,053, 6,043,031, 6,074,823, 5,691,141, and 5,547,835. The magnetic separation devices provided herein also can be used in conjunction with or integrated with automated diagnostic assays and diagnostic systems, such as those described in U.S. Pat. Nos. 7,482,143, 7,384,600, 7,118,892, 7,033,820, 6,890,742 and 6,605,213. The magnetic separation devices provided herein also can be used in conjunction with or integrated with cell based assays, clinical assays and/or diagnostic assays.

In some embodiments, the isolated biomolecules, such as target proteins, are analyzed, such as by mass spectrometry, including matrix assisted laser desorption ionization-time of flight (MALDI-TOF) or Electrospray Ionization (ESI) mass spectrometry, or Surface Plasmon Resonance (SPR) or by colorimetric, fluorescent or chemiluminescent tagging.

In certain embodiments, with its speed and precision ($M_r$ measured to 0.01%-0.10%), separating capabilities (even small structural variation can lead to mass shift) and ability to multiplex (many proteins scanned simultaneously), mass spectrometry is used for biomolecule analysis and identification, particularly protein analysis and identification. This initial mass spectrum provides the molecular weights of all biomolecules, such as proteins, captured. The identity of each then can be determined by conventional means (e.g., in the case of proteins, by digestion and analysis of peptide fragments and genome/proteome database searches). Use of the trifunctional capture compounds, such as the tri-functional caprotec Capture Compound™ compounds physically isolates captured molecules to permit further analysis thereof. Further analysis include, for example, mass spectrum identification and x-ray crystallography after removal from beads. To do so, the molecule, such as biomolecule, such as protein, is washed from the solid support, such as the magnetic beads (e.g., if using avidin/streptavidin beads, by treating the beads with biotin to displace captured proteins) or by making use of an incorporated photocleavable linker, or enzymatically or chemically cleavable linker, thereby releasing the captured biomolecule, such as protein, from the solid support).

Also provided are systems that include the magnetic separator device disclosed herein and a device for analysis of the isolated biomolecules, including proteins, nucleic acids and carbohydrates. In some embodiments, the device for analysis is selected from among a mass spectrometer, an electrophoretic separator device and a chromatography separator device or a Surface Plasmon Resonance device. In some embodiments, the analysis device is a device that performs gas-liquid chromatography, high performance liquid chromatography (alone or in combination with mass spectrometry), mass spectrometry, time of flight mass spectrometry with matrix-assisted laser desorption ionization (MALDI-TOF), quadrupole ion trap mass spectrometry, secondary ion mass spectrometry, accelerator mass spectrometry, inductively coupled plasma-mass spectrometry, Ion Mobility Spectrometry-MS, Surface Enhanced Laser Desorption Ionization (SELDI-TOF) and tandem mass spectrometry and Electrospray Ionization mass spectrometry.

In some embodiments, the systems include a mass spectrometer, a computer with appropriate software, capture compounds, such as capture compounds that include one member of a specific binding pair as a sorting function, magnetic particles having the corresponding member of the specific binding pair on their surfaces, and the magnetic separator device provide herein which can be used to capture and sort biomolecules for subsequent analysis by mass spectrometry. Such systems may be manual or automated as desired.

H. Combinations, Kits and Articles of Manufacture

The magnetic separator device and systems provided herein can be provided as a combination or packaged as kits. Kits can include the magnetic separator device or a system that includes a magnetic separator device and optionally can include one or more components such as instructions for use, additional reagents such as vessels, such as tubes, multi-well plates (e.g., microtiter plates) and containers for practice of the methods; capture compounds; substrates; and material components, such as magnetic beads, buffers and solvents. Those of skill in the art will recognize many other possible containers and plates that can be used for containing the various materials. The kit can also include reagents for performing the methods.

In one example, a kit includes a magnetic separator device as provided herein and instructions. Instructions typically include a tangible expression describing the device and, optionally, other components included in the kit, and methods for magnetic separation, including methods for preparing the magnetic beads and methods for preparing the capture compounds. In one example, a kit includes a magnetic separator device as provided herein, instructions and capture compounds. In one example, a kit includes a magnetic separator device as provided herein, instructions and a microtitre plate based device for providing ultraviolet light and sample cooling. An exemplary device for producing ultraviolet light is the CaproBox™ UV light and cooling device (Item. No. 1-5100-001, caprotec bioanalytics GmbH, Berlin, Germany), which is a specifically developed device for photo-cross-linking samples, where the device combines timed UV irradiation and temperature control in one system.

Also provided are articles of manufacture. The articles of manufacture provided herein contain the magnetic-separator device, optionally vessels, capture compounds, magnetic beads and packaging materials. Packaging materials for use in packaging products are known to those of skill in the art. See, e.g., U.S. Pat. Nos. 5,323,907, 5,052,558 and 5,033,252. Examples of packaging materials include, but are not limited to, blister packs, bottles, tubes, bags, vials, containers, and any packaging material suitable for a selected formulation and intended use. Articles of manufacture also can include a label with instructions for use of the packaged materials, including the magnetic separator provided herein.

One of skill in the art will appreciate the various components that can be included in a kit, consistent with the methods and systems disclosed herein.

I. Examples

The following examples are included for illustrative purposes only and are not intended to limit the scope of the embodiments provided herein.

Example 1

Exemplary Magnetic Separator Device

An example of the presently disclosed separation device is described below with reference to the attached drawings.

Referring to the drawings, FIG. 1 illustrates one embodiment of a magnetic separation device 10. Magnetic separation device 10 includes a plate 20, a sheath 30, a plurality of vials 50 and a plurality of vial lids 56, each lid associated with a specific vial. As will be described in more detail below, plate 20 is configured to receive vial lids 56 and configured to fit between sheath 30 and vials 50 such that the vial lids can engage with and seal vials 50 and the magnetic beads, inside vials 50 can be collected in lids 56 by orienting pins 34, made of iron, integrated in sheath 30, where the orienting pins 34 concentrate the magnetic field of a magnet embedded in sheath 30 while reaction mixtures in each vial 50 are removed.

Figure 2:
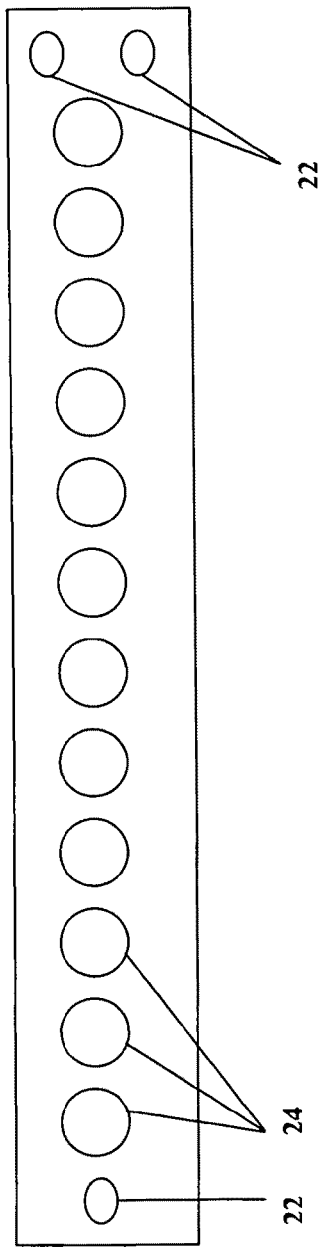
FIG. 2 is a top view of a plate embodiment of the device of FIG. 1.

Plate 20 is generally circular, square or rectangular, but can be configured in any geometry, such as shown in a rectangular geometry, and includes at least one fit pin hole 22 and a plurality of lid holes 24. Plate 20 is typically made of stainless steel magnifier 75 or any other magnetic material. Plate 20 is sized to accommodate by fitting over or covering the plurality of vials 50. As illustrated in the embodiment of FIG. 2, plate 20 has three fit pin holes 22. Fit pin holes 22 are sized to receive fit pins 32 on sheath 30 as will be described in detail below.

As also illustrated in the embodiment of FIG. 2, plate 20 has 12 vial lid holes 24. The number of vial lid holes 24 on plate 20 will generally equal the number of vials used during a testing procedure. For a vial rack (not shown) containing 12 vials, for example, plate 20 will include at least 12 vial lid holes. Plate 20, however, can include 1 lid hole, or any linear, circular or quadrangular array of lid holes that is a multiple of 2, 3, 4, 5, 6, 7, 8, 9, 10, 11, 12, 13, 14, 15, 16, 17, 18, 19, 20, 21, 22, 23, 24, 48 or 96. Therefore, plate 20 can include, for example, 1, 2, 3, 4, 5, 6, 7, 8, 9, 10, 11, 12, 13, 14, 15, 16, 17, 18, 19, 20, 21, 22, 23, 24, 48 or 96, 192, 384, 768, 864, 1152 or 1536 vial lid holes 24.

Figure 4:
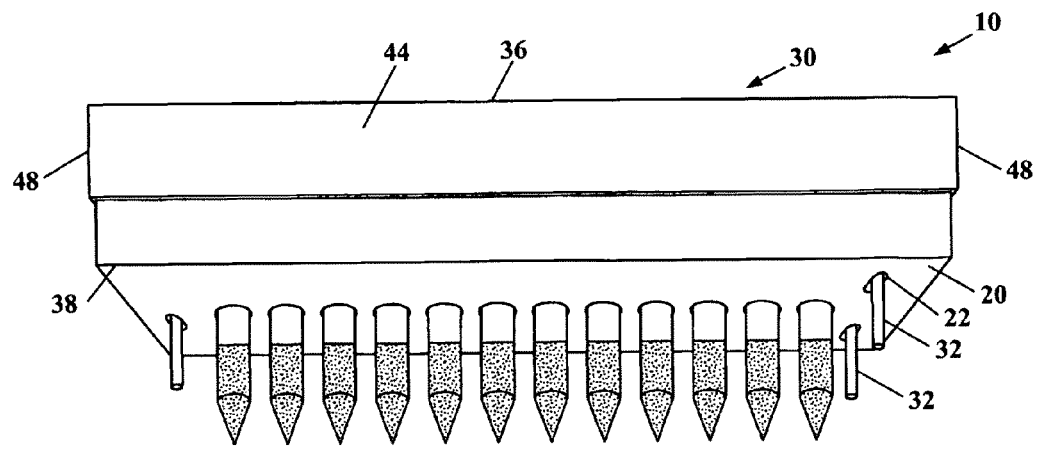
FIG. 4 is a perspective view of the magnetic separation device of FIG. 1.

Sheath 30 includes at least one fit pin 32 and a plurality of orienting pins 34, made of iron or other magnetic material, as shown in FIG. 3A. Sheath 30 is made of aluminum and includes a neodymium magnet 42 (not shown in FIG. 3A) embedded in sheath 30. In the embodiment illustrated in FIG. 3A, sheath 30 has three fit pins 32 to equal the three fit pin holes 22 on plate 20 shown in FIG. 2. Fit pins 32, made of iron or any other magnetic or non-magnetic material, are sized and configured to fit into fit pin holes 22 on plate 20. Fit pins 32 are generally embedded into sheath 30 to hold plate 20 in place during use. Sheath 30, as shown in FIGS. 3A, 3B and 4, also has a top face 36, bottom face 38, front wall 44, rear wall 46 and side walls 48. In some embodiments, sheath 30 only has bottom face 38 containing the fit pins 32 and the orienting pins 34.

Sheath 30 is designed to bring orienting pins 34 into close proximity to the magnet so that they can concentrate its magnetic field. In some embodiments, magnet 42 is embedded in sheath 30. In some embodiments, magnet 42 is attached/glued/screwed to sheath 30. The magnet can be embedded into or attached to the sheath during fabrication of the sheath, such as by crimping of the material from which the sheath is made onto the magnet or by direct casting, and/or the magnet can be held in place in the sheath, e.g., by magnetic interaction to the orienting pins 34, by glueing, by screwing, by threads, friction fit, snap fit, adhesive bonding, welding, mechanical clips, or by any other desired method.

As illustrated in FIG. 3A, sheath 30 has 12 orienting pins 34. Similar to the 12 vial lid holes 24 on plate 20, the number of orienting pins 34 on sheath 30 will generally equal the number of vials used during a testing procedure. For a vial rack (not shown) containing 12 vials, for example, sheath 30 will include at least 12 orienting pins 34. Sheath 30 can be configured to include only one orienting pin, or to include any linear or circular configuration or any quadrangular array that is a multiple of 2, 3, 4, 5, 6, 7, 8, 9, 10, 11, 12, 13, 14, 15, 16, 17, 18, 19, 20, 21, 22, 23, 24, 48 or 96. Therefore, sheath 30 can include, for example, 2, 3, 4, 5, 6, 7, 8, 9, 10, 11, 12, 13, 14, 15, 16, 17, 18, 19, 20, 21, 22, 23, 24, 36, 48, 96, 384, 768, 864, 1152 or 1536 orienting pins 34. The orienting pins are made from iron, any other magnetic material or can also be magnets by themselves and are integrated into sheath 30. The orienting pins 34 concentrate the magnetic field created by the rare-earth magnet.

In some embodiments, as illustrated in side-view FIG. 3B, sheath 30 has a U-shaped design. As shown in FIG. 3B, sheath 30 has three fit pins 32 to equal the three fit pin holes 22 on plate 20 shown in FIG. 2. The sheath 30 has a bottom face 38, front wall 44, rear wall 46 and side walls 48. Sheath 30 also optionally has a cavity 40 formed between the top face, bottom face, front wall, rear wall and side walls. Cavity 40 is sized to receive one or more than one magnet 42, which can be fitted snugly into cavity 40. The magnet can be retained in the cavity of the sheath by any desired method, such as by magnetic interaction to the orienting pins 34, by glueing, by screwing, by crimping of the material from which the sheath is made onto the magnet, or by threads, friction fit, snap fit, adhesive bonding, welding or mechanical clips. Sheath 30 optionally also can include a removable top 36 that allows sheath 30 to encase totally magnet 42. Removable top 36 allows the insertion and removal of magnet 42 as necessary. Sheath 30 optionally only has bottom face 38 containing the fit pins 32 and the orienting pins 34 and the magnet 42 can be attached to the sheath by glueing, screwing, magnetic interaction to the orienting pins 34 or by any desired method. As stated above, each vial 50 on the rack (not shown) is provided with an associated lid 56. Lids 56 can be provided on a lid strip 58 shown in FIG. 1 to simplify and reduce the time for the removal of multiple lids 56. Each vial 50 houses a reaction mixture 52 and at least one magnetic particle 54 in the reaction mixture. Magnetic particles 54 optionally can include a streptavidin or antibody coating. Reaction mixture 52 generally includes a biological sample containing specific proteins that can be isolated from the biological sample by binding to the at least one magnetic particle 54 within vial 50. Reaction mixture 52 can optionally includes capture compounds, which are used to functionally reduce the complexity of a biological sample. The proteins are captured on the beads, such as by the capture compounds, which optionally are tagged, and the proteins or the complex of proteins/capture compounds bind to the surface of magnetic beads 54, which are isolated and purified from reaction mixture 52 by using magnetic separation device 10 as described below.

To remove magnetic beads 54 from reaction mixture 52 within vials 50 after the beads have bound the desired biomolecules, such as proteins, optionally by using capture compounds, the open(ed) vials 50 containing reaction mixture 52 and suspended magnetic beads 45 are placed in a rack (not shown). Plate 20 is placed between vials 50 and lid strip 58 as shown in FIG. 1, after which lid strip 58 is placed on vials 50 to close the vials and retain plate 20 between the vials and the lid strip.

With plate 20 in place, sheath 30 containing a magnet is placed over lid strip 58 such that fit pins 32 of sheath 30 pass through fit pin holes 22 of plate 20. This holds sheath 30 in place and positions properly each orienting pin 34 over the center of its respective vial lid 56. The steel plate 20 is further held in place by magnetic attraction to the neodymium magnet in sheath 30. The fully connected device 10 is illustrated in FIG. 4 with each component more clearly shown in exploded FIG. 1.

Figure 5:
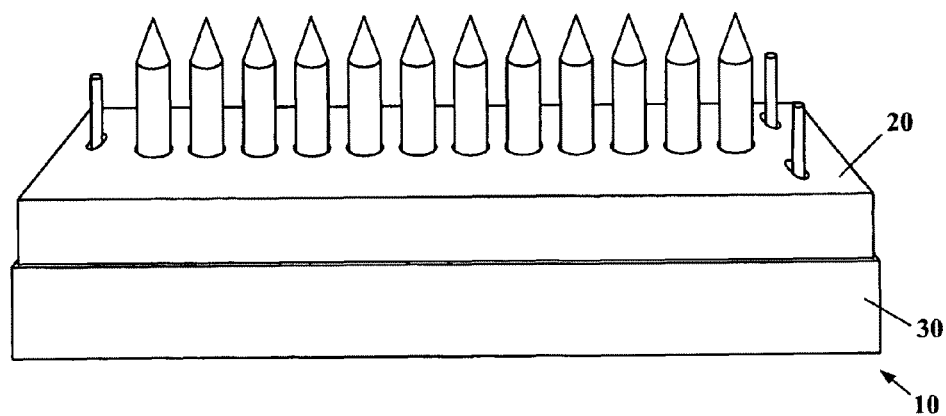
FIG. 5 is a perspective view of the magnetic separation device of FIG. 4 rotated 180° having concentrated the magnetic beads at the lids of the reaction vessels.

Mostly, vials 50 are not entirely filled with reaction mixture 52 containing suspended magnetic beads 45 so that there is air between the meniscus of reaction mixture 52 and lids 56 hindering magnetic beads 45 to be collected in lids 56 by the orienting pins 34, which concentrate the magnetic field of magnet 42. To draw magnetic beads 54 towards vial lids 56, the magnetic separation device 10 is rotated 180° such that the vials are oriented upside down relative to the initial position of FIG. 4. In this rotated configuration, shown in FIG. 5, the reaction mixture 52 has flowed down towards the lid 56 and is now in direct contact with the lid 56. The neodymium magnet of sheath 30, mediated by orienting pins 34, draws magnetic beads 54 to vial lids 56. Moreover, each orienting pin 34 of sheath 30 is fixed over the center of each respective vial lid 56. As a result, the magnetic field generated by the neodymium magnet concentrates at each pin 34, allowing for collection of magnetic beads 54 from each vial 50 at the center of each respective vial lid 56.

Figure 6:
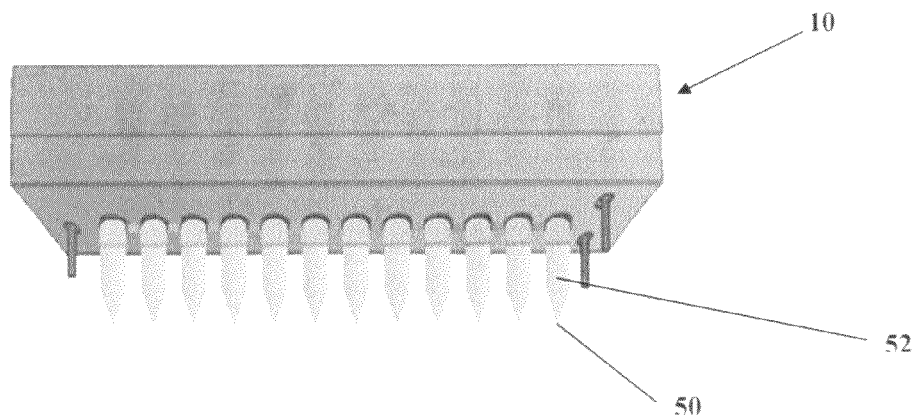
FIG. 6 is a perspective view of the magnetic separation device of FIG. 4 after magnetic bead separation.

After a sufficient incubation period to allow collection of all magnetic beads 54 on lids 56 (e.g., two minutes), device 10 is rotated back 180° to its initial position. Even when rotated, device 10 maintains a tight fit between plate 20, lid strip 58 and sheath 30 due to the magnetic attraction between the magnet-embedded sheath 30 and steel plate 20. Reaction mixture 52 flows to the bottom and returns to its initial position in vials 50, free from magnetic beads 54, as shown in FIG. 6, which remain collected on lids 56.

Figure 7:
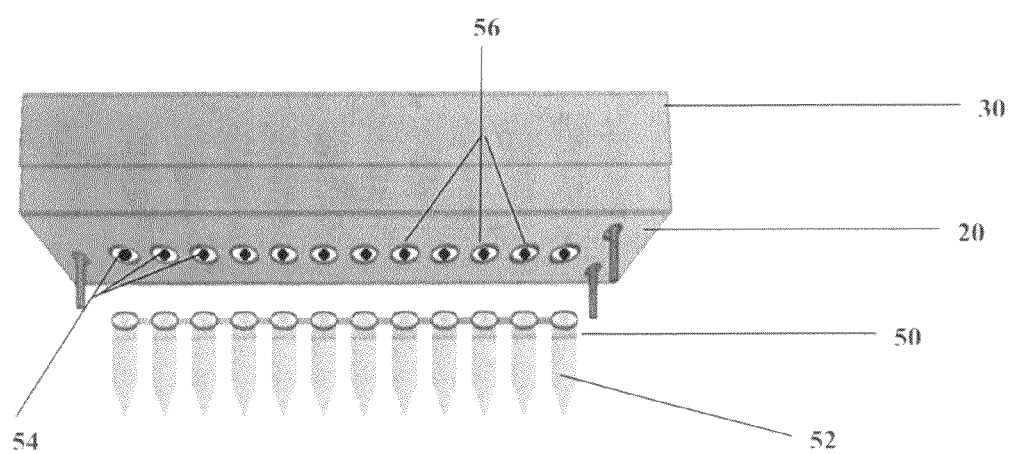
FIG. 7 is a perspective view of the magnetic separation device of FIG. 6 after lid removal.

Back in its initial position, device 10 is returned to the vial rack (not shown) such that vials 50 are placed back in the vial rack. The vials 50 are opened by plate 20, which is held tightly against sheath 30 by the operator and removed from the vials 50, thereby removing lids 56 from vials 50 as illustrated in FIG. 7. With plate 20 still magnetically connected to sheath 30 and lids 56 within the lid strip 58 still fixed between plate 20 and sheath 30, magnetic beads 54 remain collected at the center of lids 56 due to the concentrated magnetic field of orienting pins 34 of sheath 30. Vials 50, contaminated with reaction mixture 52, are discarded. The discarded vials 50 are replaced with new vials 60, containing a wash solution 62, which are placed in the vial rack. Lids 56, together with plate 20 and sheath 30, are repositioned on new vials 60, thereby closing new vials 60.

Figure 8:
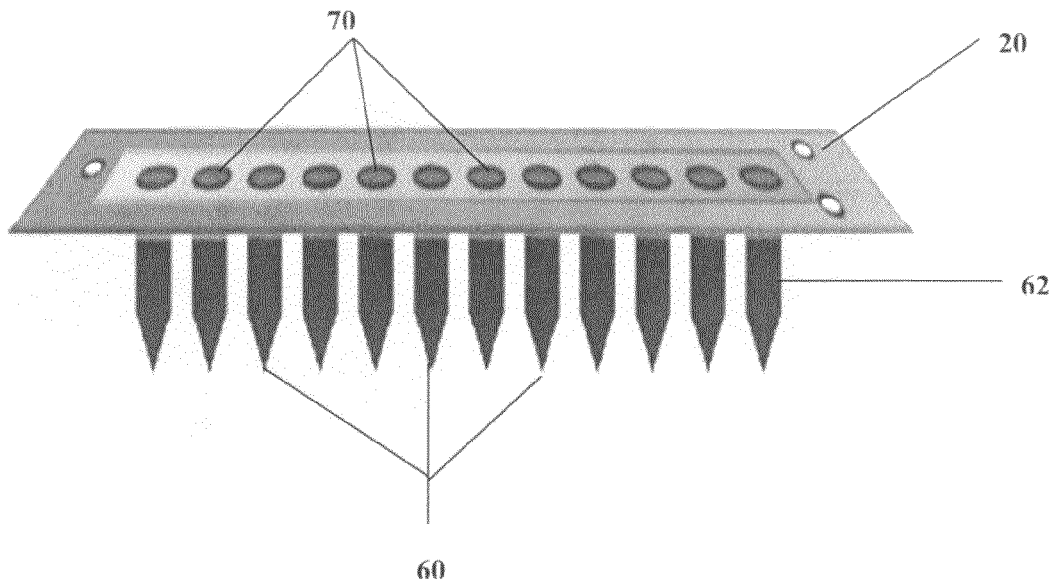
FIG. 8 is a perspective view of the plate of FIG. 2 with new lids and new vials for a washing procedure.
Figure 9A:
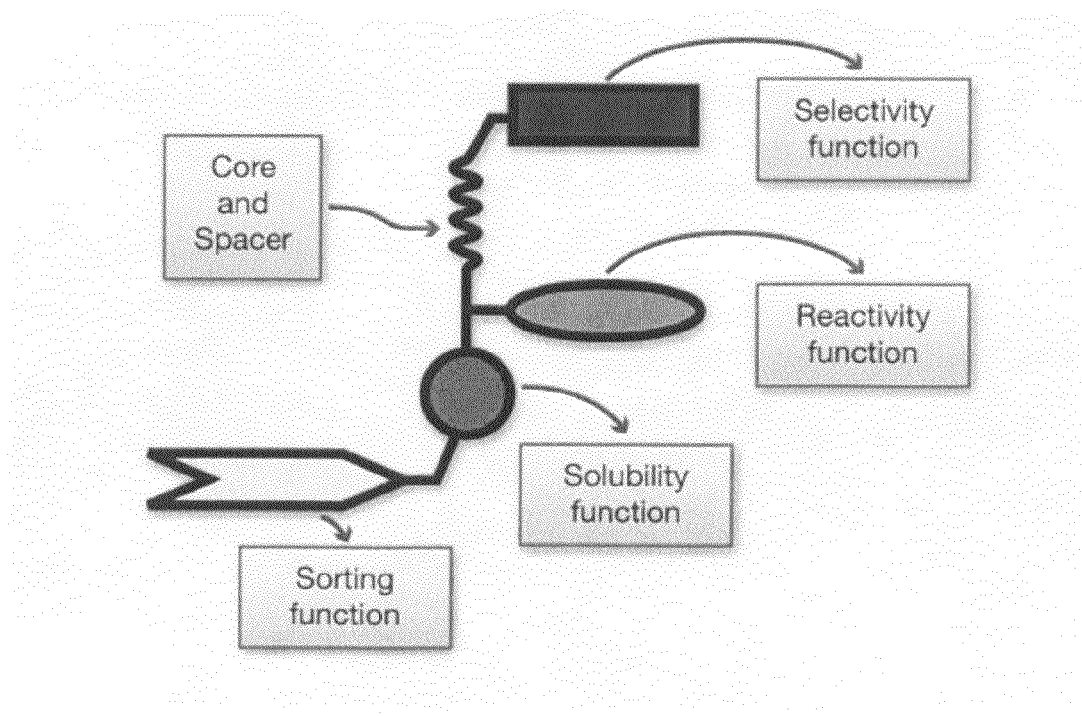
FIGS. 9A-9C are schematic depictions of exemplary capture compounds. The depicted compounds are those sold by Caprotec under their trademark Capture Compound™. These compounds are exemplary of compounds that can be presented on magnetic particles for use in the methods and with the devices provided herein.
Figure 9B:
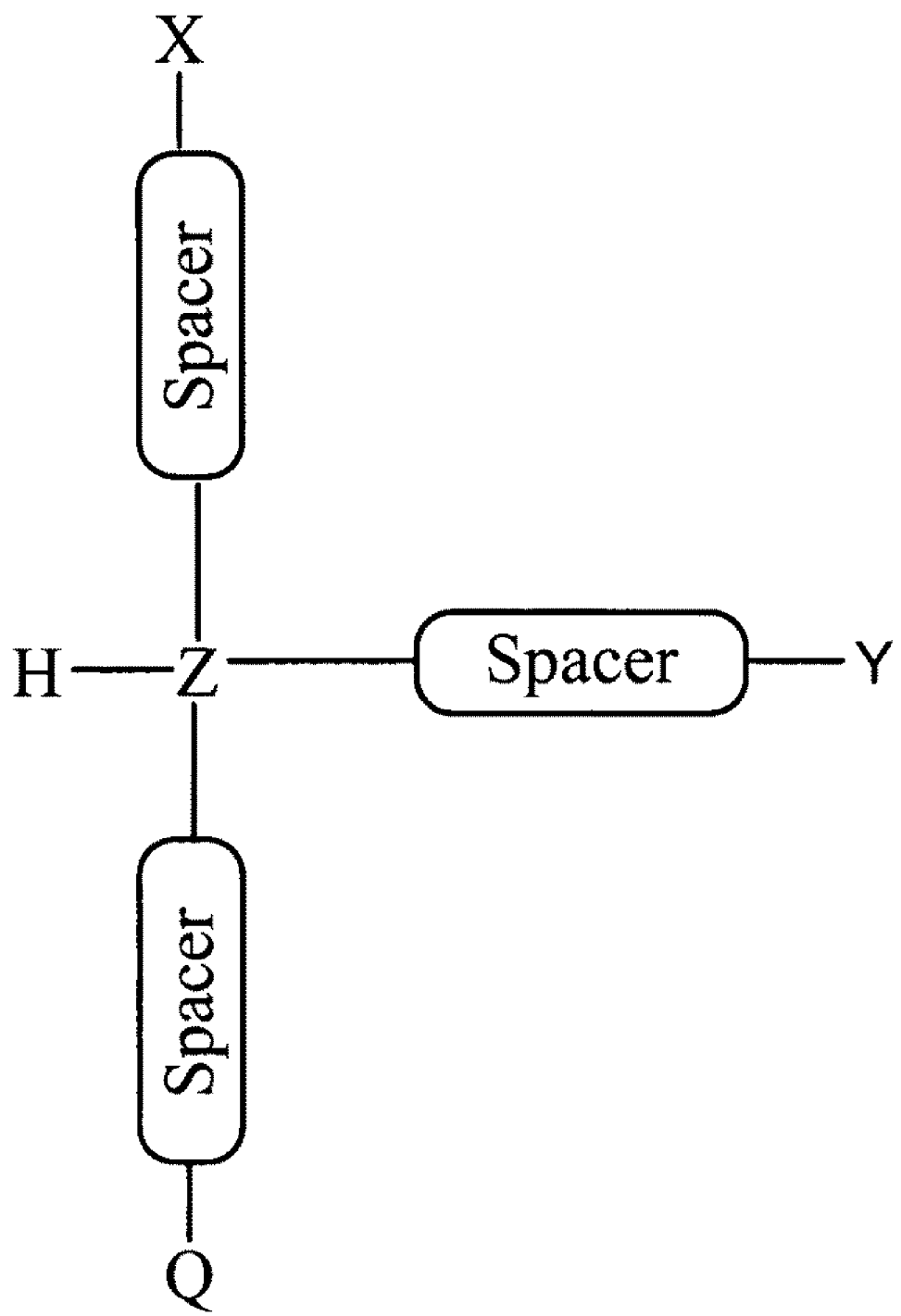
Figure 9C:
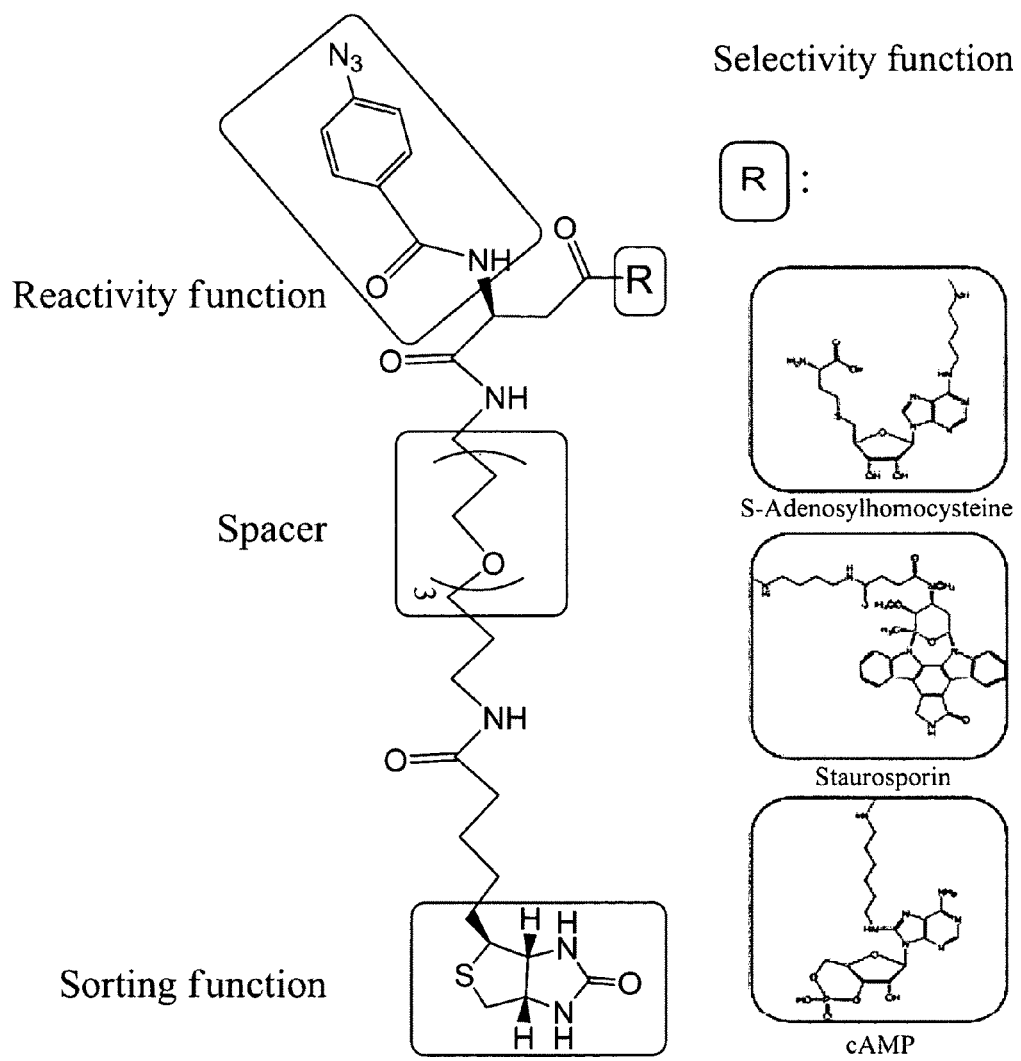

With magnetic beads 54 still retained on lids 56, sheath 30 is removed, allowing the beads to be re-suspended gently by the operator in wash solution 62 within new vials 60. While keeping plate 20 in place, lids 56 are removed and discarded and replaced by new lids 70 as illustrated in FIG. 8. After this procedure, plate 20 is embedded between new vials 60 and new lids 70. Magnetic beads 54 are now ready for collection from wash solution 62. This washing procedure can be repeated several times to wash magnetic beads 54 free from remaining contaminants originating from any remaining reaction mixture 52. After washing is complete, magnetic beads 54 are re-suspended in a desired solution for further processing.

Example 2

The device described herein allows the isolation of selected proteins out of complex biological samples without pipetting steps. In this example, capture compounds, for example, as described U.S. patent application Ser. No. 10/197,954, published as US-20030119021; U.S. patent application Ser. No. 10/760,085, published as US20050042771 and republished as US20060051879; U.S. patent application Ser. No. 10/388,027, published as US20040209255; Australian Pat. No. AU 2004206856; European Pat. No. EP 1485707; European Pat. App. EP 1 583 972; and Japanese Patent No. JP 3935487; and published International PCT application Nos. WO 03/092581 and WO 04/06497) are used to functionally reduce the complexity of a biological sample. All steps in the experimental procedure described in the following were performed at 0-4° C. unless stated otherwise. Bubbles were avoided during handling, as they may cause denaturation of proteins.

Four aliquots (A-D) of Streptavidin-coated magnetic beads loaded with the SAH compounds (available under the name caproBeads™, sold by caprotec bioanalytics Gmbh, Berlin, Germany) were prepared in standard 200 μL PCR vials by mixing 25 μL 100 μM SAH (S-adenosyl-L-homocysteine) Capture Compound (SAH-CC available as SAH CaproKit™ kit from caprotec bioanalytics GmbH, Berlin, Germany) with 50 μL 10 mg/ml streptavidin coated magnetic beads (Dynabeads® MyOne™ Streptavidin Cl from Invitrogen Dynal) for each aliquot. The resulting suspensions were vigorously shaken at room temperature for 2 min to allow binding of the biotin moiety of the SAH-CC to the streptavidin on the magnetic bead surface. The streptavidin-coated magnetic beads were collected using the device provided herein as described above. The supernatants were discarded and the caproBeads™ were washed once with 200 μL wash buffer 1 (50 mM Tris, 1 mM EDTA, 1 M NaCl, 0.5% Octyl-(3-D-glucopyranoside, pH 7.9) and collected as described above using the device described herein.

Four aliquots (A-D) of E. coli DH5α whole cell lysate were prepared in standard 200 μL PCR vials. Aliquots A and C contained 100 μL DH5α whole cell lysate with a total protein concentration of 5 mg/ml in capture buffer (20 mM HEPES, 50 mM KOAc, 10 mM Mg(OAc)$_2$, 10% Glycerol, pH 7.5). Aliquots B and D contained 100 μL E. coli DH5α whole cell lysate with a total protein concentration of 5 mg/ml and 2 mM S-adenosyl-L-homocysteine (SAH) as competitor of the selectivity function of the SAH-CC in capture buffer.

A 1 μL sample was drawn from aliquot A for further analysis (see below). The caproBeads™ beads A-D were suspended in the E. coli DH5α cell lysate solutions A-D, respectively, and kept in suspension by shaking for 3 hours at 4° C. to allow reversible binding of SAH binding proteins to the SAH selectivity function of the SAH-CC. The suspensions A and B were then placed in a UV light device, a CaproBox™ UV light and cooling device that provides UV irradiation and temperature control, and the suspensions were irradiated (310 nm, 10 mW/cm$^2$) for a total time of 30 minutes (the suspensions were mixed every 2.5 min) at 4° C. to form a covalent crosslink between the reactivity function of the SAH-CC to the SAH binding proteins. 20 μL of 10 mM SAH solution was added to suspension A, the suspension was homogenized and incubated for 10 min to displace all SAH binding proteins not covalently cross-linked to the SAH-CC. The caproBeads™ beads carrying the captured proteins were collected from the suspensions A-D, respectively, using the magnetic separator device described herein, the supernatants were discarded and the caproBeads™ beads carrying the captured proteins were washed three times with 200 µL wash buffer 1 (50 mM Tris, 1 mM EDTA, 1 M NaCl, 0.05% Octyl-(3-D-glucopyranoside, pH 7.9), three times with 200 µL wash buffer 2 (50 mM NH$_4$OAc, 0.025% Octyl-(3-D-glucopyranoside, pH 9.0), once with 200 µL water and collected according to the previously described protocol (see above) using the magnetic separator device provided herein. The collected beads A-D carrying the captured proteins were resuspended in 20 µL SDS sample buffer (50 mM Tris.HCl, 320 mM β-mercaptoethanol, 2.5% SDS, 0.05% bromophenol blue, 10% glycerol, pH 6.8). The 1 µL sample drawn from aliquot A was mixed with 19 µL SDS sample buffer; 5 µL of this solution were used for analysis (0.25% of aliquot A). The samples in SDS sample buffer (beads A-D and 0.25% of aliquot A) were heated 10 min to 95° C. and analyzed by SDS-PAGE (OLS® ProPage 4-20% Tris/Glycine pre-cast gel with 25 mM Tris base, 200 mM Glycin, 0.1% SDS, pH 8.3 as SDS running buffer) with subsequent silver staining (ProteoSilver™ Silver Stain Kit from Sigma) of the gel. A picture of the gel is shown in FIG. 10.

The following refers to FIG. 10. MW denotes the molecular weight marker, the bands of which are labeled in kDa to the very left of the gel picture. The comparison between the *E. coli* lysate (lane L, where only 0.25% of the original lysate was subjected to SDS-PAGE) and lysates A-D reveals the dramatic reduction of proteome complexity. The bands on the gel appearing exclusively in lysate A and not in lysate B represent SAH binding proteins covalently attached to the SAH-CC. Lysate B included bands that represent non-SAH specific proteins covalently attached to the SAH-CC. Lysate C included bands that represent proteins isolated from the lysate without covalent cross-link to the SAH-CC (pull-down) and lysate D included bands that correspond to pulled-down proteins in the presence of SAH competitor (non-specific pull-down). When comparing lysate A to lysate C, it is evident that many proteins were lost in the pull-down experiment (lysate C) compared to the capture assay (lysate A) due to the lack of a covalent bond between the SAH-CC and the proteins. The magnetic separator device provided herein was successfully used during the sample preparation process.

Example 3

The device described herein allows the isolation of selected proteins out of complex biological samples, such as cell lysates, using capture compounds in solution or capture compounds immobilized on a magnetic solid support, such as a magnetic bead. In this example, Capture compounds in solution and immobilized on magnetic beads are used to selectively isolate proteins. All steps in the experimental procedure described in the following were performed at 0-4° C. unless stated otherwise. Bubbles were avoided during handling, as they may cause denaturation of proteins.

This Example also describes the use of SAH Capture compounds to probe the methylome. Capture compounds used in these experiments are available from caprotec bioanalytics GmbH, Berlin, Germany and are as follows:

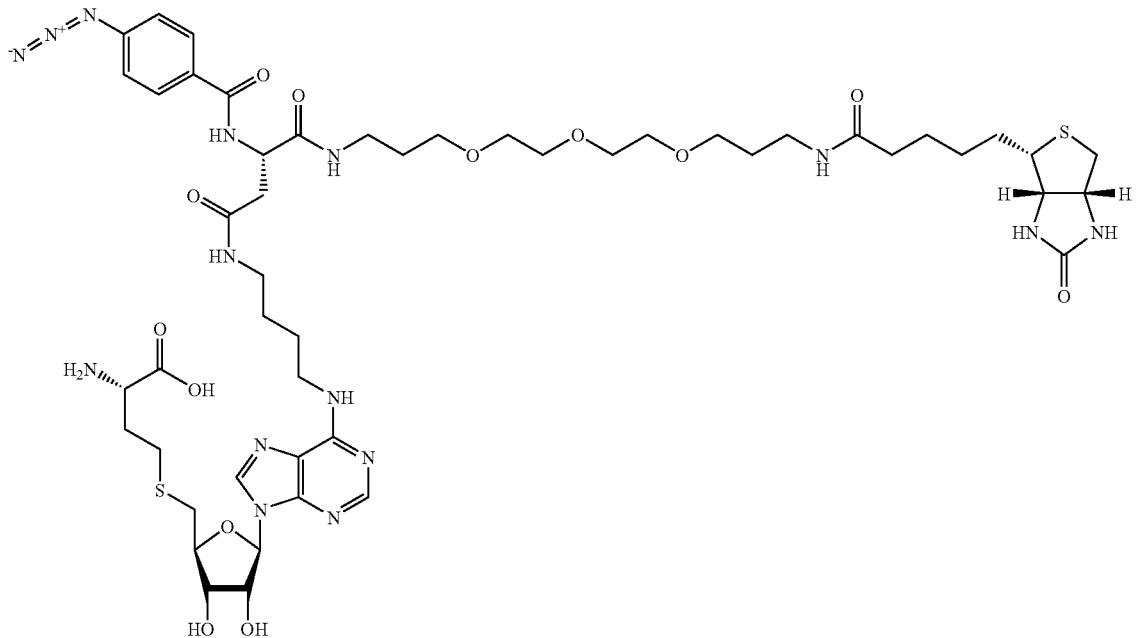

B1-N6-SAH

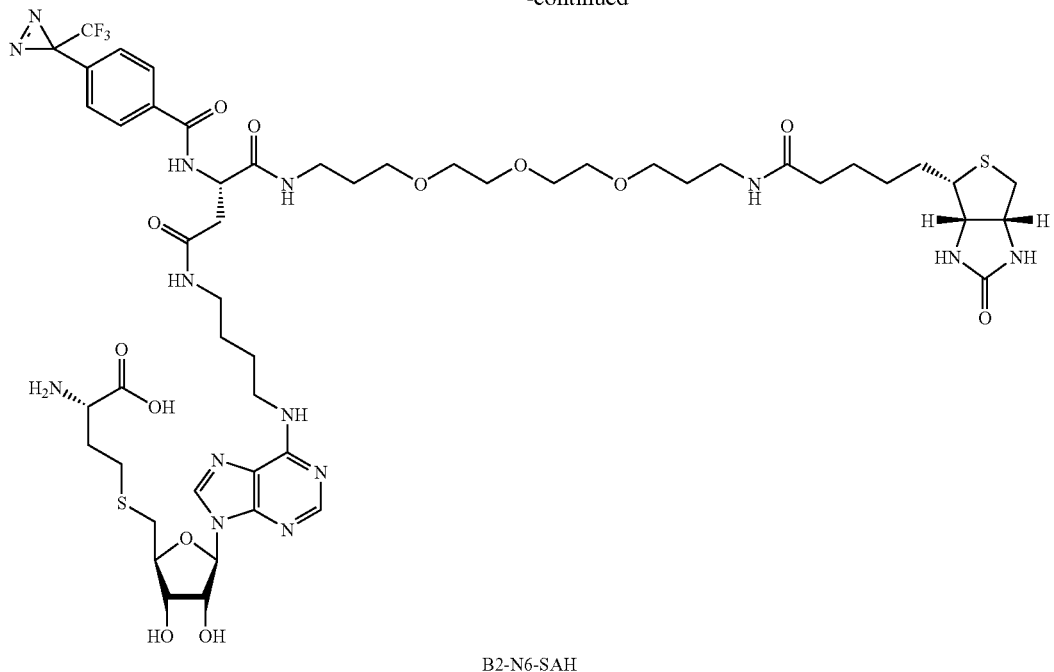

B2-N6-SAH

These compounds present S-adenosyl-homocysteine (SAH) as the Y function and are employed to probe the proteome to assess its interactions and thereby probe the "methylome." S-adenosyl-L-methionine (SAM) is a major source of methyl groups and hence is used by a variety of methyltransferases. The enzymes that transfer the methyl group of SAM is designated the methylome. The above compounds employ SAH, a stable SAM analog, as the selectivity function to probe the methylome.

In capture compound B1-N6-SAH and B2-N6-SAH, the sorting function is biotin, the selectivity function is S-adenosyl-homocysteine, the core, Z, is aspartic acid, and the spacer linking the core to the sorting function is ($-CH_2-CH_2-O-$)$_3$. In capture compound B1-N6-SAH, the reactivity function is phenylazide. In capture compound B2-N6-SAH, the reactivity function is 3-phenyl-3-trifluoromethyldiazirine. Reaction with cell lysates will identify any molecules, particularly enzymes, that interact with SAH. Similar compounds in which Y is staurosporine or cAMP, a ubiquitous second messenger for isolation of cAMP-binding proteins (a capture compound scaffold is attached to the C8, C2 or N8 position of cAMP) have been prepared. Other such compounds that present a Y function with which a family of enzymes or other group of proteins interact can be used to probe various subsets of the proteome.

A. Pre-Treatment of Cell Lysates

Small molecules, such as, for example, S-adenosyl-L-homocysteine (SAH) or S-adenosyl-L-methionine (SAM), that are structurally similar to the selectivity function, can inhibit binding of the selectivity function of the capture compound. Therefore, small molecules were removed from *E. coli* cell lysates by gel filtration (e.g., using SEPHADEX G-25), repetitive membrane filtration or dialysis.

B. Capture of Biomolecules with Magnetic Beads, Such as caproBeads™ Beads (i) Preparation of the Beads, Such as caproBeads™ Beads Streptavidin coated magnetic beads loaded with caprotec Capture Compound™ compound B1-N6-SAH or B2-N6-SAH were prepared in standard 200 µL PCR vials by mixing well resuspended streptavidin magnetic beads (50 µl, 10 mg/ml), such as, for example Dynal Dynabeads™ MY ONE™ Streptavidin Cl (Invitrogen), with the caprotec Capture Compound™ compound (25 µl, 100 µM). In caprotec Capture Compound™ compound B1-N6-SAH and B2-N6-SAH, the sorting function Q is biotin, the selectivity function Y is S-adenosyl-L-homocysteine, the core function Z is aspartic acid, and the spacer L linking the core to the sorting function is ($-CH_2-CH_2-O-$)$_3$. In a caprotec Capture Compound™ compound designated B1-N6-SAH, the reactivity function X is phenylazide. In a caprotec Capture Compound™ compound designated B2-N6-SAH, the reactivity function X is 3-phenyl-3-trifluoromethyldiazirine.

The mixtures were vigorously shaken for 2 minutes at room temperature to allow binding of the biotin moiety of the caprotec Capture Compound™ compounds to the streptavidin on the magnetic bead surface. Magnetic caproBeads™ beads were collected using the device provided herein, and washed with 200 µL wash buffer 1 (WB1) (50 mM Tris, 1 mM EDTA, 1 M NaCl, 0.05% octyl-β-D-glucopyranoside, pH 7.9). The collection and wash steps were repeated, and the caproBeads™ beads were stored in the lids of the PCR tube strips until incubation with cell lysates.

(ii) Reaction of Cell Lysates with caproBeads™

All reactions were performed at 4° C. *E. coli* whole cell lysates (2-5 mg/ml protein concentration) were prepared to a final volume of 100 µl in capture buffer (20 mM HEPES, 50 mM KOAc, 10 mM Mg(OAc)$_2$, 10% Glycerol, pH 7.5). A 1 µL sample was drawn from each reaction as a control for further analysis. Four reactions were performed by addition of caproBeads™ beads to cell lysates. Each of the two different caproBead™ beads was used in two reactions. Two reactions contained cell lysates and caproBeads™ beads containing caprotec Capture Compound™ compound B1-N6-SAH (reactions 3 and 4), and two reactions contained cell lysates and caproBeads™ beads containing caprotec Capture Compound™ compound B2-N6-SAH (reactions 7 and 8). Reactions 4 and 8 were control reactions to which SAH (S-adenosyl-L-homocysteine) was added to the cell lysate as competitor to a final concentration of 2 mM prior to adding the caproBeads™ beads.

After the caproBeads™ beads were added to cell lystates, the suspension was incubated at 4° C. for at least 3 h with gentle resuspension to allow reversible binding of SAH- and/or SAM-binding proteins to the SAH selectivity function of the capture compounds immobilized on caproBeads™ beads. The suspensions were then placed in a CaproBox™ UV light and cooling device and irradiated for 30 min, with mixing at least every 2½ minutes, to form a covalent crosslink between the reactivity function and the SAH- and/or SAM-binding proteins. After irradiation, SAH (20 µl, 10 mM) was added to reactions without SAH (reactions 3 and 7), and the reactions were incubated for 10 minutes with gentle resuspension at least every 5 minutes to displace non-covalently bound proteins. In all reactions, the caproBeads™ beads were collected using the magnetic separator device described herein and resuspended in WB1 (50 mM Tris, 1 mM EDTA, 1 M NaCl, 0.05% octyl-β-D-glucopyranoside, pH 7.9) (200 µl). The mixtures were transferred to a new reaction tube and incubated for 2 minutes. The beads were collected using the device provided herein and as described herein, and washed an additional two times in WB1 (200 µl) and an additional three times in wash buffer 2 (50 mM NH₄OAc, 0.025% octyl-β-D-glucopyranoside, pH 9.0) according to the previously described protocol (see above) using the magnetic separator device provided herein without changing the reaction tube. After the final wash step, the supernatant was discarded, and proteins bound to the caproBeads™ beads were analyzed by SDS-PAGE.

C. Capture of Biomolecules by Capture Compounds in Solution (i) Pretreatment of Cell Lysates When capturing in solution, proteins in cell lysates that can interact with the beads are removed or blocked prior to mixing the cell lysate with the capture compound to reduce background reactions. This background does not occur when using caproBeads™.

In the capture experiments with caprotec Capture Compound™ compound B1-N6-SAH or B2-N6-SAH, intrinsically biotinylated proteins in cell lysates were separated by pre-treatment with streptavidin magnetic beads or by blocking intrinsically biotinylated proteins with streptavidin. Pre-treatment with streptavidin magnetic beads was accomplished by adding streptavidin magnetic beads (Dynal Dynabeads™ MYONE™ Streptavidin C1, Invitrogen) (10 mg/ml) to the cell lysate and incubating for 30 minutes at 4° C. with gentle shaking. The beads were collected using the device provided herein and as described herein and the cell lysates used for subsequent experiments. Alternatively, intrinsically biotinylated proteins were blocked by incubation with streptavidin. After incubation for at least 15 min at 0° C., excess streptavidin was blocked by addition of biotin in a 4:1 molar ratio with respect to added streptavidin. Following this procedure, biotin within intrinsically biotinylated proteins is replaced by the same amount of free biotin. Since the streptavidin magnetic beads have a higher capacity for free biotin than for biotinylated proteins, the generated free biotin hardly affects the capture process described in the following.

(ii) Capture of Biomolecules by Capture Compounds in Solution

All reactions were performed at 4° C. A stock solution of capture compound (100 µM) in capture buffer (20 mM HEPES, 50 mM KOAc, 10 mM Mg(OAc)₂, 10% Glycerol, pH 7.5) was added to an *E. coli* cell lysate in capture buffer to a final volume of 100 µL. Final concentrations of capture compound were 5-10 µM and final concentrations of cell lysate were 2-5 mg/ml, respectively. Four reactions were performed by addition of capture compound to cell lysate. Two reactions contained caprotec Capture Compound™ compound B1-N6-SAH (reactions 1 and 2), and two reactions contained caprotec Capture Compound™ compound B2-N6-SAH (reactions 5 and 6). Reactions 2 and 6 were control reactions to which S-adenosyl-L-homocysteine (SAH) was added to the cell lysate as competitor to a final concentration of 2 mM prior to adding the capture compounds. A 1 µL sample was drawn from each reaction as a control for further analysis, and the mixtures were incubated at 4° C. for 30 min with gentle mixing to allow reversible binding of SAH- and/or SAM-binding proteins to the SAH selectivity function of the capture compounds.

The solutions were placed in a CaproBox™ UV light and cooling device and irradiated for 10 minutes. After irradiation, SAH (20 µL, 10 mM) was added to reactions without SAH (reactions 1 and 5) and the reactions were incubated for 10 minutes with gentle mixing to displace non-covalently bound proteins. After incubation, 25 µl of 5×WB1 (250 mM Tris, 5 mM EDTA, 5 M NaCl, 0.25% octyl-β-D-glucopyranoside, pH 7.9) was added, and the reactions were gently mixed. Then, 50 µL of well resuspended streptavidin magnetic beads (50 µl, 10 mg/ml), such as, for example Dynal Dynabeads™ MYONE™ Streptavidin C1 (Invitrogen), was added, and the resulting mixtures were incubated for 30 min with gentle resuspension at least every 5 minutes to allow binding of the biotin moiety of the capture compounds to the streptavidin on the magnetic bead surface. The magnetic beads were collected using the device provided herein as described herein and washed an additional two times in WB1 (200 µl) and an additional three times in wash buffer 2 (50 mM NH₄OAc, 0.025% octyl-β-D-glucopyranoside, pH 9.0) according to the previously described protocol (see above) using the magnetic separator device provided herein without changing the reaction tube. After the final wash step, the supernatant was discarded, and proteins bound to the magnetic beads were analyzed by SDS-PAGE.

D. SDS PAGE Analysis of Captured Biomolecules

The magnetic beads carrying the captured proteins were resuspended in 20 µL SDS sample buffer (50 mM Tris.HCl, 320 mM β-mercaptoethanol, 2.5% SDS, 0.05% bromophenol blue, 10% glycerol, pH 6.8). The 1 µL control samples drawn were mixed with 19 µL sample buffer; 5 µL of this solution were used for analysis. Captured proteins were monitored by SDS-PAGE followed by silver staining. The samples in SDS sample buffer were heated 10 min to 95° C. and analyzed by SDS-PAGE (OLS® ProPage 4-20% Tris/Glycine pre-cast gel with 25 mM Tris base, 200 mM Glycine, 0.1% SDS, pH 8.3 as SDS running buffer) with subsequent silver staining (ProteoSilver™ Silver Stain Kit from Sigma) of the gel. A picture of the gel is shown in FIG. 11.

The following refers to FIG. 11. Reactions performed with caproBeads™ beads presenting caprotec Capture Compound™ compound B1-N6-SAH or B2-N6-SAH (reactions 3 and 7, respectively) had fewer protein bands than reactions performed with the corresponding capture compound in solution (reactions 1 and 5, respectively). Furthermore, the majority of proteins that were captured by capture compounds in solution, but not by caproBeads™ beads, were not competed off in the presence of soluble SAH (S-adenosyl-L-homocysteine) (reactions 2 and 6, respectively). This indicates that many proteins captured by capture compounds in solution were not captured because of specific interactions with the SAH selectivity function.

In contrast, several protein bands that were captured by caproBeads™ were competed off in the presence of soluble SAH. These protein bands were also captured in experiments with soluble capture compound. For example, gel lanes of proteins bound to caprotec Capture Compound™ compound B1-N6-SAH or B2-N6-SAH in solution (reactions 1 and 5, respectively) contained two bands, located near the 25 kD molecular weight marker, as well as a small band located between the 30 and 40 kD molecular weight markers. These bands did not appear or were significantly reduced in control reactions containing soluble SAH as competitor (reactions 2 and 6, respectively). In the caproBead™ experiments (reactions 3 and 7), these bands were more prominent than in the solution experiments (reactions 1 and 5). For example, the band located between the and 40 kD molecular weight markers was larger in the caproBead™ bead experiments than in the experiments performed with capture compounds in solution. These experiments reveal that immobilization of capture compounds increases their specificity and reduces non-specific interactions between capture compounds and proteins.

Example 4

Separation of Magnetic Beads with Compounds of Interest

Streptavidin coated magnetic beads were incubated with an *Escherichia coli* cell lysate and washed using a magnetic separator as described herein and washed using the procedure used in the art (beads collected at the inner wall of the tube by holding a neodymium magnet against the outer wall of the tube and removing the supernatant by manual pipetting). The efficiency of the two wash techniques was evaluated by i) the weight of beads plus adherent supernatant (wash solution) (see FIG. 12 and Table 2) and ii) the protein content of the wash solution (see FIG. 13). The lower the weight of beads plus adherent supernatant, the better the removal of the wash solution and the less carry over of unwanted proteins to the next wash step.

Detailed Procedure:

The weight of ten 200 µL PCR tubes plus corresponding lids was determined.

In the first two tubes, respectively, 150 µL *Escherichia coli* DH5α whole cell lysate (2 mg/mL total protein concentration) in buffer (20 mM HEPES, 50 mM KOAc, 10 mM Mg(OAc)2, 10% glycerol, pH 7.9) was mixed with 50 µL magnetic Dynabeads®MyOne™ Streptavidin C1 (Invitrogen, Carlsbad, Calif.) and incubated for 10 min at 4° C. while keeping the beads in suspension by continuously turning the tubes up-side-down. The magnetic beads were collected, respectively, by a high performance neodymium magnet, and the supernatant was discarded. For one tube, the collection was performed in the lids of the tubes using a magnetic device as described herein (e.g., a caproMag™ magnetic device) and a new pre-weighed tube was closed with the lid containing the collected beads. For the other tube, the beads were collected at the inner wall of the tube by holding the neodymium magnet of the caproMag™ magnetic device against the outer wall of the tube and removing the supernatant by manual pipetting (prior art usual procedure). The weight of the beads plus adherent supernatant was determined, respectively, by subtracting the weight of the tube and lid from the weight of the tube and lid containing the separated beads plus adherent supernatant (see FIG. 12 and Table 2, data corresponding to "Lysate").

The beads collected a magnetic device as described herein (e.g., a caproMag™ magnetic device) using the washing procedures described herein (referred to as "caproMag™ washing procedure") were re-suspended in 200 µl ultrapure water, the lid was replaced with a new pre-weighed lid and the beads were again collected in the new lid by using the caproMag™ magnetic device. A new pre-weighed tube was sealed with the lid containing the collected beads and the weight of the beads plus adherent supernatant was determined (see FIG. 12 and Table 2, data corresponding to "Wash 1"–"caproMag"). The supernatant wash water was lyophilized to dryness, 10 µL SDS-sample buffer was added, the sample heated 10 min to 95° C., and subjected to SDS-PAGE/silver stain analysis (see FIG. 13, lane "Wash 1"–"cM"). This procedure was repeated three times (see FIGS. 12 and 13 as well as Table 2).

TABLE 2

Values corresponding to FIG. 12.

| | Weight of beads plus adherent solution/g | |
|---|---|---|
| | caproMag ™ | usual procedure |
| Lysate | 0.0054 | 0.0123 |
| Wash 1 | 0.0044 | 0.0096 |
| Wash 2 | 0.0040 | 0.0071 |
| Wash 3 | 0.0033 | 0.0050 |
| Wash 4 | 0.0027 | 0.0032 |

The beads collected from the lysate by the usual procedure were re-suspended in 200 µL ultrapure water and transferred by manual pipetting to a new pre-weighed tube. The beads were collected at the wall of the tube as described above. The supernatant was removed by manual pipetting, lyophilized to dryness, 10 µl SDS-sample buffer was added, heated 10 min to 95° C., and subjected to SDS-PAGE/silver stain analysis (see FIG. 13, lane "Wash 1"–"U"). The weight of the beads plus adherent supernatant was determined (see FIG. 12 and Table 2, data corresponding to "Wash 1"–"usual procedure"). This procedure was repeated three times (see FIGS. 12 and 13 as well as Table 2).

The magnetic beads after the four wash steps performed by either using the caproMag™ washing procedure, in which the beads were collected in the lid of the tube and the supernatant in the tube was discarded with the tube, or the usual procedure, in which the beads were collected at the side of the tube and the supernatant removed using a pipette, were subjected to SDS-PAGE/silver stain analysis (see FIG. 13, lanes "washed beads"–"cM" and "U"). The beads were therefore suspended in 10 µL SDS-sample buffer, heated 10 min to 95° C. and the whole suspension was transferred into the gel pocket.

FIG. 13 shows SDS-PAGE/silver stain analysis of the protein content within successive wash solutions for washing streptavidin coated magnetic beads pre-incubated with *Escherichia coli* cell lysate. Because the streptavidin is only cleaved from the beads when applying harsh denaturing conditions, such as used for preparing the SDS-PAGE samples, the streptavidin band is a measure of the amount of beads present. Using the caproMag™ washing procedure as described herein, the amount of beads unintentionally removed together with the supernatant wash solution is lower than using the usual procedure, which requires pipetting. Washing is more efficient using the caproMag™ washing procedure, in which the beads are magnetically collected in the lid of a tube and the tube with supernatant is discarded, compared to the usual pipetting procedure, as can be seen by the lower protein content in the wash fractions (most profoundly observed in wash 2). The wash water 3 using the caproMag™ washing procedure contains about the same low protein content as the wash water 4 using the usual procedure. Additionally, the loss of beads during each washing step is reduced when using the caproMag™ washing procedure as can be seen by the less intense streptavidin bands (marked by arrows).

FIG. 12 and Table 2 give the weight of beads plus adherent supernatant after removal of the respective supernatant (cell lysate or the following water wash solutions) using either the caproMag™ washing procedure or the usual procedure (beads collected at the inner wall of the tube by holding a neodymium magnet against the outer wall of the tube and removing the supernatant by manual pipetting). FIG. 13 gives the protein content of the respective wash solutions analyzed by SDS-PAGE and subsequent silver stain of the gel. It is evident from FIGS. 12 and 13 and Table 2 that for each of the separation and wash steps, the caproMag™ washing procedure outperforms the usual procedure:

a) More supernatant solution is removed from the beads by using the caproMag™ washing procedure compared to the usual procedure, which can be seen from the lower weight of beads plus adherent supernatant when using the caproMag™ procedure (FIG. 12 and Table 2).

b) As a result, the washing solutions, in which the supernatants of the previous separation steps are dissolved, contain a lower protein content when using the caproMag™ procedure (FIG. 13).

Thus, fewer washing steps are necessary when using the caproMag™ procedure: The wash water 3 using the caproMag™ procedure contains about the same low protein content as the wash water 4 using the usual procedure. The better performance of the caproMag™ procedure can be most profoundly observed in the protein content of the wash water 2. Additionally, the 13 kDa bands within the wash fractions originating from the streptavidin, with which the beads are coated (marked with arrows in FIG. 13), suggest that fewer beads are unintentionally removed with the wash solution using the caproMag™ procedure than using the usual pipetting procedure. Note that the streptavidin is only cleaved from the beads when applying harsh denaturing conditions (boiling the samples in SDS sample buffer). Thus, the streptavidin band is a measure for the amount of beads unintentionally removed together with the supernatant wash solution. Rated from the streptavidin band detectable by SDS-PAGE analysis of the 4× washed beads, the amount of beads after 4 wash steps is approximately the same with the two methods (FIG. 13, lanes "washed beads"). However, comparing the low intensity protein bands detectable by SDS-PAGE analysis of the 4× washed beads (FIG. 13, lanes "washed beads"), the protein amount on the beads washed using the caproMag™ procedure seems to be slightly higher, suggesting that slightly more beads were retained using the caproMag™ procedure than when using the usual pipetting procedure. In conclusion, washing is more efficient using a magnetic device as described herein (e.g., a caproMag™ magnetic device) and caproMag™ washing procedure compared to the usual pipetting procedure as can be seen by the lower protein content in the wash fractions (most profoundly observed in wash 2). The wash water 3 using the caproMag™ magnetic device and washing procedure contains about the same low protein content as the wash water 4 using the usual pipetting procedure. Additionally, the loss of beads during each washing step is reduced when using the caproMag™ magnetic device and washing procedure.

Example 5

Time Required for Washing

In another experiment, the time was measured for washing beads from twelve parallel samples with additionally changing the tubes a) using a magnetic device as described herein (e.g., a caproMag™ magnetic device) and b) using the usual pipetting procedure, the results of which are shown in FIG. 14 and Table 3. Steps included for comparison are i) collection of 500 µg beads from a 200 µL suspension, ii) separation of the supernatant, iii) transfer of the beads to new tubes, iv) resuspension of the beads in 200 µL of new wash solution, and v) exchange of the lids (note that steps iii) and iv) are interchanged in the usual procedure with respect to the described caproMag™ procedure).

TABLE 3

Values corresponding to FIG. 14.

| | Time for washing 12 bead samples in parallel/(minutes:seconds) | |
|---|---|---|
| | caproMag ™ | usual procedure |
| Experiment 1 | 2:20 | 6:50 |
| Experiment 2 | 2:03 | 7:40 |
| Experiment 3 | 2:11 | 7:20 |
| Experiment 4 | 2:06 | 7:00 |

The time for washing beads from twelve parallel samples and change of the tube is about 2 minutes when using the caproMag™ magnetic device and caproMag™ washing procedure compared to about 7 minutes when applying the usual pipetting procedure (see FIG. 14 and Table 3). Additionally, the usual procedure with manual pipetting produces more waste and costs (1 to 2 additional pipette tips per bead sample and wash step). Another important advantage of the caproMag™ magnetic device and caproMag™ washing procedure is the parallelization of wash steps resulting in drastically reduced operation time. Thus, the caproMag™ magnetic device and caproMag™ washing procedure results in time and cost saving, less labor intensive procedures, and yields results better than those achieved using the usual pipetting procedure.

While various embodiments of the subject matter provided herein have been described, it should be understood that they have been presented by way of example only, and not limitation. For example, the magnetic separator device disclosed and described herein is not limited to the physical arrangements or dimensions illustrated or described, nor is the disclosed device limited to any particular design or materials of construction nor to any method of use or application.

Since modifications will be apparent to those of skill in this art, it is intended that this invention be limited only by the scope of the appended claims.

What is claimed:
1. A device, comprising:
  a sheath comprising a magnet and including a plurality of orienting pins that each concentrate or direct a magnetic field of the magnet;
  vessels;
  vessel lids; and
  a magnetizable plate;
  wherein:
    the magnetizable plate is configured to receive the sheath and is configured to receive vessel lids;
    the magnetizable plate is configured to position the orienting pins over the vessel lids;
    each orienting pin is adapted to concentrate or direct a magnetic field of the magnet to a vessel lid in the magnetizable plate; and when the vessel lids are engaged with the vessels, the magnetizable plate is positioned between the vessel lids and the vessels.

2. The device of claim 1, wherein:
the magnet is embedded in the sheath;
the orienting pins are integrated into the sheath; and
each orienting pin concentrates or directs a magnetic field of the magnet to the middle of its associated vessel lid and allows for the concentrated collection of magnetic particles in the middle of the lids.

3. The device of claim 1, wherein the magnet is a permanent magnet, a high performance magnet, a rare earth magnet or an electromagnet.

4. The device of claim 1, wherein the magnet is selected from among an R-cobalt magnet and an R—Fe—B magnet, wherein R is selected from among lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu)), scandium (Sc) and yttrium (Y).

5. The device of claim 1, wherein the magnet is a neodymium magnet.

6. The device of claim 1, wherein the magnet has a $(BH)_{max}$ of from 5 MGOe to 50 MGOe, at least 25 MGOe, from 20 MGOe up to 90 MGOe; or from 25 MGOe up to 50MGOe.

7. The device of claim 1, wherein the magnet has a remanence from about 3 kG to about 20 kG.

8. The device of claim 1, wherein the magnet has an intrinsic coercivity of greater than 5 kOe.

9. The device of claim 1, wherein the sheath comprises a non-magnetic material.

10. The device of claim 1, wherein the sheath is aluminum or an aluminum alloy.

11. The device of claim 1, wherein the magnet is embedded in the sheath.

12. The device of claim 1, wherein the sheath includes a bottom comprising the orienting pins.

13. The device of claim 12, wherein the magnet is attached to one face of the bottom of the sheath.

14. The device of claim 13, wherein the magnet is attached to one face of the bottom of the sheath by magnetic attraction to the orienting pins, or by an adhesive, or by a mechanical connector.

15. The device of claim 1, wherein:
the magnet is attached to the bottom of the sheath; and
the sheath has no side walls; or
the sheath has no front, rear or side walls and no top; or
the sheath comprises at least two sides and the bottom and the at least two sides define a cavity sized to receive the magnet through an open top or an optional closed top that is removable to expose the cavity.

16. The device of claim 1, wherein:
the sheath comprises a bottom containing the orienting pins; and
the orienting pins traverse the thickness of the bottom of the sheath; or
the orienting pins do not fully traverse the thickness of the bottom of the sheath leaving one face of the bottom of the sheath unpenetrated; or,
the orienting pins do not fully traverse the thickness of the bottom of the sheath leaving the face of the bottom of the sheath pointing towards the magnet unperforated; or
the orienting pins do not fully traverse the thickness of the bottom of the sheath leaving the face of the bottom of the sheath pointing towards the lids of the vessels unperforated; or
the orienting pins do not fully traverse the thickness of the bottom of the sheath and are embedded into the material of the bottom of the sheath leaving all faces of the bottom of the sheath unperforated.

17. The device of claim 1, wherein the orienting pins are of a material having a magnetic permeability higher than the magnetic permeability of the material from which the sheath is fabricated.

18. The device of claim 1, wherein the orienting pins are formed of iron, steel, a mu metal or a soft magnetic alloy comprising about 80% nickel, 5% copper, 2% chromium, and 15% iron.

19. The device of claim 1, wherein:
one or more of the orienting pins is a magnet, and
the magnetic North pole face of the orienting pin(s) is positioned to face the magnetic South pole face of the magnet in the sheath or the magnetic South pole face of the orienting pin(s) is positioned to face the magnetic North pole face of the magnet in the sheath.

20. The device of claim 1, wherein the orienting pins in the sheath are arranged linearly or in a circular, rectangular or quadrangular array.

21. The device of claim 1, wherein the number of orienting pins in the sheath is an integer selected from among 2, 3, 6, 9, 12, 24, 36, 48 or 96 or a multiple thereof.

22. The device of claim 1, wherein:
the sheath further comprises a fit pin; and
the magnetizable plate further comprises a fit pin hole configured to receive the pin.

23. The device of claim 22, wherein:
the sheath includes an edge having one or more fit pins and an opposite edge having a different number of fit pins to ensure only one orientation for the magnetizable plate and the sheath; or
the sheath includes one fit pin at one edge and two or more fit pins on the opposite edge, each pin configured to align with corresponding fit pin holes.

24. The device of claim 1, wherein the magnetizable plate is configured to accept a vessel lid of a vessel including multiple chambers.

25. A device of claim 1, wherein each of the sheath comprising the magnet and the magnetizable plate is rectangular or is circular.

26. The device of claim 1, wherein the magnetizable plate is formed of steel or iron or of a soft magnetic alloy comprising about 80% nickel, 5% copper, 2% chromium, and 15% iron.

27. The device of claim 1, further comprising a rack for holding a plurality of vessels.

28. The device of claim 27, wherein:
the vessels comprise vials, and the rack is configured to receive the vials; or
the vessels comprise a multi-well plate, and the rack is configured to receive the multi-well plate.

29. A kit, comprising:
a device of claim 1; and
magnetic particles and optionally vessels or multiwell plates and optionally instructions for use.

30. The kit of claim 29, further comprising a capture compound that comprises a sorting function.

31. The kit of claim 30, wherein the sorting function comprises one member of a specific binding pair.

32. The kit of claim 31, wherein the magnetic particles include on their surface the corresponding member of the binding pair.

33. The kit of any claim 30, wherein the sorting function is biotin and the magnetic particle includes on its surface avidin or streptavidin.

34. A system, comprising:
a device of claim 1;
a device for providing light;
a capture compound comprising a light-activated reactivity function; and
optionally a device for analysis of biomolecules.

35. A system, comprising:
a device of claim 1;
a device for providing light;
a capture compound comprising a light-activated reactivity function; and a device for analysis of biomolecules, wherein the device for analysis is selected from among a mass spectrometer, an electrophoretic separator device, a surface plasmon resonance device and a chromatography device.

36. The system of claim 35, wherein the mass spectrometer performs time of flight mass spectrometry with matrix-assisted laser desorption ionization (MALDI-TOF), quadrupole ion trap mass spectrometry, secondary ion mass spectrometry, accelerator mass spectrometry, inductively coupled plasma-mass spectrometry, Ion Mobility Spectrometry-MS, Surface Enhanced Laser Desorption Ionization (SELDI-TOF), tandem mass spectrometry or Electrospray Ionization (ESI) mass spectrometry.

37. The system of claim 34, further comprising a computer programmed for analysis of captured biomolecules.

* * * * *